US012748092B1

(12) United States Patent
Kotowksi-Chang et al.

(10) Patent No.: US 12,748,092 B1
(45) Date of Patent: Sep. 29, 2026

(54) SYSTEMS FOR AND METHODS OF DETERMINING BEVERAGE COMPOSITIONS FOR ALUMINUM CAN PACKAGING

(71) Applicant: Archer Roose, Inc., Boston, MA (US)

(72) Inventors: Jan Kotowksi-Chang, N Bellmore, NY (US); Marian Leitner, Dartmouth, MA (US)

(73) Assignee: Archer Roose, Inc., Boston, MA (US)

( * ) Notice: Subject to any disclaimer, the term of this patent is extended or adjusted under 35 U.S.C. 154(b) by 0 days.

(21) Appl. No.: 19/384,215

(22) Filed: Nov. 10, 2025

(51) Int. Cl.
*G01N 33/14* (2006.01)
*G01N 35/00* (2006.01)
*G16C 20/30* (2019.01)
*G16C 20/70* (2019.01)

(52) U.S. Cl.
CPC ....... *G01N 33/14* (2013.01); *G01N 35/00663* (2013.01); *G16C 20/30* (2019.02); *G16C 20/70* (2019.02)

(58) Field of Classification Search
CPC .. G01N 33/14; G01N 35/00663; G16C 20/30; G16C 20/70
See application file for complete search history.

(56) References Cited

FOREIGN PATENT DOCUMENTS

DE 4306184 A1 * 9/1994 ............ G01N 35/08
WO WO-2024056439 A1 * 3/2024 ............ G16C 20/30
WO WO-2024196351 A1 * 9/2024 .......... B01F 35/2131
WO WO-2024238360 A2 * 11/2024 ............ G06Q 50/04
WO WO-2024238361 A2 * 11/2024 ............ G06F 30/27
WO WO-2025189301 A1 * 9/2025 ............ G16C 60/00

OTHER PUBLICATIONS

WO-2024238361-A2_translated (Year: 2024).*
WO-2024056439-A1_translated (Year: 2024).*
WO-2024238360-A2_translated (Year: 2024).*
WO-2025189301-A1_translated (Year: 2025).*
DE-4306184-A1_translated (Year: 1994).*
WO-2024196351-A1_translated (Year: 2024).*

* cited by examiner

*Primary Examiner* — Catherine T. Rastovski
*Assistant Examiner* — Michael J Singletary
(74) *Attorney, Agent, or Firm* — CALDWELL LLC

(57) ABSTRACT

A system for determining beverage compositions for aluminum can packaging. The system includes at least a processor and a memory communicatively connected to the at least a processor. The memory contains instructions configuring the at least a processor to receive a beverage composition profile including a plurality of chemical parameters associated with a beverage composition, and define, for the beverage composition profile, a composition adjustment threshold corresponding to a maximum permissible deviation for each of the plurality of chemical parameters. The processor is additionally configured to simulate, using a predictive compatibility model and for each of a plurality of candidate liner compositions, a packaging stability outcome as a function of the composition adjustment threshold, and determine, for each candidate liner composition of the plurality of candidate liner compositions, a liner compatibility score.

20 Claims, 28 Drawing Sheets

Supplemental Table 1 Initial composition of wines used in long-term canning study. TA, titratable acidity; ABV, alcohol by volume.

| Wine | Vintage | Composition | Alcohol (% ABV) | TA (g/L) | pH | Residual sugar (g/L) | Free $SO_2$ (mg/L) | $mSO_2$ (mg/L)[a] | Aluminum (mg/L) | Free $SO_2$ (mg/L): Treatment II and III | $mSO_2$ (mg/L): Treatment II | $mSO_2$ (mg/L): Treatment III |
|---|---|---|---|---|---|---|---|---|---|---|---|---|
| Pinot grigio | 2021 | 100% Pinot grigio | 12.1% | 6.7 | 3.37 | 0.0 | 16 | 0.59 | 1.17 | 39 | 1.40 | 0.58 |
| Sauvignon blanc | 2021 | 100% Sauvignon blanc | 12.1% | 7.40 | 3.28 | 1.2 | 15 | 0.68 | 1.15 | 35 | 1.58 | 0.67 |
| French rosé | 2019 | 60.2% Grenache noir; 26.5% Syrah; 8% Carignon; 5% Grenache blanc; 0.3% Ugni blanc | 12.7% | 6.10 | 3.30 | 0.6 | 21 | 0.93 | 1.16 | 51 | 2.28 | 0.57 |
| Sparkling rosé | NV | 90% Glera, 10% Pinot noir | 11.2% | 5.79 | 3.20 | 9.5 | 20.5 | 1.07 | 0.61 | 45 | 2.36 | 0.72 |
| Sparkling white | NV | 100% Glera | 10.5% | 5.60 | 3.11 | 10.9 | 15 | 0.93 | 1.11 | 41 | 2.49 | 0.69 |

[a] $mSO_2$, molecular $SO_2$, calculated from pH and free $SO_2$ using alcohol-adjusted acid dissociation constant ($pK_a$) values.

FIG. 11

Supplemental Table 2 Parameters for open circuit potential testing.

| **Pretreatment settings** | |
|---|---|
| E condition 1 | 0 V |
| t condition 1 | 0 sec |
| E condition 2 | 0 V |
| t condition 2 | 0 sec |
| **Corrosion potential settings** | |
| t interval | 1 sec |
| t run | 3600 sec |

FIG. 12A

Supplemental Table 3 Parameters for electrochemical impedance spectroscopy testing. OCP, open circuit potential; DC, direct current; AC, alternating current.

| | |
|---|---|
| **Pretreatment settings** | |
| E condition 1 | 0 V |
| t condition 1 | 0 sec |
| E condition 2 | 0 V |
| t condition 2 | 0 sec |
| **Impedance spectroscopy settings** | |
| t equilibration | 0 sec |
| Scan type | Fixed |
| E DC | 0 V |
| E AC | 0.01 V |
| Frequency type | Scan |
| n frequencies | 67 |
| Max frequency | 50,000 Hz |
| Min frequency | 0.01 Hz |
| Measure versus OCP | Checked |
| E DC versus OCP | Checked |
| t max OCP | 5 sec |
| Stability criterion | 0.1 mV/sec |
| t min sampling | 0.1 sec |
| t max equilibration | 0.01 sec |

FIG. 12B

SYSTEMS FOR AND METHODS OF DETERMINING BEVERAGE COMPOSITIONS FOR ALUMINUM CAN PACKAGING

FIELD OF THE INVENTION

The present invention generally relates to the field of food and beverage technology. In particular, the present invention is directed to systems for and methods of determining beverage compositions for aluminum can packaging.

BACKGROUND

Aluminum cans are increasingly used for packaging a wide variety of liquid formulations, including wines, seltzers, and functional beverages. However, variations in beverage chemistry, such as pH, sulfur dioxide content, dissolved oxygen levels, and trace metal concentrations, can cause unpredictable interactions with internal can liners. These interactions often lead to chemical instability, corrosion, or off-flavor development that compromise product quality and shelf life. Conventional testing methods rely on iterative physical trials that are time-consuming, costly, and inconsistent across liner types and beverage profiles. As a result, there remains a need for improved systems to address these challenges.

SUMMARY OF THE DISCLOSURE

In some aspects, the techniques described herein relate to a system for determining beverage compositions for aluminum can packaging, the system including at least a processor and a memory communicatively connected to the at least a processor, wherein the memory contains instructions configuring the at least a processor to receive a beverage composition profile including a plurality of chemical parameters associated with a beverage composition, define, for the beverage composition profile, a composition adjustment threshold corresponding to a maximum permissible deviation for each of the plurality of chemical parameters, wherein defining the composition adjustment threshold includes accessing a composition adjustment matrix specifying, for each chemical parameter of the plurality of chemical parameters, an upper and lower deviation limit defining the composition adjustment threshold and applying the composition adjustment matrix to the beverage composition profile to constrain simulated parameter changes within the defined upper and lower deviation limits; simulate, using a predictive compatibility model and for each of a plurality of candidate liner compositions, a packaging stability outcome as a function of the composition adjustment threshold, and determine, for each candidate liner composition of the plurality of candidate liner compositions, a liner compatibility score.

In some aspects, the techniques described herein relate to a method of determining beverage compositions for aluminum can packaging, the method including receiving, by at least a processor, a beverage composition profile including a plurality of chemical parameters associated with a beverage composition, defining, using the at least a processor and for the beverage composition profile, a composition adjustment threshold corresponding to a maximum permissible deviation for each of the plurality of chemical parameters, wherein defining the composition adjustment threshold includes: accessing a composition adjustment matrix specifying, for each chemical parameter of the plurality of chemical parameters, an upper and lower deviation limit defining the composition adjustment threshold and applying the composition adjustment matrix to the beverage composition profile to constrain simulated parameter changes within the defined upper and lower deviation limits, simulating, using the at least a processor and a predictive compatibility model and for each of a plurality of candidate liner compositions, a packaging stability outcome as a function of the composition adjustment threshold, and determining, using the at least a processor and for each candidate liner composition of the plurality of candidate liner compositions, a liner compatibility score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 11 is a table illustrating initial composition of wines used in a long-term canning study;

FIG. 12A, is a table of parameters for open circuit potential testing;

FIG. 12B is a table of parameters for electrochemical impedance spectroscopy testing;

Figure 1:
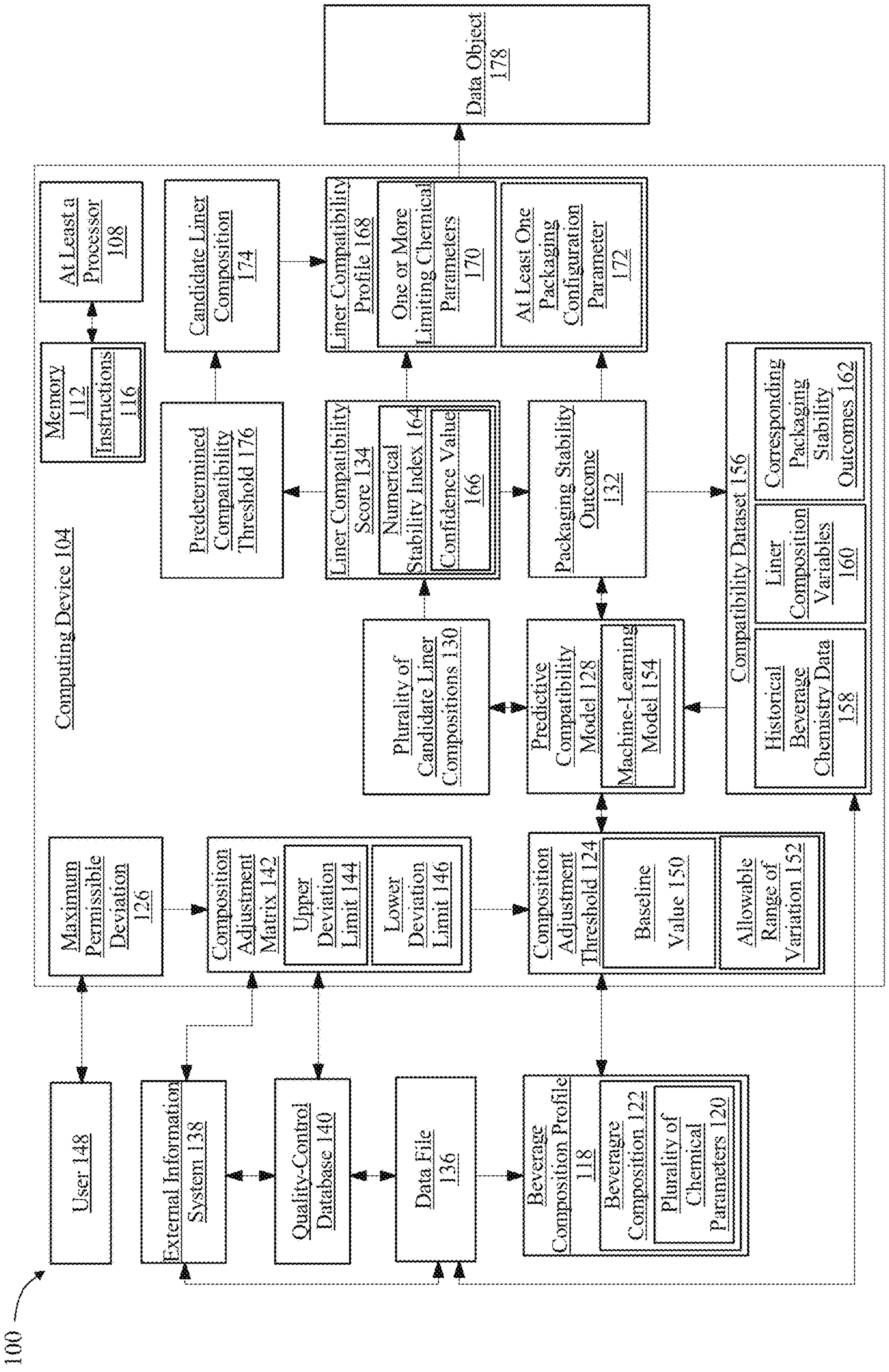
FIG. 1 is a block diagram illustrating an exemplary system for determining beverage compositions for aluminum can packaging.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments of the present disclosure relate to the technical challenge of determining whether a particular liquid formulation, such as wine, functional beverages, or THC-infused seltzers, can retain its chemical stability and sensory integrity when packaged in aluminum containers. In an embodiment, the disclosed systems and methods utilize analytical formulation data, including parameters such as pH, sulfur dioxide concentration, titratable acidity, and dissolved oxygen, in conjunction with a predictive modeling framework configured to evaluate liner-formulation compatibility and identify necessary formulation refinements. In an embodiment, the system may produce a formulation compatibility profile optimized for successful canning, thereby enabling efficient evaluation of new product concepts and minimizing reliance on empirical trial-and-error during production.

At a high level, aspects of the present disclosure are directed to systems and methods for determining formulation-liner compatibility for liquid formulations intended for aluminum can packaging. In an embodiment, the system receives a formulation profile corresponding to a specific liquid composition, defines permissible chemical adjustment thresholds, and simulates packaging stability across a plurality of liner compositions to generate a compatibility profile and associated packaging specifications.

Aspects of the present disclosure can be used to evaluate the packaging stability of a given formulation prior to canning and to identify which liner compositions are most suitable for that formulation. Aspects of the present disclosure can also be used to assess how formulation adjustments within allowable sensory or regulatory limits affect liner compatibility outcomes. This is so, at least in part, because the disclosed system models chemical interactions between beverage components and liner materials as a function of measured formulation parameters and corresponding adjustment thresholds, providing predictive insight into long-term stability without requiring iterative physical testing.

Aspects of the present disclosure allow for predictive screening of liner options and formulation adjustments, reducing experimental trial time, minimizing product loss, and improving packaging reliability across diverse beverage categories. Exemplary embodiments illustrating aspects of the present disclosure are described below in the context of several specific examples. Exemplary embodiments illustrating aspects of the present disclosure are described below in the context of several specific examples.

Embodiments of the present disclosure may provide a computational system configured to predict and optimize the compatibility between a liquid formulation and aluminum can liner compositions. In an embodiment, the system may receive analytical data defining the formulation's chemical profile, apply predefined or user-specified adjustment thresholds, and execute predictive simulations across multiple liner configurations using a compatibility modeling framework. Through this process, the system may generate quantitative compatibility scores and corresponding packaging specifications that indicate which liner compositions can maintain product stability within acceptable formulation tolerances. By automating this compatibility analysis, the disclosed systems and methods may provide a reliable, data-driven approach for selecting packaging configurations and guiding formulation refinement prior to canning.

In one or more embodiments, a technical improvement is provided by enabling a predictive and data-driven approach to determining formulation-liner compatibility without reliance on destructive, iterative physical testing. By integrating measured beverage chemistry with simulation-based modeling, the disclosed systems and methods improve computational efficiency, reproducibility, and precision in predicting long-term packaging stability outcomes. A further technical improvement is provided by introducing parameterized adjustment thresholds, which constrain the model to operate within chemically and sensorially meaningful ranges, thereby enhancing model accuracy and ensuring that simulations reflect production-feasible conditions. In some embodiments, another technical improvement arises from the use of machine-learning architectures trained on compatibility datasets containing beverage chemistry, liner material properties, and observed stability outcomes, which enable non-linear inference and adaptive learning across beverage categories. Additional improvements are provided through the system's ability to execute real-time simulations that reduce production downtime, dynamically update liner recommendations, and generate actionable compatibility profiles. Still further technical improvements are achieved through privacy-preserving configurations, which may allow processors to generate and share correlation structures without exposing proprietary formulation data, ensuring secure, distributed model learning across producers. In other embodiments, technical improvements may include increased accuracy of corrosion prediction through hybrid data-analytical modeling, improved interpretability of results using aggregated stability indices, and reduced computational overhead through parallelized simulation engines. Other technical improvements are provided throughout this disclosure and will be readily recognized by one of ordinary skill in the art in view of the embodiments described herein.

Referring now to FIG. 1, an exemplary embodiment of system 100 for determining beverage compositions for aluminum can packaging is illustrated. For purposes of this disclosure, the term "aluminum can packaging" refers to a container system formed primarily from metallic materials and configured to store, preserve, and transport liquid compositions under sealed conditions. In an embodiment, aluminum can packaging may include one or more components such as a can body, can end (or lid), and an optional internal liner. The can body may be fabricated from aluminum alloys such as 3000-series (e.g., 3004 or 3104) alloys containing aluminum with controlled proportions of manganese (Mn) and magnesium (Mg) to enhance formability, corrosion resistance, and strength. In some embodiments, the can end may be composed of 5000-series aluminum alloys (e.g., 5182 or 5052), which contain elevated levels of magnesium to provide additional rigidity and resistance to deformation under pressure. In alternate embodiments, the can may incorporate multi-metallic compositions or hybrid alloys, such as aluminum-steel laminates or aluminum-zinc-magnesium alloys, which provide tailored strength-to-weight ratios and corrosion profiles suitable for high-acid beverages. Other metal compositions may include trace elements such as silicon, copper, chromium, and/or iron, depending on the forming process and intended use.

With further reference to FIG. 1, in an embodiment, the can body may vary in size and volume capacity, including but not limited to slim, sleek, or standard profiles such as 202/211 formats (approximately 355 mL), 204/211 formats (approximately 250 mL), and/or 202/204 formats (approximately 200-250 mL). Wall thicknesses may range, without limitation, from 0.20 mm to 0.28 mm, while can ends may have a thickness in the range of 0.25 mm to 0.35 mm, depending on product pressure requirements and structural design.

Still referring to FIG. 1, in an embodiment, to prevent direct contact between the beverage and the metal surface, the interior of the aluminum can packaging may include a liner. For purposes of this disclosure, the term "liner" (also referred to as "interior coating," "lacquer," or "varnish") refers to a continuous or semi-continuous film applied to the inner surface of the can body and/or lid. In some embodiments, the liner may be composed of epoxy-based polymers, such as bisphenol A (BPA) epoxy or bisphenol A-non-intent (BPA-NI) epoxy, which may utilize alternative monomers such as tetramethyl bisphenol F (TMBPF) or bisphenol S. In other embodiments, the liner may comprise acrylic, polyester, oleoresin, phenolic, or polyolefin-based materials. In certain configurations, the liner may be applied as a single continuous layer across the interior surface, while in other embodiments, it may be implemented as multiple functional sub-layers, each tuned for different performance criteria (e.g., a primer layer for adhesion, a barrier layer for corrosion protection, and an interface layer for sensory neutrality). In some embodiments, the liner may also exhibit variable thickness across regions of the can body or lid (e.g., dome, sidewall, neck, or flange regions), typically ranging from 2 μm to 10 μm, to accommodate stress gradients or product reactivity zones. In yet other embodiments, the liner may be configured as a composite or hybrid coating, wherein a polymeric base material is reinforced with nanoparticles (e.g., silica, titanium dioxide, or graphene oxide) to enhance chemical resistance or mechanical durability. Alternatively, the liner may include cross-linked or UV-cured coatings, enabling rapid production and improved structural uniformity. Through such non-limiting configurations, the aluminum can packaging system disclosed herein may provide a controlled environment for beverage preservation while minimizing corrosion, flavor migration, and interaction between beverage constituents and metal surfaces.

In continued reference to FIG. 1, in an embodiment, system 100 may include circuitry such as, without limitation, at least a processor 108 communicatively connected to a memory 112 containing instructions 116 configuring at least a processor 108 to initiate one or more tasks as described throughout this disclosure; for instance, circuitry may include and/or be included in a computing device 104. As used in this disclosure, "communicatively connected" means connected by way of a connection, attachment, or linkage between two or more relata such as without limitation electronic components, modules, and/or devices which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Circuitry may alternatively or additionally be implemented by configuring a hardware device such as a combinatorial or sequential logic circuit, an application-specific integrated circuit (ASIC), a field-programmable gate array (FPGA), or other hardware unit; memory may be attached thereto to further configure the hardware unit using read-only memory (ROM) or any other static or writable memory as described in this disclosure. Alternatively or additionally, hardware units and/or modules may be combined with and/or in communication with a processor, such as without limitation in a system-on-chip architecture wherein some functions are configured by modification or design of hardware circuitry, such as without limitation FPGA circuitry, while others are configured in the form of instructions in memory for one or more processors. As a non-limiting example, any step or combination of steps described herein may be performed entirely using hardware circuit configured to perform such steps either with static memory or rewritable memory. Such steps or combinations of steps may include signing with a digital signature, cryptographically hashing, evaluation of zero-knowledge proofs, or any other specific process described in this disclosure.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

In continued reference to FIG. 1, in an embodiment, at least a processor 108 may be configured to receive a beverage composition profile 118 including a plurality of chemical parameters 120 associated with a beverage composition 122. For purposes of this disclosure, a "beverage composition profile" is a structured dataset that characterizes a specific liquid formulation intended for packaging. In an embodiment, the beverage composition profile 118 may include numerical, categorical, and/or metadata fields representing the analytical and compositional attributes of the beverage. Examples of such attributes may include, but are not limited to, pH, titratable acidity, free and molecular sulfur dioxide ($SO_2$), dissolved oxygen ($dO_2$), copper and/or other trace metal concentrations, and/or alcohol by volume (ABV). For purposes of this disclosure, a "chemical parameter" is a quantifiable variable describing a measurable chemical or physicochemical property of the beverage composition 122. Non-limiting examples of chemical parameters may include ionic strength, redox potential, sugar concentration, volatile sulfur compounds, and/or total phenolic content. In an embodiment, each chemical parameter may be associated with a defined unit of measure, an analytical uncertainty, and/or a corresponding reference or target range derived from formulation specifications or regulatory requirements. For purposes of this disclosure, a "beverage composition" is a liquid formulation including one or more dissolved, suspended, or emulsified components that collectively define the sensory and chemical characteristics of the final product. Non-limiting examples of beverage composition 122 may include wine, hard seltzer, THC-infused beverages, functional drinks, and/or other ready-to-drink (RTD) formulations.

In further reference to FIG. 1, in an embodiment, the beverage composition profile 118 may serve as the analytical foundation for predictive modeling and compatibility analysis. The received profile may provide baseline data, from which system 100 may determine allowable adjustment thresholds and evaluates interactions between the beverage and multiple candidate liner compositions 174. In an exemplary implementation, at least a processor 108 may receive the beverage composition profile 118 as a structured data object 178 (e.g., JSON, XML, or CSV format) transmitted using an interface module from a laboratory analysis subsystem. In an embodiment, at least a processor 108 may parse and normalize each chemical parameter, perform validation routines to confirm data integrity, and serialize the resulting feature vector for ingestion by the predictive compatibility model 128.

With continued reference to FIG. 1, in an embodiment, the beverage composition profile 118 may be received from a data file 136 uploaded from one or more of an external information system 138 and a quality-control database 140. For purposes of this disclosure, a "data file" is a structured object containing analytical or process data associated with a beverage composition 122. In an embodiment, the data file 136 may include one or more fields representing chemical parameters, measurement units, metadata (such as batch identifiers, timestamp, and instrument source), and any associated quality flags or validation indicators. Non-limiting examples of suitable data files 136 may include comma-separated value (CSV) files exported from laboratory instruments, JavaScript Object Notation (JSON) records transmitted through an application programming interface (API), and/or Extensible Markup Language (XML) documents retrieved from a networked database. For purposes of this disclosure, an "external information system" is a digital environment or software platform external to the disclosed system that maintains beverage formulation or analytical data relevant to packaging compatibility. Non-limiting examples may include laboratory information management systems (LIMS), production control servers, sensor networks monitoring process conditions, and/or third-party analytical databases that aggregate compositional metrics across multiple production sites. For purposes of this disclosure, a "quality-control database" is an internal or cloud-hosted data repository configured to store verified chemical, physical, or sensory test results associated with beverage production. In an embodiment, a quality-control database 140 may contain batch-level records of pH, dissolved oxygen, and sulfur dioxide measurements, as well as results from visual inspections, panel evaluations, and/or retention sample analyses.

With further reference to FIG. 1, in an embodiment, the data file 136 may function as the carrier for standardized analytical information, while the external information system 138 and quality-control database 140 may serve as trusted sources from which verified composition profiles are obtained. By receiving the beverage composition profile 118 from these systems, the disclosed platform may ensure that the analytical data used for predictive modeling reflects real, production-grade measurements rather than manually entered or estimated values. In an exemplary embodiment, at least a processor 108 may be configured to authenticate the source of the data file 136 through digital signature verification, parse the file structure to confirm schema compliance, and extract the analytical fields defining the beverage composition profile 118. The extracted data may then be serialized and stored within a local or distributed data repository, where it is indexed by batch identifier and timestamp to support traceability. In an embodiment, the ingestion module may further log file provenance and checksum values to maintain data integrity prior to processing by the predictive compatibility model 128.

Still referring to FIG. 1, in an embodiment, the beverage composition profile 118 may be received through automated synchronization between the disclosed system and one or more external information systems 138 or quality-control databases 140. For purposes of this disclosure, "automated synchronization" refers to a recurring or continuous data exchange process that ensures analytical and compositional information remains current without manual user intervention. In an embodiment, automated synchronization may be performed through scheduled API polling, message-based event triggers, and/or live data streaming protocols such as MQTT or WebSocket. Each synchronization event may include authentication of the transmitting source, verification of schema conformity, and timestamp-based reconciliation to prevent overwriting of historical data. In an embodiment, at least a processor 108 may further perform delta comparison operations to detect changes between previously ingested and newly received beverage composition profiles 118. In this manner, system 100 may maintain an evolving dataset of analytical results, enabling predictive modeling to reflect real-time production or quality-control conditions across multiple facilities or production lines.

In further reference to FIG. 1, in some embodiments, the beverage composition profile 118 may also be generated by a user 148 through a data-entry interface associated with system 100. For purposes of this disclosure, a "user-generated composition profile" is a profile created through manual input, graphical user interface interaction, or form-based data submission, rather than automated ingestion from an external source. In an embodiment, the user interface may allow selection or entry of chemical parameters such as pH, dissolved oxygen, sulfur dioxide, or copper content, as well as metadata including batch identifiers, product type, or formulation stage. In an embodiment, the interface may further include validation routines configured to flag incomplete entries, out-of-range parameter values, and/or unit inconsistencies before submission. Upon completion, at least a processor 108 may format the entered values into a structured beverage composition profile 118 and append a user identifier, entry timestamp, and version tag to maintain traceability. In some implementations, system 100 may integrate user-generated profiles with profiles received from external databases, thereby allowing producers to model hypothetical or in-development formulations using the same predictive compatibility framework applied to production-grade data.

With further reference to FIG. 1, in an embodiment, at least a processor 108 may be configured to define, for the beverage composition profile 118, a composition adjustment threshold 124 corresponding to a maximum permissible deviation 126 for each of the plurality of chemical parameters 120. For purposes of this disclosure, a "composition adjustment threshold" is a quantitative boundary or constraint that specifies the allowable degree of change in a given chemical parameter while maintaining compliance with desired sensory, regulatory, or stability criteria. In an embodiment, the composition adjustment threshold 124 may establish the permissible range within which the beverage formulation may be modified without adversely affecting product quality or packaging compatibility outcomes. Non-limiting examples of composition adjustment thresholds may include: a ±0.1 pH unit change around a measured baseline, a ±5 mg/L variation in free sulfur dioxide, or a ±10% deviation in titratable acidity. For purposes of this disclosure, a "maximum permissible deviation" is a parameter-specific value representing the upper bound of allowable variation for a corresponding chemical parameter. In an embodiment, the maximum permissible deviation 126 may be defined by product specifications, regulatory tolerances, sensory limits, and/or manufacturer-set consistency requirements. For example, a winemaker may define a maximum permissible deviation 126 of ±2 mg/L for dissolved oxygen to preserve flavor integrity, whereas a producer of carbonated beverages may define ±15% dissolved $CO_2$ variability to maintain effervescence.

In continued reference to FIG. 1, in an embodiment, defining the composition adjustment threshold 124 may enable the predictive compatibility model 128 to simulate packaging performance under realistic formulation constraints. By constraining parameter variation to predetermined limits, the model can evaluate liner-formulation interactions without producing nonviable or out-of-specification formulations. In an exemplary implementation, at least a processor 108 may retrieve stored product or category-level deviation limits from a configuration database, normalize the values according to the measurement units of each corresponding chemical parameter, and associate these limits with the active beverage composition profile 118. The resulting set of thresholds may be serialized as a structured data layer, such as a "composition adjustment matrix," that defines the permissible bounds for subsequent stability simulations.

In further reference to FIG. 1, in an embodiment, defining the composition adjustment threshold 124 may include accessing a composition adjustment matrix 142 specifying, for each chemical parameter of the plurality of chemical parameters 120, an upper and lower deviation limit 146 defining the composition adjustment threshold 124. For purposes of this disclosure, a "composition adjustment matrix" is a structured data object 178, table, or relational dataset that maps each chemical parameter in the beverage composition profile 118 to its corresponding range of permissible variation. In an embodiment, the composition adjustment matrix 142 may function as a reference framework that consolidates parameter-specific boundaries for formulation adjustment and predictive modeling. Each record or row of the composition adjustment matrix 142 may correspond to a distinct chemical parameter, while associated fields may include parameter name, baseline value, upper deviation limit 144, lower deviation limit 146, unit of measure, and threshold source (e.g., regulatory, sensory, or production-based). For purposes of this disclosure, an "upper deviation limit" is the maximum positive offset permitted for a given chemical parameter relative to its baseline value. In an embodiment, the upper deviation limit 144 may represent the largest permissible increase in the magnitude of a measured or simulated parameter before it exceeds the established composition adjustment threshold 124. Non-limiting examples of upper deviation limits 144 may include a +0.2 pH increase, a +10 mg/L increase in free $SO_2$, or a +5% rise in dissolved oxygen. For purposes of this disclosure, a "lower deviation limit" is the maximum negative offset permitted for a given chemical parameter relative to its baseline value. In an embodiment, the lower deviation limit 146 may represent the largest permissible decrease in the magnitude of a measured or simulated parameter before it falls below the established composition adjustment threshold 124. Non-limiting examples of lower deviation limits 146 may include a −0.2 pH decrease, a −5 mg/L reduction in free $SO_2$, or a −3% reduction in titratable acidity.

With continued reference to FIG. 1, in an embodiment, the composition adjustment matrix 142 may provide a dynamic boundary condition that informs how the predictive compatibility model 128 perturbs formulation variables during simulation. By explicitly defining upper and lower deviation limits 146 for each parameter, system 100 may ensure that the modeled adjustments reflect realistic production tolerances and maintain chemical plausibility. In an exemplary embodiment, at least a processor 108 may access the composition adjustment matrix 142 from a configuration datastore, local cache, or remote database. In an embodiment, the composition adjustment matrix 142 may be stored as a tabular dataset (e.g., SQL table), a multidimensional array, and/or a JSON object encoded within a configuration file. At least a processor 108 may, in some cases, query the composition adjustment matrix 142 using parameter identifiers derived from the beverage composition profile 118, retrieve the associated deviation limits, and temporarily store the data in volatile memory for use during compatibility simulations. In some embodiments, the composition adjustment matrix 142 may be version-controlled, allowing system 100 to trace historical threshold sets or apply product-specific adjustment rules across different beverage categories.

Still referring to FIG. 1, in an embodiment, defining the composition adjustment threshold 124 may include applying the composition adjustment matrix 142 to the beverage composition profile 118 to constrain simulated parameter changes within the defined upper deviation limit 144 and lower deviation limit 146. In an embodiment, "applying the composition adjustment matrix" may refer to a computational operation in which at least a processor 108 overlays, merges, or otherwise associates the deviation limits defined in the composition adjustment matrix 142 with the corresponding chemical parameters within the beverage composition profile 118. This operation may establish a parameter-bound simulation domain that restricts all subsequent virtual or algorithmic adjustments to remain within the defined tolerance ranges. In an embodiment, "constraining simulated parameter changes" may refer to limiting the numerical perturbations applied to chemical parameters during predictive modeling such that any simulated variation respects the established upper deviation limit 144 and lower deviation limit 146. This may ensure that the simulated conditions evaluated by the predictive compatibility model 128 remain chemically plausible, production-feasible, and compliant with regulatory and sensory requirements.

With further reference to FIG. 1, in an embodiment, the application of the composition adjustment matrix 142 may transform the beverage composition profile 118 from a static analytical dataset into a parameterized model-ready input. In an embodiment, the modified profile may thus incorporate both baseline values and allowable variation bands for each chemical parameter, which may serve as input boundaries for subsequent simulations predicting liner compatibility or packaging stability. By enforcing these limits, system 100 may avoid generating out-of-specification predictions that could otherwise yield inaccurate or non-actionable results. In an exemplary embodiment, at least a processor 108 may perform this application step by executing a parameter-binding routine that maps each chemical parameter to its corresponding deviation bounds. At least a processor 108 may then instantiate simulation vectors where each element represents a possible formulation state within the defined range. In an embodiment, these simulation vectors may be generated using sampling techniques such as Latin hypercube sampling, Monte Carlo perturbation, and/or bounded randomization. The predictive compatibility model 128 may then process each vector to estimate expected liner-formulation interaction outcomes under permissible adjustment conditions. In some embodiments, system 100 may dynamically adjust these bounds in real-time based on user feedback and/or historical stability data, thereby refining predictive accuracy over iterative simulations.

In continued reference to FIG. 1, in an embodiment, defining the composition adjustment threshold 124 may include receiving, from a user 148, the maximum permissible deviations 126 for each of the plurality of chemical parameters 120. For purposes of this disclosure, a "user" is any authorized individual, operator, or system agent capable of providing input data to configure or refine the operation of the system. Non-limiting examples of users 148 may include beverage producers, formulation chemists, quality-control specialists, and/or research and development personnel responsible for specifying product tolerances or testing parameters. In some embodiments, a user 148 may also include an automated software client, such as an enterprise resource planning (ERP) integration module and/or a digital twin interface configured to submit configuration data programmatically. In an embodiment, "receiving, from a user 148, the maximum permissible deviations" may refer to an interaction in which system 100 acquires one or more numerical or categorical values defining the allowable degree of variation for each chemical parameter within the beverage composition profile 118. In an embodiment, the user 148 may specify these values directly through a graphical user interface, a configuration file upload, and/or a remote API call. Each received deviation value may correspond to a particular analytical parameter (e.g., ±0.1 pH, ±5 mg/L free $SO_2$, ±10% titratable acidity) and may be entered individually or as part of a batch configuration profile. In an embodiment, user-specified maximum permissible deviations 126 may serve as a manual override or supplement to the automatically retrieved limits contained within the composition adjustment matrix 142. This functionality may allow formulation experts to tailor simulation boundaries to unique product lines, regulatory constraints, and/or experimental conditions. By receiving these inputs directly from the user 148, system 100 may enable adaptive threshold definition, ensuring that predictive modeling aligns with both standard operational tolerances and situational requirements. In an exemplary embodiment, at least a processor 108 may present a configuration interface through which the user 148 can view and modify default deviation values for each chemical parameter. Upon submission, at least a processor 108 may validate the received inputs by checking for numeric format compliance, acceptable unit consistency, and logical range alignment with baseline values. In an embodiment, the validated deviation inputs may then be appended to or replace entries within the active composition adjustment matrix 142. In some implementations, system 100 may store these user-defined deviations with associated metadata, including user credentials, timestamps, and applied formulation identifiers, to preserve traceability and enable audit-ready documentation of configuration changes.

With further reference to FIG. 1, in an embodiment, defining the composition adjustment threshold 124 may include appending the maximum permissible deviation 126 for each of the plurality of chemical parameters 120 to the beverage composition profile 118. For purposes of this disclosure, "appending" refers to a data operation in which one or more additional data fields, records, or metadata values are programmatically linked to an existing dataset or object without altering its original contents. In an embodiment, appending the maximum permissible deviation 126 may include extending the beverage composition profile 118 to include new fields representing the upper and lower tolerance values associated with each chemical parameter. This process may effectively merge user-defined or system-defined threshold data into the analytical structure of the beverage composition profile 118, enabling unified access during subsequent modeling operations. In an embodiment, the maximum permissible deviation 126 appended to the beverage composition profile 118 may be represented as a pair of numerical values corresponding to an upper and lower limit for each chemical parameter, expressed in the same measurement unit as the baseline parameter value. Each appended deviation may include metadata such as data source (e.g., user-defined or matrix-derived), timestamp, and validation status, ensuring that every threshold is both traceable and contextually interpretable during simulation.

With continued reference to FIG. 1, in an embodiment, appending the maximum permissible deviations 126 may transform the beverage composition profile 118 from a static analytical dataset into a constraint-aware formulation model. This augmented profile may enable the predictive compatibility model 128 to evaluate liner-formulation stability using real, bounded parameter ranges rather than unconstrained variable inputs. In this manner, system 100 may preserve the integrity of the baseline analytical data while layering additional information necessary for predictive evaluation and optimization. In an exemplary embodiment, at least a processor 108 may implement this operation through a structured data-binding routine that aligns each chemical parameter with its corresponding maximum permissible deviation 126. The resulting augmented beverage composition profile 118 may be serialized as a structured object (e.g., JSON, HDF5, or SQL record) containing nested fields for baseline value, unit, deviation limits, and data source metadata. In an embodiment, at least a processor 108 may store the appended profile within a configuration data repository or transient cache, where it serves as the input to the predictive compatibility model 128. In some embodiments, version control mechanisms may be applied so that each appended or modified threshold is logged with revision identifiers, allowing historical reconstruction of simulation configurations over time.

Still referring to FIG. 1, in an embodiment, defining the composition adjustment threshold 124 may include identifying, for each chemical parameter of the plurality of chemical parameters 120, a baseline value 150 as a function of a measured condition of the beverage composition 122. For purposes of this disclosure, a "baseline value" is the initial, experimentally determined, or otherwise verified quantitative measurement associated with a given chemical parameter prior to any modeled or simulated adjustment. In an embodiment, the baseline value 150 may establish the reference point from which permissible deviations are calculated and against which simulated variations are compared. Non-limiting examples of baseline values 150 may include a measured pH of 3.42, a free sulfur dioxide concentration of 28 mg/L, a dissolved oxygen level of 0.8 mg/L, or a titratable acidity of 6.0 g/L expressed as tartaric acid equivalents. In some embodiments, the baseline value 150 may represent an average of multiple readings from a single production batch or may be derived from laboratory testing results stored within a quality-control database 140. For purposes of this disclosure, a "measured condition" is an empirically observed or instrument-detected state of the beverage composition 122 obtained through direct analysis or sensor measurement. In an embodiment, measured conditions may include physical, chemical, and/or electrochemical parameters recorded under defined sampling protocols or environmental conditions. Non-limiting examples of measured conditions include temperature, dissolved oxygen concentration, total pressure, electrical conductivity, and/or redox potential at the time of measurement. In an embodiment, a measured condition may further include metadata such as date, instrument type, calibration status, and sample identifier, ensuring traceability and reproducibility of analytical results.

In continued reference to FIG. 1, in an embodiment, the baseline value 150 may provide the quantitative foundation for establishing composition adjustment thresholds 124. By defining allowable deviations relative to empirically measured conditions, system 100 may ensure that all subsequent simulations and compatibility evaluations reflect the actual formulation state rather than nominal or theoretical values. This approach may enable the predictive compatibility model 128 to more accurately replicate real-world packaging interactions and stability behaviors. In an exemplary embodiment, at least a processor 108 may be configured to retrieve analytical readings for each chemical parameter from the beverage composition profile 118, compute baseline values 150 using aggregation functions such as mean, median, or weighted average, and normalize the results to a consistent unit system. In an embodiment, at least a processor 108 may then associate each baseline value 150 with its corresponding measured condition metadata and store the resulting set of values as a reference table within volatile memory or a configuration cache. In some embodiments, system 100 may further apply filtering algorithms to exclude anomalous readings, such as outlier values detected through z-score analysis or instrument error flags, ensuring that each baseline value 150 accurately represents a stable and validated measurement of the beverage composition 122.

With continued reference to FIG. 1, in an embodiment, defining the composition adjustment threshold 124 may include determining, for the baseline value 150, an allowable range of variation 152 as a function of the maximum permissible deviation 126. For purposes of this disclosure, an "allowable range of variation" is a continuous or discrete interval surrounding a baseline value 150 that defines the upper and lower bounds within which a corresponding chemical parameter may vary without exceeding the maximum permissible deviation 126. In an embodiment, the allowable range of variation 152 may therefore represent the operational window for simulated or real-world adjustments to the beverage composition 122. Non-limiting examples of allowable ranges of variation may include a pH range of 3.32-3.52 for a baseline pH of 3.42 and a maximum permissible deviation 126 of ±0.10, or a dissolved oxygen range of 0.6-1.0 mg/L for a baseline of 0.8 mg/L and a maximum permissible deviation 126 of ±0.2 mg/L.

In continued reference to FIG. 1, in an embodiment, the allowable range of variation 152 may be expressed numerically as: $R_i=[B_i-\Delta_i, B_i+\Delta_i]$ where $R_i$ denotes the allowable range of variation 152 for a given parameter i, $B_i$ represents the baseline value 150, and $\Delta_i$ corresponds to the maximum permissible deviation 126. In some embodiments, the range may be represented as absolute values (e.g., ±5 mg/L) or as percentage-based deviations (e.g., ±10% of baseline), depending on the sensitivity of the parameter or the analytical reporting standard.

With further reference to FIG. 1, in an embodiment, determining the allowable range of variation 152 may enable the predictive compatibility model 128 to establish a bounded solution space for each chemical parameter. These defined ranges may allow system 100 to test multiple simulated formulations within realistic tolerance limits, ensuring that predictive results remain representative of feasible adjustments achievable in production environments. In an embodiment, the allowable range of variation 152 thereby may function as both a chemical constraint and a safety boundary within the model's computational architecture. In an exemplary embodiment, at least a processor 108 may compute the allowable range of variation 152 by retrieving each baseline value 150 and corresponding maximum permissible deviation 126 from the augmented beverage composition profile 118. In an embodiment, at least a processor 108 may then calculate the upper and lower limits for each parameter and populate a new record within the composition adjustment matrix 142. In some embodiments, the computation may include conversion factors to normalize heterogeneous units (e.g., mg/L to ppm, % v/v to g/L) or apply rounding logic based on parameter precision. The resulting allowable ranges may be dynamically updated when new measurements are received and/or when a user 148 modifies the permissible deviation values, thereby ensuring that the simulation model continuously reflects the most current formulation boundaries.

In further reference to FIG. 1, in an embodiment, defining the composition adjustment threshold 124 may include mapping, for each chemical parameter of the plurality of chemical parameters 120, the allowable range of variation 152 to a corresponding chemical parameter to define the composition adjustment threshold 124. For purposes of this disclosure, "mapping" refers to a computational association process in which data elements from one dataset are programmatically linked to corresponding elements in another dataset according to a defined matching rule or index. In this context, mapping may include linking the allowable range of variation 152 for each chemical parameter to its respective identifier, data record, and/or attribute field within the beverage composition profile 118. In an embodiment, this association may form the final data structure defining the composition adjustment threshold 124 for simulation and predictive analysis. For purposes of this disclosure, a "corresponding chemical parameter" refers to the specific analytical variable within the beverage composition profile 118 that is directly linked to a given allowable range of variation 152. In an embodiment, each corresponding chemical parameter may serve as the anchor for threshold assignment and may be uniquely identified by its parameter name, data type, or identifier tag. Non-limiting examples of corresponding chemical parameters may include a pH value associated with a ±0.1 allowable range, a free sulfur dioxide ($SO_2$) concentration associated with a ±5 mg/L allowable range, and/or a dissolved oxygen ($dO_2$) measurement associated with a ±0.2 mg/L allowable range. In some embodiments, corresponding chemical parameters may also include derived or composite parameters, such as total acidity or oxidation-reduction potential, which may be calculated from multiple direct measurements.

With continued reference to FIG. 1, in an embodiment, mapping the allowable range of variation 152 to each corresponding chemical parameter may produce a unified data representation that binds the analytical measurements to their permissible adjustment limits. In an embodiment, this mapping step may convert individual parameter constraints into a cohesive threshold framework that governs the predictive compatibility model's simulation domain. As a result, system 100 may be able to apply consistent and parameter-specific constraint logic during computational modeling, ensuring that predicted liner compatibility outcomes reflect the precise formulation characteristics of the input beverage. In an exemplary embodiment, at least a processor 108 may perform this mapping operation using key-based or index-based data structures such as hash maps, relational joins, or associative arrays. In an embodiment, each chemical parameter record may be used as a lookup key, with its corresponding allowable range of variation 152 stored as a linked value or nested attribute. The resulting mapped dataset, defining the composition adjustment threshold 124, may be serialized into a machine-readable format such as JSON, Protocol Buffers, or SQL table entries for subsequent use by the predictive compatibility engine. In some embodiments, at least a processor 108 may further apply integrity checks to verify that all chemical parameters in the beverage composition profile 118 have corresponding mapped ranges, and that no range is assigned to an undefined or duplicate parameter. This may ensure both structural completeness and referential accuracy within the threshold definition process.

Still referring to FIG. 1, in an embodiment, at least a processor 108 may be configured to simulate, using a predictive compatibility model 128 and for each of a plurality of candidate liner compositions 174 130, a packaging stability outcome 132 as a function of the composition adjustment threshold 124. For purposes of this disclosure, a "predictive compatibility model" is a computational model, statistical framework, or machine-learning algorithm configured to estimate the likelihood that a particular beverage composition 122 will remain chemically and sensorially stable when stored in a specified packaging configuration. In an embodiment, the predictive compatibility model 128 may analyze the beverage composition profile 118, including chemical parameters and composition adjustment thresholds 124, together with liner composition characteristics to simulate potential interactions over time. Non-limiting examples of predictive compatibility models 128 may include regression-based predictors, gradient-boosted ensembles, neural networks trained on historical stability data, and/or hybrid simulation-analytical models that combine rule-based corrosion scoring with data-driven learning outputs. For purposes of this disclosure, a "candidate liner composition" is a distinct material or multilayer structure applied to the interior surface of an aluminum container and configured to prevent chemical interaction between the beverage and the underlying metal substrate. In an embodiment, each candidate liner composition 174 may include one or more polymeric, epoxy, or polyester layers and may vary by resin chemistry, coating thickness, curing process, and/or functional additives such as adhesion promoters and/or corrosion inhibitors. Non-limiting examples of candidate liner compositions 174 may include BPA-free epoxy coatings, polyester-based barrier systems, and/or oleoresin formulations optimized for acidic beverages, such as wine or juice, for example. For purposes of this disclosure, a "packaging stability outcome" is a predicted or measured indicator representing the extent to which a beverage composition 122 maintains its desired chemical, sensory, and visual quality during storage in contact with a given liner composition. In an embodiment, packaging stability outcomes 132 may include corrosion risk scores, color shift indices, off-odor probability estimates, metal ion leaching levels, and/or aggregate stability classifications such as "compatible," "marginal," or "incompatible."

In further reference to FIG. 1, in an embodiment, packaging stability outcomes 132 may include quantitative and/ or qualitative indicators such as corrosion risk scores, color shift indices, off-odor probability estimates, metal ion leaching levels, and/or aggregate stability classifications. For purposes of this disclosure, a “corrosion risk score” is a calculated or predicted value representing the probability or expected severity of metal substrate corrosion under defined storage conditions. In an embodiment, corrosion risk may be influenced by beverage acidity, chloride content, and liner porosity, and high corrosion risk scores may correlate with visual can pitting, liner delamination, and/or metallic off-flavors that render the product unmarketable. A “color shift index” is a metric quantifying the change in optical or chromatic properties of the beverage over time as a function of liner-beverage interaction, oxygen ingress, or pigment instability. In an embodiment, excessive color shift may indicate oxidation and/or anthocyanin degradation in wines and can be used as a proxy for both aesthetic and chemical stability. An “off-odor probability estimate” is a model-generated likelihood that undesirable volatile compounds will accumulate due to reductive or oxidative reactions facilitated by metal ions or liner degradation. In an embodiment, the emergence of off-odors can signal sensory rejection by consumers and early product spoilage. “Metal ion leaching levels,” for purposes of this disclosure, are the predicted or measured concentration of metal ions transferred from the container substrate into the beverage over time. In an embodiment, elevated leaching levels can lead to sensory defects, health concerns, and/or regulatory non-compliance and may also catalyze secondary oxidation reactions that degrade product stability.

In continued reference to FIG. 1, in an embodiment, these individual outcome metrics may contribute to a comprehensive evaluation of beverage-liner compatibility. In some embodiments, the predictive compatibility model 128 may assign weighted importance to each indicator based on beverage category, product shelf-life expectations, and/or regulatory requirements. For instance, color stability may be prioritized for wine applications, whereas corrosion risk and metal ion leaching may dominate for low-pH beverages. The resulting aggregate classification, such as “compatible,” “marginal,” or “incompatible,” thus may provide an interpretable summary of predicted performance, guiding producers toward liner selections that maintain both chemical integrity and consumer-perceived quality throughout the intended storage duration.

With further reference to FIG. 1, in an embodiment, simulating packaging stability outcomes 132 using the predictive compatibility model 128 may enable proactive identification of optimal liner compositions for a given beverage formulation. In an embodiment, at least a processor 108 may perform multiple simulations, each corresponding to a unique combination of beverage composition parameters within their allowable variation ranges and a candidate liner composition 174, thereby generating a predictive map of expected stability behavior. This simulation-driven approach may eliminate the need for extensive physical testing while maintaining a high degree of analytical precision and reproducibility. In an exemplary embodiment, at least a processor 108 may retrieve the augmented beverage composition profile 118 containing the composition adjustment thresholds 124, iterate through a set of candidate liner composition 174 records stored in a liner-library database, and execute the predictive compatibility model 128 for each combination. In an embodiment, during each simulation cycle, at least a processor 108 may apply parameter perturbations within the allowable range of variation 152 and evaluate the resulting packaging stability outcome metrics. The simulation results may be stored in a structured results table and/or multidimensional array, with each record linking a specific liner composition identifier, beverage formulation variant, and predicted stability outcome value.

In continued reference to FIG. 1, in an embodiment, the predictive compatibility model 128 may include a machine-learning model 154 that has been trained on a compatibility dataset 156 including historical beverage chemistry data 158, liner composition variables 160, and corresponding packaging stability outcomes 162. For purposes of this disclosure, a “compatibility dataset” is a collection of records linking beverage formulation characteristics, packaging material attributes, and measured or inferred packaging performance indicators. In an embodiment, each record within the compatibility dataset 156 may include feature vectors representing beverage chemistry data and liner composition variables 160, paired with labeled outputs corresponding to observed stability outcomes. In some embodiments, the compatibility dataset 156 may be assembled from laboratory trials, production-scale packaging tests, and/or archived quality-control results. The composition dataset may also include synthetic and/or augmented data generated through simulation or transfer-learning techniques to enhance model generalizability across beverage categories.

Still referring to FIG. 1, for purposes of this disclosure, “historical beverage chemistry data” refers to stored analytical measurements and compositional metadata describing previously produced or tested beverage formulations. In an embodiment, historical beverage chemistry data 158 may include time-stamped measurements of pH, titratable acidity, sulfur dioxide concentration, dissolved oxygen, metal ion content, redox potential, and/or alcohol by volume. In some embodiments, the historical beverage chemistry data 158 may also include contextual metadata such as storage temperature, packaging date, batch identifier, or beverage type (e.g., wine, seltzer, or functional beverage). This historical data may provide the empirical foundation from which the model learns correlations between chemical composition and packaging stability. For purposes of this disclosure, “liner composition variables” are the physical and chemical attributes of a given liner material that may influence beverage compatibility. Non-limiting examples of liner composition variables 160 include resin type (e.g., epoxy, polyester, or oleoresin), curing conditions, coating thickness, surface energy, additive concentration, pigment load, and/or permeability coefficient. These variables may be encoded as numerical or categorical features and may capture both bulk composition and interfacial characteristics that affect corrosion resistance and flavor neutrality. For purposes of this disclosure, “corresponding packaging stability outcomes” are the measured or classified results obtained from previous beverage-liner interaction studies. In an embodiment, these outcomes may include empirical corrosion rates, leached metal concentrations, color stability indices, sensory defect scores, and/or binary compatibility classifications such as “pass” or “fail.” In an embodiment, each outcome record may serve as a labeled target used to train the predictive compatibility model 128 to recognize how specific chemical and material configurations correlate with real-world performance.

In further reference to FIG. 1, in an embodiment, the compatibility dataset 156 may enable the predictive compatibility model 128 to infer complex, non-linear relationships between beverage composition 122 and liner properties. By training on the compatibility dataset 156, the predictive compatibility model 128 may develop the ability to predict packaging stability outcomes 132 for new or modified beverage formulations without requiring extensive physical testing. In an embodiment, system 100 may therefore identify compatibility risks or recommend suitable liners in silico, greatly reducing experimental cost and time-to-market. In an exemplary embodiment, at least a processor 108 may preprocess the compatibility dataset 156 by cleaning inconsistent entries, normalizing feature scales, and encoding categorical variables. In an embodiment, the machine-learning model 154, such as a gradient-boosted tree ensemble, convolutional neural network, or transformer architecture, may then be trained to minimize prediction error between simulated and observed stability outcomes. Cross-validation and regularization techniques may be applied to prevent overfitting, and model performance may be evaluated using metrics such as mean absolute error (MAE), F1-score, and/or area under the receiver operating characteristic curve (AUC-ROC). In an embodiment, the trained model may subsequently be serialized and stored within a model repository, where it can be accessed by the simulation engine to predict compatibility outcomes for new beverage composition profiles 118.

With continued reference to FIG. 1, for purposes of this disclosure, a "feature vector" is an ordered numerical or categorical representation of the input data describing a specific beverage composition 122 and its associated packaging configuration. In an embodiment, each feature vector may include chemical attributes derived from the beverage composition profile 118 (e.g., pH, titratable acidity, dissolved oxygen concentration, redox potential, and/or metal ion content), formulation adjustment parameters (e.g., allowable range of variation 152, maximum permissible deviation 126), and/or material descriptors corresponding to the candidate liner composition 174 (e.g., resin class, coating thickness, surface treatment type, and/or additive concentration). In some embodiments, the feature vector may further include environmental and temporal context variables such as storage temperature, humidity, and aging duration, allowing the predictive compatibility model 128 to simulate long-term packaging stability under various conditions. For purposes of this disclosure, a "simulation cycle" is a single computational iteration in which the predictive compatibility model 128 evaluates one or more feature vectors to produce predicted packaging stability outcomes 132. In an embodiment, each simulation cycle may correspond to a unique combination of beverage composition values within their allowable variation ranges and one candidate liner composition 174. The predictive compatibility model 128 may execute a plurality of simulation cycles sequentially or in parallel, thereby generating a stability landscape representing the predicted response of the beverage-liner system under multiple formulation and material scenarios.

In continued reference to FIG. 1, in an embodiment, simulation cycles may enable the predictive compatibility model 128 to comprehensively explore the feasible design space defined by the composition adjustment thresholds 124 and the set of candidate liner compositions 174. This may allow system 100 to identify combinations that exhibit optimal predicted performance and to detect conditions likely to result in corrosion, off-flavor formation, and/or other degradation pathways. In an embodiment, the simulated outputs may provide both a quantitative prediction (e.g., numerical stability index 164 or risk score) and a categorical interpretation (e.g., compatible or incompatible), which may be used to populate the liner compatibility profile 168 or guide formulation adjustments. In an exemplary embodiment, at least a processor 108 may generate a plurality of feature vectors by sampling parameter values within each chemical parameter's allowable range of variation 152. In an embodiment, the predictive compatibility model 128 may process each feature vector through a trained inference pipeline that includes data normalization, model inference, and post-processing. The output layer of the model may compute a probability distribution or scalar score representing the predicted packaging stability outcome 132 for each feature vector. In some embodiments, at least a processor 108 may apply ensemble averaging across multiple trained models to improve predictive accuracy and robustness. The simulation engine may then aggregate all results into a multidimensional matrix indexed by liner composition, chemical parameter set, and simulated outcome metric, enabling visualization or ranking of liner-formulation compatibility in subsequent stages.

Still referring to FIG. 1, in some embodiments, the predictive compatibility model 128 may operate within a simulation engine configured to orchestrate concurrent model inferences, manage data batching, and maintain synchronization between simulation cycles and output aggregation. In an embodiment, the simulation engine may allocate computing resources dynamically across processor cores or distributed compute nodes to optimize throughput for large-scale predictive analyses. In some embodiments, each simulation cycle may be executed as a discrete thread or containerized task, enabling asynchronous processing and scalable parallelization. In an embodiment, system 100 may further compute a confidence interval or uncertainty score associated with each simulated packaging stability outcome 132. In an embodiment, confidence values 166 may be derived from ensemble variance, dropout-based uncertainty sampling, and/or Bayesian posterior estimation, thereby quantifying model reliability for each beverage-liner pairing. Low-confidence predictions may trigger additional targeted simulations or user notifications indicating insufficient data coverage within the compatibility dataset 156. In some embodiments, the predictive compatibility model 128 may incorporate time-dependent modeling, wherein stability outcomes are estimated over discrete temporal intervals representing accelerated aging conditions, such as one week, one month, or six months of storage, under predefined environmental parameters. This temporal modeling capability may enable generation of degradation trajectories, including corrosion progression curves and color stability decay functions, that allow for shelf-life estimation of each beverage-liner configuration. In an embodiment, system 100 may also include a feedback retraining loop configured to compare simulated predictions with newly acquired empirical data from laboratory or production sources. When discrepancies exceed a defined error threshold, the retraining module may update the compatibility dataset 156 and reoptimize the model parameters, ensuring continuous alignment between simulation outputs and real-world performance. Following completion of all simulation cycles, system 100 may generate a compatibility visualization layer displaying predictive results through interactive charts, heatmaps, or ranked stability matrices. In an embodiment, the visualization layer may present correlations between chemical parameter variations, liner compositions, and predicted stability outcomes, providing interpretable insights that guide formulation refinement, liner selection, and production decision-making.

In further reference to FIG. 1, in some embodiments, at least a processor 108 may be configured to execute a privacy-preserving inference routine that enables iterative model learning and correlation storage without exposing proprietary beverage composition data. In an embodiment, at least a processor 108 may locally process the beverage composition profile 118 to generate an encrypted or abstracted feature representation, such as a correlation matrix, statistical embedding, or anonymized feature vector, that retains parameter relationships relevant to compatibility modeling while excluding raw concentration values or ingredient identifiers. In an embodiment, at least a processor 108 may then transmit only the derived correlation data or model gradient updates to a centralized model repository for aggregation and retraining, thereby allowing the predictive compatibility model 128 to improve collectively across multiple users without accessing the underlying formulation data. In some embodiments, at least a processor 108 may employ one or more privacy-preserving learning techniques, including homomorphic encryption, differential privacy noise injection, and/or secure multiparty computation, to ensure that transmitted correlation structures cannot be reverse-engineered to reconstruct the original beverage composition profile 118. In an embodiment, at least a processor 108 may further store the locally computed correlation representations within a secure enclave or encrypted local cache, enabling continuous on-device inference and adaptive retraining while maintaining strict data isolation between users 148. Through this configuration, system 100 may preserve confidentiality of proprietary formulations while still contributing anonymized relational data to enhance global model performance, thereby enabling collaborative model refinement across producers without compromising trade secret protection.

With further reference to FIG. 1, in some embodiments, the privacy-preserving inference routine executed by at least a processor 108 may be implemented within a distributed learning architecture comprising a plurality of client nodes, each maintaining a local instance of the predictive compatibility model 128. In an embodiment, during a training cycle, each client node may compute local gradient updates or feature-correlation matrices based on its respective beverage composition profiles 118 and transmit these updates to a central aggregation server through an encrypted communication channel. In an embodiment, the aggregation server may execute a federated averaging algorithm to update the global model parameters without receiving or reconstructing any underlying formulation data. The updated global parameters may then be redistributed to each client node, allowing each local model instance to refine its inference accuracy over successive training rounds. In some embodiments, at least a processor 108 may maintain a version-control log of local model updates and a validation cache containing anonymized performance metrics (e.g., prediction accuracy, stability error rate, or compatibility confidence interval) for use in subsequent adaptive retraining. This implementation may enhance both privacy and scalability, allowing secure, continuous model improvement across geographically distributed production sites without centralized access to confidential beverage composition data.

With continued reference to FIG. 1, in an embodiment, at least a processor 108 may be configured to determine, for each candidate liner composition 174 of the plurality of candidate liner compositions 130, a liner compatibility score 134. For purposes of this disclosure, a "liner compatibility score" is a quantitative or categorical indicator representing the predicted suitability of a particular liner composition for maintaining the chemical, physical, and sensory integrity of a beverage composition 122 over its expected shelf life. In an embodiment, the liner compatibility score 134 may be derived from one or more simulated packaging stability outcomes 132 produced by the predictive compatibility model 128, including but not limited to corrosion risk, color stability, odor formation, and metal ion migration. In some embodiments, the liner compatibility score 134 may be expressed as a normalized numerical index (e.g., 0-1 or 0-100 scale), where higher values correspond to greater predicted compatibility. In other embodiments, the liner compatibility score 134 may be expressed as a ranked or categorized output, such as "compatible," "marginal," or "incompatible," based on predefined or dynamically determined classification thresholds. In an exemplary implementation, at least a processor 108 may aggregate individual outcome metrics according to weighting factors determined by beverage type, packaging duration, and/or regulatory compliance standards, thereby computing a composite liner compatibility score 134 that integrates multiple stability indicators into a single interpretable output. In some embodiments, the liner compatibility score 134 may also encode a confidence interval or model-derived uncertainty value, indicating the statistical reliability of the compatibility prediction under the given formulation and liner parameter set.

With continued reference to FIG. 1, in an embodiment, the liner may extend over substantially the entire internal surface area of the can, including the body, neck, and dome regions. In other embodiments, the liner may be selectively applied to high-interaction regions, such as the body wall or seam areas, while omitting regions of low contact exposure. The liner may have a uniform or variable thickness profile depending on application process parameters, target beverage type, or manufacturer specifications. In an embodiment, the liner thickness may range from approximately 1 μm to 10 μm. In some embodiments, the liner thickness may be graded such that thicker coverage is present near the dome or seams, where mechanical stress and corrosion potential are greater, while thinner coverage may be used in the body to reduce weight or curing time. Non-limiting examples of liner materials may include bisphenol-A (BPA)-based epoxy resins, bisphenol-A-non-intent (BPA-NI) epoxies such as tetramethyl bisphenol F epoxies, polyester coatings, acrylic coatings, oleoresin formulations, and hybrid polymer-ceramic barrier films. In some embodiments, the liner may include a multilayer structure comprising a base polymer layer and one or more functional sub-layers such as adhesion promoters, cross-linking agents, anti-corrosion additives, pigments, or surface primers. In an embodiment, the liner material may be selected as a function of beverage composition, can alloy, and processing temperature. For instance, epoxy and polyester liners may be preferred for low-pH, high-acid beverages such as wine, kombucha, or fruit seltzers, whereas acrylic or oleoresin systems may be suitable for moderate-pH beverages such as beer, cider, or carbonated soft drinks.

In continued reference to FIG. 1, in some embodiments, the liner composition may include one or more functional additives selected to modulate chemical reactivity between the beverage and the can substrate. Such additives may include corrosion inhibitors, oxygen scavengers, UV stabilizers, or sulfonate-neutralizing agents configured to mitigate reactive sulfur compound formation. The compatibility of a liner material with a particular beverage composition may be determined as a function of chemical parameters including, but not limited to, pH, molecular sulfur dioxide concentration, titratable acidity, dissolved oxygen, chloride content, and alcohol by volume. For example, epoxy-based liners may exhibit greater long-term stability in beverages with moderate to high sulfur dioxide and low chloride concentrations, whereas acrylic-based liners may demonstrate reduced stability in those same conditions due to polymer degradation and permeability to sulfur compounds. In an embodiment, the liner composition parameters, including material type, curing temperature, and thickness distribution, may be represented as liner composition variables within the predictive compatibility model 128. These variables may be extracted from a liner specification dataset and correlated with simulated beverage-liner interaction outcomes, allowing the system to predict which liner materials and configurations will maintain the desired beverage stability under defined storage conditions. In some embodiments, the system may further identify optimal liner configurations that balance corrosion resistance, coating weight, and curing efficiency as a function of beverage chemistry and packaging requirements.

Still referring to FIG. 1, As a non-limiting illustration, certain beverage formulations may demonstrate enhanced compatibility with specific liner compositions and configurations. For instance, dry white wines and sparkling wines characterized by low pH (<3.4), high molecular $SO_2$ (>1.5 mg/L), and moderate titratable acidity may exhibit optimal long-term stability when packaged with BPA-NI epoxy liners cured to a thickness of approximately 3 μm to 4 μm. Red wines containing elevated polyphenol content and lower free $SO_2$ (<20 mg/L) may be more compatible with polyester-epoxy hybrid coatings, which exhibit reduced permeability to oxygen and reactive sulfur compounds. Carbonated seltzers and functional beverages formulated at near-neutral pH (3.8-4.2) with low sulfur content may perform well in acrylic or oleoresin liners of 2 μm to 3 μm thickness, whereas acidic fruit beverages (pH<3.0, high titratable acidity >7 g/L) may favor cross-linked epoxy-polyester blends for corrosion resistance. In other embodiments, THC- or terpene-infused beverages may employ oleoresin or BPA-NI epoxy liners containing oxygen scavengers or aromatic-blocking additives to prevent oxidative degradation and flavor absorption into the coating matrix. In some embodiments, the predictive compatibility model 128 may correlate such pairings as part of the compatibility dataset, allowing the system to output a liner compatibility score 134 indicative of the expected chemical and sensory performance for each beverage-liner combination. The model may thus automatically recommend a liner composition or curing configuration suited to a given formulation profile, effectively linking beverage chemistry parameters to manufacturable packaging specifications.

In further reference to FIG. 1, in an embodiment, determining the liner compatibility score 134 may include computing, for each candidate liner composition 174, a numerical stability index 164 representing a confidence value 166 that the beverage composition 122 will remain chemically and sensorially stable within the composition adjustment threshold 124. For purposes of this disclosure, a "numerical stability index" is a scalar or vector-valued output generated by the predictive compatibility model 128 that quantifies the predicted degree of packaging stability under a given formulation-liner configuration. In an embodiment, the numerical stability index 164 may be computed as a weighted aggregation of multiple simulated outcomes, such as corrosion probability, oxidation potential, and off-odor risk, each normalized to a common scale to permit quantitative comparison across liner compositions. In some embodiments, the numerical stability index 164 may be derived from a probabilistic inference model, such as a logistic regression classifier, neural network output layer, and/or Bayesian posterior probability distribution, configured to estimate the likelihood of compatibility within specified tolerance ranges.

With further reference to FIG. 1, for purposes of this disclosure, a "confidence value" is a computed measure indicating the reliability or certainty of the predicted stability outcome. In an embodiment, the confidence value 166 may represent the probability that the beverage composition 122 remains within acceptable quality boundaries over its intended storage period, given the variance of the predictive model and the sensitivity of the input parameters. In some embodiments, the confidence value 166 may be accompanied by an uncertainty metric, such as a confidence interval or standard deviation, derived from ensemble predictions or Monte Carlo simulations, thereby enabling at least a processor 108 to distinguish between high-certainty and low-certainty compatibility outcomes. For purposes of this disclosure, "chemically stable" refers to the condition in which the beverage composition 122 maintains substantially constant chemical composition and reaction equilibria over time without undergoing undesired reactions. For example, such as oxidation, hydrolysis, metal ion exchange, or polymer-liner degradation that could alter its chemical identity or safety profile. For purposes of this disclosure, "sensorially stable" refers to the condition in which the beverage composition 122 maintains its intended organoleptic attributes without the development of perceptible off-odors, color shifts, turbidity, or texture changes detectable through sensory evaluation. In an embodiment, chemically and sensorially stable conditions may be jointly represented in the numerical stability index 164 through a composite scoring function that assigns proportional weighting to analytical (chemical) and perceptual (sensory) metrics as a function of the product type and target consumer quality threshold.

With continued reference to FIG. 1, in an embodiment, determining the liner compatibility score 134 may further include normalizing and aggregating the numerical stability indices computed across the plurality of candidate liner compositions 130 to enable direct comparison and ranking. In an embodiment, at least a processor 108 may normalize each numerical stability index 164 by applying a scaling transformation, such as min-max normalization or z-score standardization, thereby mapping all computed values to a common numerical range (e.g., 0 to 1 or −1 to +1). In an embodiment, this normalization may account for differences in model sensitivity, beverage composition variance, and/or liner-specific data density within the compatibility dataset 156. In some embodiments, at least a processor 108 may apply a weighting function to emphasize outcome metrics that carry greater practical or regulatory significance for a given beverage category. For instance, corrosion resistance and metal ion migration may be assigned higher weighting factors for acidic beverages such as wine or juice, while sensory and color stability metrics may dominate for functional beverages or seltzers. In an embodiment, the normalized stability indices may be aggregated through a composite scoring algorithm, such as a weighted sum, geometric mean, or machine-learning ensemble regression function, producing a single ranked liner compatibility score 134 for each candidate liner composition 174. The aggregation process may optionally include a penalty or uncertainty adjustment term proportional to the model's confidence interval, thereby reducing the influence of predictions with low certainty. In an exemplary implementation, at least a processor 108 may store the computed liner compatibility scores 134 in a structured results table indexed by liner composition identifier and beverage formulation profile ID.

In an embodiment, the stored results may then be sorted, filtered, or clustered using ranking algorithms, such as top-k selection or Pareto frontier analysis, to identify liner compositions exhibiting optimal predicted performance within the defined composition adjustment thresholds 124. This ranking framework may allow producers to rapidly determine which liners provide the most stable and reproducible results without performing redundant experimental tests, while maintaining traceable quantitative justification for each liner selection.

Still referring to FIG. 1, in an embodiment, liner compatibility score 134 may be transmitted to an external processing framework. For purposes of this disclosure, an "external processing framework" refers to any computing environment, system interface, or data-processing pipeline that is distinct from the system executing predictive compatibility model 128 but is operably configured to receive and utilize the liner compatibility score 134 for downstream analysis, validation, or control operations. In some embodiments, the external processing framework may include a quality-control database and/or production management system that stores the liner compatibility score 134 together with associated beverage composition profiles 118 and packaging configuration parameters 170 to enable traceability and batch-level decision making. In other embodiments, the external processing framework may include a formulation-adjustment module or rules-based optimization engine that automatically modifies at least one chemical parameter of the beverage composition 122 in response to the received liner compatibility score 134 falling below a predetermined compatibility threshold 176. In still other embodiments, the external processing framework may correspond to a packaging validation pipeline, comprising one or more external information systems 138, which may receive the liner compatibility score 134 through an application programming interface (API), message queue, or other data-transfer protocol, and execute a verification, reporting, or alerting process in response. In an exemplary implementation, the external processing framework may serialize the liner compatibility score 134 and its associated metadata into a structured data object 178 conforming to a predefined schema (e.g., JSON, XML, or proprietary binary format) for integration with enterprise resource planning (ERP) systems or digital production records. The transmission of liner compatibility score 134 to the external processing framework may enable interoperability between predictive modeling environments and production-level control systems, ensuring that beverage composition and packaging selections are dynamically updated in accordance with predicted stability performance.

In continued reference to FIG. 1, in certain embodiments, the external processing framework may correspond to or interoperate with an external processing system such as that described in U.S. patent application Ser. No. 19/384,050, filed on Nov. 10, 2025, and entitled "APPARATUS FOR AND METHOD OF PREDICTIVE ADAPTATION OF DATA PARAMETERS," the entirety of which is incorporated herein by reference.

In further reference to FIG. 1, in an embodiment, at least a processor 108 may be configured to generate a liner compatibility profile 168, comprising, for each candidate liner composition 174, one or more of the liner compatibility score 134, one or more limiting chemical parameters 170, and at least one packaging configuration parameter 172. For purposes of this disclosure, a "liner compatibility profile" is a structured digital object that aggregates, for each candidate liner composition 174, predictive performance metrics and associated formulation constraints derived from the predictive compatibility model 128. In an embodiment, the liner compatibility profile 168 may serve as a comprehensive summary that links chemical composition features of the beverage formulation with liner-specific stability outcomes and actionable packaging specifications. Non-limiting examples of data fields within the liner compatibility profile 168 may include a normalized liner compatibility score 134, a list of limiting chemical parameters, recommended packaging configuration parameters, model confidence metrics, and/or visual indicators for ease of interpretation in a graphical interface.

In continued reference to FIG. 1, for purposes of this disclosure, a "limiting chemical parameter" is a specific measurable component or property of the beverage composition 122 that exerts a dominant influence on the compatibility outcome or defines a boundary beyond which packaging stability is compromised. In an embodiment, the limiting chemical parameter may be identified through feature-importance analysis, gradient sensitivity mapping, and/or correlation testing within the predictive compatibility model 128, quantifying how variation in each chemical parameter affects the liner compatibility score 134. Non-limiting examples of limiting chemical parameters may include pH, titratable acidity, dissolved oxygen, free or molecular sulfur dioxide concentration, chloride ion concentration, and/or metal ion content (e.g., copper or iron). In some embodiments, the limiting chemical parameters may be expressed as threshold values or sensitivity coefficients to guide formulation refinements that enhance liner performance while maintaining sensory and regulatory compliance.

With further reference to FIG. 1, for purposes of this disclosure, a "packaging configuration parameter" is a specification or recommendation associated with a packaging configuration optimized for compatibility with the given beverage formulation. In an embodiment, packaging configuration parameters may define material or process characteristics including liner type, coating chemistry, curing temperature, coating thickness, can body alloy, seam compound composition, headspace gas ratio, and/or recommended storage temperature range. In an embodiment, these parameters may be generated by at least a processor 108 based on correlations between liner compatibility scores 134, limiting chemical parameters, and historical configuration outcomes within the compatibility dataset 156. In some embodiments, the packaging configuration parameter may be represented as a structured configuration object that can be exported for integration with manufacturing control systems or quality-assurance software, thereby bridging predictive modeling with real-world production environments.

Still referring to FIG. 1, in an embodiment, at least a processor 108 may be further configured to generate the at least one packaging configuration parameter 172. In an embodiment, generating the at least one packaging configuration parameter 172 may include identifying, for each candidate liner composition 174, one or more limiting chemical parameters 170 as a function of the liner compatibility score 134. In an exemplary implementation, at least a processor 108 may execute a parameter sensitivity analysis routine that computes, for each chemical parameter of the beverage composition profile 118, a partial derivative or gradient score representing the rate of change in the liner compatibility score 134 relative to incremental variation in that parameter. Parameters exhibiting the greatest influence on the compatibility outcome, particularly those with negative correlation slopes, may be designated as limiting chemical parameters. In some embodiments, at least a processor 108 may further classify each limiting chemical parameter according to its direction of effect (e.g., whether an increase or decrease in value degrades stability) and magnitude of sensitivity.

With continued reference to FIG. 1, in an embodiment, once limiting chemical parameters are identified, at least a processor 108 may generate formulation adjustment recommendations within the previously defined composition adjustment thresholds 124. In an embodiment, these recommendations may include small modifications to the beverage formulation, such as adjusting titratable acidity, sulfur dioxide concentration, or dissolved oxygen level, provided such changes remain within the maximum permissible deviations 126 associated with sensory and regulatory limits. In some embodiments, at least a processor 108 may generate an adjustment table or delta map indicating the direction and approximate magnitude of adjustment likely to yield improved liner compatibility while maintaining product uniformity. For instance, if the limiting chemical parameter is dissolved oxygen, system 100 may recommend lowering the $dO_2$ concentration by a defined percentage, such as 5-10%, within the allowable threshold range to improve corrosion resistance without altering taste. In certain configurations, at least a processor 108 may apply optimization logic to simulate hypothetical formulation variants incorporating these minor adjustments and re-evaluate corresponding liner compatibility scores 134, thereby validating the predicted improvement in packaging stability. In an embodiment, the resulting adjustment recommendations may be appended to the liner compatibility profile 168 as supplementary guidance data. Through this configuration, system 100 may provide both material-level recommendations (e.g., liner composition selection) and formulation-level insights (e.g., permissible compositional adjustments) that together optimize the overall packaging configuration for chemical, sensory, and regulatory stability.

In further reference to FIG. 1, in an embodiment, generating the packaging configuration parameter may include analyzing correlations between the liner compatibility score 134, the identified limiting chemical parameters, and historical packaging outcome data contained within the compatibility dataset 156. In an embodiment, at least a processor 108 may implement a configuration synthesis routine that maps these multidimensional relationships to derive optimal material and process specifications associated with stable packaging performance. In some embodiments, at least a processor 108 may apply a rule-based or machine-learning-based inference engine trained on prior successful packaging configurations, correlating liner material class, coating chemistry, and process variables with positive stability outcomes. In an embodiment, at least a processor 108 may then interpolate or extrapolate from these learned relationships to generate a packaging configuration parameter tailored to the current beverage composition profile 118. Non-limiting examples of generated configuration parameters may include recommended liner resin type, coating thickness range, curing temperature, seaming torque, can body alloy, or nitrogen-purge setting.

With continued reference to FIG. 1, in an exemplary implementation, at least a processor 108 may execute a multivariate optimization algorithm, such as gradient descent or Bayesian optimization, constrained by the composition adjustment thresholds 124 and manufacturing feasibility constraints. In an embodiment, at least a processor 108 may iteratively adjust simulated configuration variables, compute corresponding predicted stability indices using the predictive compatibility model 128 and converge on the combination that maximizes the liner compatibility score 134 while minimizing deviation from standard process tolerances. The resulting optimized parameter set may then be serialized as a structured configuration object and appended to the liner compatibility profile 168. In an embodiment, this approach may allow the packaging configuration parameter to reflect not only empirical correlations but also dynamically optimized process variables, ensuring that the recommended configuration aligns with both chemical compatibility and production scalability requirements.

In continued reference to FIG. 1, in an embodiment, generating the at least one packaging configuration parameter 172 may include selecting a candidate liner composition 174 as a function of the liner compatibility score 134 and a predetermined compatibility threshold 176. For purposes of this disclosure, a "predetermined compatibility threshold" is a quantitative or categorical value defining the minimum acceptable liner compatibility score 134 required for a liner composition to be classified as suitable for the beverage composition 122 under evaluation. In an embodiment, the predetermined compatibility threshold 176 may be defined by the user 148, dynamically calculated based on model calibration data, and/or established through regulatory or internal quality standards. For instance, a producer may define a threshold corresponding to a minimum numerical stability index 164 (e.g., 0.85 on a 0-1 scale) or a categorical requirement that the predicted outcome be classified as "compatible." In some embodiments, at least a processor 108 may execute a selection routine that iterates through all candidate liner compositions 174 within the compatibility dataset 156, compares each computed liner compatibility score 134 to the predetermined compatibility threshold 176, and filters out those that fall below the specified limit. In an embodiment, at least a processor 108 may then identify the liner or set of liners exceeding the threshold with the highest associated compatibility scores as potential optimal configurations. In an exemplary implementation, if multiple liner compositions surpass the compatibility threshold, at least a processor 108 may apply secondary selection criteria, such as minimizing cost, environmental impact, or processing complexity, to determine the preferred liner.

Still referring to FIG. 1, in an embodiment, the predetermined compatibility threshold 176 may be adaptive rather than static, adjusting dynamically based on observed model performance metrics, beverage composition type, and/or historical success rates within specific product categories. For example, at least a processor 108 may apply a higher threshold for high-acid beverages (e.g., wines or fruit-based drinks) and a lower one for neutral-pH products (e.g., functional beverages or teas) to reflect the differing sensitivities of each formulation class. In some embodiments, at least a processor 108 may also store user-specific or product-specific threshold profiles in memory, enabling automated reapplication of the same compatibility criteria during subsequent evaluations of related formulations. In an embodiment, the selected candidate liner composition 174 may be appended to the liner compatibility profile 168 and linked to its corresponding packaging configuration parameter. In some cases, system 100 may then present this selection as the recommended liner configuration, optionally including confidence metrics, parameter sensitivities, and formulation adjustment recommendations generated in earlier stages. By incorporating the predetermined compatibility threshold 176 into the selection process, system 100 may ensure that only liner configurations meeting or exceeding defined stability and quality standards are surfaced as viable options, thereby improving reliability and reducing packaging-related failures in production environments.

With further reference to FIG. 1, in an embodiment, generating the at least one packaging configuration parameter 172 may include outputting, as a function of the candidate liner composition 174, the at least one packaging configuration parameter 172. In an embodiment, outputting may include generating a structured digital data object 178 that encapsulates the configuration parameters, associated liner identifiers, compatibility metrics, and/or formulation adjustment recommendations derived from prior processing steps. For purposes of this disclosure, such a data object 178 may be represented in a machine-readable format, including but not limited to JavaScript Object Notation (JSON), Extensible Markup Language (XML), comma-separated values (CSV), or binary serialization formats such as Protocol Buffers. In an embodiment, at least a processor 108 may transmit this output using an interface module to one or more external systems, including laboratory information management systems (LIMS), quality-control dashboards, manufacturing execution systems (MES), or digital twin simulation environments. In some embodiments, at least a processor 108 may further generate a visual representation of the packaging configuration parameter through an interactive graphical user interface (GUI). The GUI may display each selected liner composition alongside its corresponding compatibility score, predicted stability metrics, limiting chemical parameters, and suggested formulation adjustments. In an exemplary implementation, at least a processor 108 may render a multi-panel dashboard where each candidate liner is represented as a card or data tile containing real-time color-coded indicators for corrosion risk, color shift, off-odor probability, and overall stability index. In an embodiment, threshold exceedances may be highlighted visually to enable rapid interpretation by technical users.

In further reference to FIG. 1, in an embodiment, the output packaging configuration parameter may also be stored in a version-controlled configuration repository, allowing traceability of each generated recommendation over time and across formulation revisions. In an embodiment, this repository may support rollback functionality, batch tagging, and/or audit logging, enabling producers to track how compatibility assessments evolve as formulations or liner compositions change. In some embodiments, at least a processor 108 may further generate a packaging configuration report, which consolidates the recommended liner configuration, associated formulation thresholds, and predicted performance metrics into a portable document (e.g., PDF) or formatted printout suitable for regulatory documentation or supplier communication. In certain implementations, the process of outputting the packaging configuration parameter may include bi-directional synchronization with cloud-based manufacturing systems, wherein accepted packaging configuration parameters can automatically update production line settings or inform automated coating or curing controls. Conversely, feedback data collected from post-production testing or shelf-life studies may be ingested by the same processor to refine future recommendations through adaptive retraining of the predictive compatibility model 128. In an embodiment, through these output and integration mechanisms, system 100 may transform predictive analytical insights into actionable, verifiable configuration data that can be directly applied within operational and regulatory workflows.

Still referring to FIG. 1, in an embodiment, at least a processor 108 may be configured to output the liner compatibility profile 168 as a data object 178. For purposes of this disclosure, a "data object" is a structured digital representation of information encapsulating related data fields, metadata, and relationships that can be processed, transmitted, or stored by computing systems. In an embodiment, a data object 178 may include both analytical content, such as numerical scores, identifiers, or configuration parameters, and descriptive metadata, such as timestamps, user identifiers, and model provenance. In an embodiment, the data object 178 may be formatted using a standardized interchange protocol such as JavaScript Object Notation (JSON), Extensible Markup Language (XML), or Parquet, thereby enabling system interoperability, schema validation, and compatibility with downstream analytical pipelines. For purposes of this disclosure, the liner compatibility profile 168 may be represented as such a data object 178 that aggregates, for each candidate liner composition 174, the computed liner compatibility score 134, limiting chemical parameters, and one or more packaging configuration parameters. In an embodiment, at least a processor 108 may serialize the liner compatibility profile 168 into the selected machine-readable format and append metadata fields such as timestamp, user ID, beverage formulation ID, predictive model version, and/or corresponding confidence intervals. This may ensure traceability, reproducibility, and compliance with data-integrity standards across laboratory, quality-control, and production environments.

With further reference to FIG. 1, in some embodiments, at least a processor 108 may output the liner compatibility profile 168 to external processing pipelines for additional analysis, reporting, or integration into automated decision systems. For instance, the data object 178 may be transmitted through an application programming interface (API) to a quality-control engine, a formulation adjustment module, and/or a manufacturing execution system (MES) to automatically update packaging line settings according to the selected liner composition. In certain configurations, the liner compatibility profile 168 may also be stored within a centralized data warehouse or cloud-based analytics environment for cross-referencing with historical production data, sensory results, and long-term stability outcomes. In an embodiment, at least a processor 108 may further generate notifications or digital certificates indicating verified compatibility between a given beverage formulation and liner composition, enabling seamless coordination with procurement, supplier qualification, or regulatory documentation systems.

In continued reference to FIG. 1, in an embodiment, at least a processor 108 may further generate a visual output of the liner compatibility profile 168 through an interactive graphical user interface (GUI) configured to present both quantitative and qualitative indicators of packaging stability. In an embodiment, the GUI may include dynamic visualizations such as bar charts, radar plots, and/or matrix heatmaps representing liner compatibility scores 134 across candidate liner compositions 174. In an exemplary embodiment, a filtering panel may allow users 148 to organize liner options based on compatibility score, limiting parameter sensitivity, or process feasibility. In an embodiment, visual highlights or threshold markers may indicate which chemical parameters are constraining stability, while interactive sliders may enable users 148 to preview how minor adjustments within allowable composition thresholds could shift the predicted compatibility outcome. In certain embodiments, at least a processor 108 may support multi-modal output, wherein the liner compatibility profile 168 is simultaneously displayed to the user 148, exported to downstream processing modules, and archived in a secure, version-controlled repository. The repository may assign a unique digital signature or checksum to each generated data object 178, ensuring data authenticity and enabling later retrieval for audit or re-analysis. In an embodiment, through these output mechanisms, system 100 may provide both human-interpretable visualization and machine-level interoperability, creating a seamless bridge between predictive modeling, user interaction, and automated implementation within beverage packaging workflows.

With continued reference to FIG. 1, in an embodiment, system 100 may further include a feedback integration and model-retraining module configured to iteratively refine the predictive compatibility model 128 based on real-world packaging performance data. In an embodiment, at least a processor 108 may receive post-production quality-control data, sensory evaluation results, and/or shelf-life stability outcomes corresponding to beverage formulations that have been packaged using previously recommended liner compositions. In an embodiment, at least a processor 108 may extract key features from these records, such as measured corrosion rates, color changes, volatile compound formation, or consumer rejection metrics, and map them to their associated liner compatibility profile 168 entries. These newly acquired data points may be used to augment the existing compatibility dataset 156, thereby improving the predictive model's generalization across product categories, liner chemistry, and production conditions. In some embodiments, the feedback integration process may include automated retraining of the predictive compatibility model 128 according to a defined update schedule or upon accumulation of a threshold quantity of new verified data. In an embodiment, at least a processor 108 may execute retraining locally and/or through a cloud-based distributed learning framework that performs batch updates to model weights using standard optimization algorithms such as stochastic gradient descent or Adam. In an embodiment, the retraining process may also include validation and testing phases that evaluate model performance against holdout data subsets to ensure prediction accuracy and prevent overfitting. Metrics such as mean absolute error (MAE), F1-score, or area under the receiver operating characteristic curve (AUC-ROC) may be computed to quantify retraining success.

Still referring to FIG. 1, in an exemplary implementation, feedback integration may further employ reinforcement-style learning techniques, wherein the model continuously refines its compatibility predictions based on reward functions derived from observed stability outcomes in actual production environments. For instance, packaging configurations that maintain stability over the intended shelf life may yield positive reinforcement, while configurations resulting in corrosion, delamination, and/or sensory degradation may produce negative reinforcement signals. In an embodiment, at least a processor 108 may adjust model parameters to increase the likelihood of selecting high-performing liner-formulation combinations in subsequent iterations. In certain embodiments, privacy-preserving retraining architectures may be employed, wherein each participating producer or laboratory site retains ownership of its proprietary formulation and liner performance data. In some cases, at least a processor 108 may transmit only anonymized statistical gradients or correlation structures to a central model repository, consistent with differential privacy or federated learning techniques. This configuration may enable collective model improvement across multiple producers while ensuring that raw formulation data and proprietary ingredient ratios remain confidential. In an embodiment, through this adaptive feedback loop, system 100 may evolve into a continuously learning platform capable of improving predictive precision, reducing experimental overhead, and ensuring sustained accuracy as new beverage categories, liner chemistries, and environmental conditions are introduced.

In continued reference to FIG. 1, in an embodiment, system 100 may further include a model deployment and version management routine configured to distribute retrained predictive compatibility models 128 back into the active inference environment. In an embodiment, at least a processor 108 may, upon completion of retraining, serialize the updated model weights, configuration parameters, and associated performance metrics into a version-controlled model package. Each model package may include metadata describing its training dataset composition, model architecture, validation accuracy, and unique version identifier. In an embodiment, at least a processor 108 may then store this package within a model repository, a secure data structure configured to manage multiple active and historical versions of the predictive compatibility model 128. In some embodiments, before redeployment, at least a processor 108 may execute a revalidation sequence to confirm that the updated model satisfies defined performance thresholds and does not introduce degradation in prediction accuracy for known beverage-liner configurations. In an embodiment, the revalidation process may include back-testing against archived compatibility profiles, cross-comparison with prior versions, and/or validation on a held-out test set representing diverse beverage categories and liner chemistry. In some cases, only models meeting or exceeding defined validation criteria (e.g., ≥95% compatibility classification accuracy or ≤0.05 MAE) may be promoted to active status.

With further reference to FIG. 1, in an exemplary implementation, deployment of an approved model version may occur through an orchestrated update mechanism, wherein the active inference module of system 100 retrieves the serialized model from the repository and replaces the prior version without interrupting ongoing analytical operations. In some configurations, system 100 may maintain parallel inference pipelines, allowing both the legacy and newly retrained models to operate concurrently during an evaluation period to ensure prediction continuity. Feedback from this dual-mode operation may be logged and analyzed by at least a processor 108 to determine whether the new model exhibits improved stability prediction or expanded generalization across novel beverage formulations. In certain embodiments, users 148 may be notified through the graphical interface of a model update event, with summary statistics displayed for transparency, including retraining date, key parameter shifts, and performance deltas. Additionally, system 100 may provide model rollback functionality, allowing a user 148 or administrator to revert to a previous model version if operational anomalies or unexpected compatibility deviations are detected post-deployment. In an embodiment, through these retraining and deployment mechanisms, system 100 may achieve a self-improving, auditable learning architecture that preserves trust, transparency, and technical robustness while continuously advancing predictive performance in beverage-liner compatibility analysis.

As described herein, embodiments of the present disclosure provide significant technical improvements over conventional beverage packaging compatibility evaluation methods. In an embodiment, the disclosed system may eliminate the need for repetitive empirical trials, reduce laboratory resource consumption, and improve the reproducibility and precision of stability predictions across diverse beverage and liner types. By incorporating analytical chemistry data, predictive modeling, and feedback-driven retraining, system 100 may enable a closed-loop optimization framework that bridges formulation science with manufacturing execution. In an embodiment, system 100 may achieve computational efficiency by parallelizing simulation cycles across liner candidates and dynamically constraining formulation adjustments within verified chemical tolerances, thereby reducing simulation time and improving throughput without compromising analytical accuracy. In one or more embodiments, a technical improvement is further achieved through the integration of multi-source data fusion and privacy-preserving model learning, allowing collaborative knowledge expansion without exposure of proprietary beverage formulations. This architecture may enable producers, laboratories, and coating suppliers to contribute anonymized correlation data to a collective compatibility model, resulting in improved predictive accuracy and generalizability across product categories. Additional improvements are realized in system transparency and traceability through version-controlled model management, structured compatibility profiles, and visual dashboards that communicate complex stability predictions in an interpretable manner.

In further reference to FIG. 1, in some embodiments, the disclosed systems and methods may be extended beyond aluminum can packaging to other packaging materials and beverage categories. Non-limiting examples of alternative applications include glass bottle internal coatings, polymer-based beverage containers, stainless-steel keg linings, and composite packaging systems for high-acid or functional beverages. In an embodiment, the underlying predictive compatibility framework may also be adapted to assess formulation-surface interactions in adjacent industries such as cosmetics, pharmaceuticals, and/or nutraceuticals, where chemical stability at packaging interfaces is similarly critical. In certain configurations, the predictive compatibility model 128 may also be integrated with material discovery engines to screen novel liner chemistries and simulate performance under virtual stress or accelerated aging conditions. Other embodiments of the disclosure may employ variations in model architecture, including hybrid rule-based and neural modeling systems, probabilistic graphical models, and/or reinforcement learning frameworks configured to iteratively optimize liner-formulation pairings based on simulated feedback. In yet further embodiments, additional modules may be implemented to track environmental or logistical parameters such as storage temperature, humidity, transportation vibration, or warehouse exposure time, allowing system 100 to dynamically adjust packaging recommendations according to real-world distribution conditions. In an embodiment, through these features and extensions, the present disclosure may provide a flexible, data-driven platform capable of learning from both laboratory and production environments, continuously refining its predictive accuracy and expanding its applicability across beverage categories, packaging substrates, and environmental contexts. The disclosed system thus may represent a technically advanced, privacy-conscious, and scalable framework for modern beverage packaging compatibility analysis and optimization.

This invention provides a solution to the technical problem of evaluating whether a liquid formulation, such as wine, functional beverages, or THC-infused seltzers, will retain its chemical stability and sensory attributes when stored in aluminum packaging. The disclosed system combines analytical characterization of beverage chemistry parameters (including pH, sulfur dioxide, titratable acidity, and dissolved oxygen) with a predictive modeling framework configured to assess liner-formulation compatibility and recommend compositional refinements. The resulting output comprises a formulation compatibility profile optimized for aluminum canning, thereby facilitating efficient pre-production screening of beverage formulations and minimizing the need for empirical, trial-based testing.

EXPERIMENTAL RESULTS

In continued reference to the present disclosure, FIGS. 2 through 22 collectively present experimental data, model validation results, and comparative analyses that support the predictive framework and compatibility modeling processes described herein. In an embodiment, the following figures illustrate representative studies conducted to validate the relationships between beverage chemistry parameters, liner composition variables, and packaging stability outcomes. These results may demonstrate how the disclosed systems and methods replicate and predict real-world interactions between beverage formulations and aluminum can liners with high fidelity. In an embodiment, the experimental findings may further substantiate the capability of the predictive compatibility model to generalize across beverage categories and to identify stability-limiting factors, such as molecular $SO_2$ concentration, liner thickness variation, or additive permeability, that impact long-term performance. It will be appreciated that the data shown are provided for purposes of illustration and are not intended to limit the scope of the disclosure; other validation studies and analytical configurations may be employed to achieve comparable insights. Collectively, the figures establish empirical and computational evidence supporting the technical basis of the system and methods described herein.

In some embodiments, the present disclosure is informed by market observations indicating significant growth in the adoption of aluminum packaging for wine and related beverage products. As of 2021, the global market for canned wines was reported to generate approximately 235.7 million USD in revenue and is projected to increase to roughly 571.8 million USD by 2028. This represents a substantial rise from early market estimates of approximately 2 million USD in 2014. The accelerated adoption of canned wine products may be attributed, at least in part, to factors including the portability and lightweight nature of aluminum packaging, its mechanical durability, established recyclability and circular-economy advantages, and its permissibility in venues or environments where glass packaging is restricted or impractical. These market trends underscore the growing demand for reliable, shelf-stable packaging systems capable of preserving the sensory and chemical integrity of wine and other high-acid beverages during long-term storage in aluminum containers.

In some embodiments, wine producers and beverage manufacturers have expressed concern regarding the potential effects of aluminum packaging systems on product quality and stability. Aluminum metal ($Al^0$) may undergo oxidation in the presence of oxygen and/or water to form a passive oxide layer comprising oxidized aluminum species (e.g., $Al^{3+}$, $Al_2O_3$). In the absence of an internal protective barrier, and under the low-pH conditions, typical of wine and similar acidic beverages (e.g., pH<4), this passive layer may dissolve, leading to an increase in dissolved aluminum ions and, over time, to corrosion-related degradation of the container's integrity, including potential leakage or loss of hermetic seal. To mitigate these effects, a thin polymeric coating, referred to herein as a liner, varnish, or lacquer, is typically applied to the interior surface of the aluminum container to serve as a chemical barrier between the beverage and the metal substrate.

Historically, such beverage can liners have predominantly consisted of bisphenol A (BPA)-based epoxy formulations, long considered the "gold standard" since the mid-twentieth century due to their chemical inertness, low production cost, and high barrier performance. However, in recent years, the use of BPA-containing materials has declined because of regulatory and public health concerns associated with its potential endocrine activity. Certain jurisdictions have implemented explicit bans on BPA use in food-contact coatings or labeling disclosure requirements. As a result, bisphenol A-non-intent (BPA-NI) liner formulations have gained prominence. Non-limiting examples of these include coatings based on acrylic resins and epoxy systems derived from alternative monomers exhibiting reduced estrogenic or endocrine-related activity, such as tetramethyl bisphenol F. These developments underscore the growing need for predictive systems capable of assessing compatibility between new liner chemistries and complex beverage matrices without relying solely on time- and resource-intensive empirical testing.

In some embodiments, even when an internal liner is applied, evidence indicates that aluminum beverage packaging may interact chemically with certain wine formulations to generate volatile sulfur compounds such as hydrogen sulfide ($H_2S$), which is associated with a characteristic "rotten egg" aroma and exhibits an odor detection threshold near approximately 1 μg/L (Allison et al., 2021). Empirical studies have demonstrated that commercial wines stored in glass containers typically maintain sub-threshold or undetectable $H_2S$ levels (<6 μg/L) over extended storage periods (e.g., eight months), whereas the same wines packaged in lined aluminum cans have exhibited substantially elevated concentrations, in some cases exceeding 1000 μg/L when stored in acrylic-lined containers. Elevated $H_2S$ levels, on the order of ~50 μg/L, have also been observed in cans lined with both BPA-based and BPA-non-intent (BPA-NI) epoxy systems.

Across tested formulations, the most consistent predictor of $H_2S$ accumulation was the initial concentration of molecular sulfur dioxide ($SO_2$), with additional correlations observed for free $SO_2$ and pH. Other compositional factors, such as total $SO_2$, chloride concentration, copper content, and alcohol by volume, were found to be weakly or inconsistently correlated with $H_2S$ production. Based on these observations, the primary mechanism of hydrogen sulfide formation during can storage has been hypothesized to involve an electrochemical reduction pathway in which metallic aluminum ($Al^0$) reacts with dissolved $SO_2$ and hydrogen ions under acidic conditions to yield aqueous aluminum ions ($Al^{3+}$), gaseous $H_2S$, and water, as represented schematically by the following equation: $2\ Al^0_{(s)}+SO_{2(aq)}\rightarrow 2\ Al^{3+}_{(aq)}+H_2S_{(g)}+2\ H_2O$.

In some embodiments, this reaction may occur at localized defects or diffusion points within the liner film, where acidic wine components and dissolved gases penetrate to the metal interface. Over time, this process can result in both sensory degradation of the packaged beverage and potential compromise of the can's structural or hermetic integrity. In some embodiments, wines exhibiting elevated hydrogen sulfide ($H_2S$) concentrations during aluminum can storage have also demonstrated visual or analytical evidence of liner degradation. Without being bound by theory, it is believed that sulfur dioxide ($SO_2$) present in the beverage composition may either (i) directly compromise the chemical integrity of the liner polymer or (ii) permeate through microdefects or diffusion channels within the liner, enabling local reactions at the metal interface that generate $H_2S$ gas and promote liner delamination or adhesion failure.

Earlier investigations have primarily focused on liner systems obtained from a single can manufacturer, without accounting for inter-manufacturer variability in $H_2S$ formation behavior for nominally similar liner chemistries. It is therefore hypothesized that the extent of $H_2S$ generation during long-term storage may vary among can manufacturers even when equivalent liner types are employed. In some embodiments, such variability may arise from differences in alloy composition, internal coating uniformity, curing conditions, or the application consistency of the liner itself. It is further hypothesized that these factors can be characterized through analytical and materials-science methodologies, such as microscopy, spectroscopy, surface profilometry, or electrochemical impedance spectroscopy, to establish correlations between physical liner attributes, compositional heterogeneity, and observed $H_2S$ formation kinetics.

In some embodiments, the materials and chemical reagents utilized in experimental validation or model training may include one or more of acetaldehyde (≥99%), potassium metabisulfite ($K_2S_2O_5$, ≥99%, "KMBS"), copper sulfate (≥99%), and sodium chloride (≥99%). Such reagents may be obtained from commercial suppliers including, but not limited to, Alfa Aesar, Chem Products, Sigma-Aldrich, and Calbiochem. Additional acids, bases, and buffering components may include sulfuric acid (e.g., 25% v/v) and potassium carbonate (≥99%; $K_2CO_3$), which may be produced by BDH Chemicals and/or distributed by VWR. In an embodiment, deionized, distilled water exhibiting a resistivity of approximately 18.2 MΩ·cm at 25° C. may be generated using a purification system such as a Milli-Q apparatus (Millipore Sigma) and may serve as the solvent in all aqueous preparations and dilutions.

In some embodiments, nitrogen gas and/or liquid nitrogen ($N_2$, ultra-high purity grade) may be employed for sample purging, inert blanketing, or cryogenic preservation. Suitable sources may include compressed gas cylinders supplied by Airgas USA LLC. In an embodiment, a portable liquid nitrogen sprayer of approximately 500 mL capacity may be utilized for localized cooling (e.g., US Solid model). Experimental containers may include 27 mL headspace vials (e.g., 30 mm×60 mm), 20 mm butyl rubber septa, and tear-away crimp seals, all of which may be obtained from Supelco (e.g., product codes 27298, Z166065, 27016, and 33280-U, respectively). In some embodiments, a 5-25 mL bottle-top dispenser (e.g., VWR, product code 82017-768) may be employed to enable volumetric precision in reagent dispensing.

In one embodiment, reaction monitoring and storage may be performed using coated glass bottles (e.g., 1000 mL capacity) equipped with septum ports to permit headspace sampling (e.g., Ankom Technology). For thermal or adhesive control processes, a benchtop electric glue skillet (e.g., Surebonder, FPC Corporation) and ethyl vinyl acetate (EVA) hot glue pellets (e.g., B-2001, Surebonder-FPC Corp.) may be used to create airtight seals or mounting fixtures during test preparation. In some embodiments, industry collaborators may supply aluminum packaging materials, such as 0.24 mm-thick sheets of 3004-series aluminum alloy coated on both sides with approximately 2 μm of BPA-non-intent (BPA-NI) epoxy. Aluminum beverage can bodies may be of standard 355 mL capacity (e.g., 202D/211 standard, 202/204×604 sleek geometry), with can ends comprising 5000-series alloy and BPA epoxy (e.g., 202LOE B64 style). Exemplary coatings for can bodies may include BPA epoxy, BPA-NI epoxy, and acrylic formulations, each with thicknesses ranging from approximately 2 μm to 5 μm; uncoated aluminum controls may also be included. In certain embodiments, can sealing may be achieved using a benchtop can seamer (e.g., Oktober MK16, Oktober Design).

In some embodiments, a plurality of commercial wine formulations may be selected for compositional analysis and packaging compatibility testing. In an exemplary implementation, five wines were provided by an industry collaborator in twenty-liter (20 L) high-density polyethylene (HDPE) KeyKegs. The formulations included, for example, a Pinot Grigio (PG), a Sauvignon Blanc (SB), a French Rosé (FR), a sparkling Rosé (RB), and a sparkling White Blend (WB). Each wine formulation may correspond to a unique beverage composition profile characterized by parameters such as titratable acidity, sulfur dioxide concentration, and dissolved oxygen. In some embodiments, information relating to the wine style, vintage, and baseline composition may be recorded in an auxiliary dataset or supplemental table accessible for model calibration or experimental validation.

In one embodiment, initial analytical measurements of the wine compositions may be performed using standard industry methods, such as those implemented by a certified analytical facility (e.g., Cornell Craft Beverage Analytical Laboratory, Geneva, NY). Alcohol by volume (ABV) may be determined using a near-infrared spectroscopic analyzer (e.g., Foss OenoFoss). Free sulfur dioxide ($SO_2$) concentration may be quantified by flow injection analysis using an automated analyzer (e.g., Foss FIAstar 5000). Titratable acidity (TA) may be measured by titration with standardized 0.1 N sodium hydroxide to a pH 8.2 endpoint using an automated titrator (e.g., Metrohm 862 Compact or Hanna Instruments HI901 W). The pH value may be determined using a dual-channel pH/ion meter (e.g., Fisher Scientific Accumet Excel XL25).

In an embodiment, molecular sulfur dioxide ($SO_2$) concentration may be calculated using an equilibrium-based relationship between free $SO_2$, pH, and the acid dissociation constant (pKa), such as represented by the following equation:

$$\text{Molecular } SO_2 = \frac{\text{Free } SO_2}{1 + 10^{pH-pKa}}.$$

In some embodiments, the dissociation constant (pKa) may be adjusted as a function of ethanol concentration and temperature to improve the accuracy of molecular $SO_2$ estimation across different beverage matrices. Such molecular $SO_2$ values may form part of the analytical feature vector associated with the beverage composition profile and may serve as key predictive parameters in the compatibility model described herein.

In further embodiments, elemental aluminum concentration in the wine formulations may be determined using inductively coupled plasma-atomic emission spectroscopy (ICP-AES). For example, analyses may be performed on a Thermo Scientific iCAP 6500 series system following standard USDA-ARS Holley Center protocols. In some embodiments, these aluminum concentration values may be used to evaluate pre-contact aluminum levels in the beverage matrix or to assess background metal ion contamination that may influence corrosion potential during storage. Initial hydrogen sulfide ($H_2S$) concentration in each wine formulation may be determined prior to canning using gas detection tubes or equivalent analytical instrumentation. These baseline measurements may provide a control dataset against which $H_2S$ accumulation during simulated or real-time storage can be compared.

In some embodiments, the packaging procedure may involve filling aluminum beverage cans with liquid formulations directly from bulk storage vessels. In an exemplary embodiment, cans were filled with wine directly from twenty-liter (20 L) high-density polyethylene KeyKegs using a manual pump assembly supplied by the KeyKeg manufacturer. In certain embodiments, the filling operation may be configured to minimize oxygen ingress by maintaining a closed transfer system or inert gas blanket over the dispensing interface. In one embodiment, following filling, a small quantity of liquid nitrogen ($LN_2$) may be introduced into the can headspace to displace residual oxygen and establish a low-oxygen environment prior to sealing. The liquid nitrogen may vaporize rapidly, thereby sparging the headspace of $O_2$ and creating slight internal pressurization that enhances seam integrity. Immediately thereafter, the can may be topped with a corresponding lid and sealed using a manual or automated double seamer. In an exemplary embodiment, a benchtop MK16 double seamer (Oktober Design) may be utilized to complete the closure process. In some embodiments, seam quality may be validated according to an established industry protocol involving the measurement of multiple seam parameters. For example, seam thickness may be measured at four distinct points corresponding to the first operation, second operation, cover hook, and body hook. Measurements may be collected at three circumferential positions around the can seam to ensure uniformity and compliance with dimensional tolerances. Seam validation procedures may follow technical recommendations such as those provided by the equipment manufacturer (e.g., Oktober Design, 2024).

In an embodiment, prior to initiating canning experiments, total package oxygen (TPO) may be evaluated as a quality assurance parameter. For purposes of this disclosure, "total package oxygen" refers to the sum of dissolved and gaseous oxygen present within a sealed container, normalized to total package volume. In one implementation, TPO may be measured according to previously established methods using model wine as a representative matrix. During TPO determination, oxygen in the liquid and headspace phases may be equilibrated by gentle agitation for approximately one hour. In an exemplary configuration, following equilibration, the can may be opened and the dissolved oxygen concentration in the liquid measured using a trace-level optical oxygen sensor (e.g., Fibox 3 LCD trace $O_2$ meter equipped with a DP-PSt6 $O_2$ dipping probe, PreSens). The headspace oxygen concentration may be estimated from the measured headspace volume and a literature-derived oxygen solubility constant. The total package oxygen (TPO) may then be calculated as the sum of dissolved and headspace oxygen content, normalized to total package volume. For the cans evaluated, the TPO was determined to be less than approximately 1.5 mg $O_2$/L. In some embodiments, maintaining a TPO level below 2.0 mg $O_2$/L may be advantageous for mitigating oxidative degradation and promoting accurate modeling of long-term packaging stability.

In some embodiments, the effects of pH, free sulfur dioxide ($SO_2$), and molecular $SO_2$ concentration on hydrogen sulfide ($H_2S$) formation during long-term storage may be evaluated using controlled experimental groupings. In an exemplary implementation, five wine formulations, Pinot Grigio (PG), Sauvignon Blanc (SB), French Rosé (FR), sparkling Rosé (RB), and sparkling White Blend (WB), may be prepared in three distinct compositional groups prior to canning. Each group may be configured to represent a different $SO_2$ equilibrium condition and acidity regime. In one embodiment, Group 1 may serve as a low-molecular-$SO_2$ and low-free-$SO_2$ control, comprising unmodified wines without additional adjustments. Group 2 may represent low-molecular-$SO_2$ and high-free-$SO_2$ conditions, achieved by addition of potassium metabisulfite (KMBS) and adjustment of pH to approximately 3.65-3.80 using potassium carbonate ($K_2CO_3$). Group 3 may represent high-molecular-$SO_2$ and high-free-$SO_2$ conditions, achieved through KMBS addition without subsequent pH adjustment. In some embodiments, this design may isolate the influence of proton concentration (pH) on molecular $SO_2$ equilibrium while maintaining consistent free $SO_2$ differentials between Groups 2 and 3.

In certain implementations, the adjusted free $SO_2$ concentrations may range between approximately 15-20 mg/L for the low-free-$SO_2$ condition and 40-50 mg/L for the high-free-$SO_2$ condition. Correspondingly, the molecular $SO_2$ concentrations may range between approximately 0.6-1.1 mg/L for the low condition and 1.5-2.5 mg/L for the high condition. The native (unadjusted) pH values of the wines may range from approximately 3.11 to 3.37, whereas the pH-adjusted formulations may range from approximately 3.65 to 3.80. In one embodiment, the pH adjustment for Group 2 may be calibrated such that its free $SO_2$ concentration approximates that of Group 3, thereby decoupling the contributions of pH and total $SO_2$ to $H_2S$ formation kinetics. In some embodiments, the prepared wines may be packaged in aluminum cans as previously described and sealed using one of three can liner compositions. The liner types may include: (i) a bisphenol A (BPA)-based epoxy liner (Company X), (ii) a BPA-non-intent (BPA-NI) epoxy liner (Company Y), and (iii) an alternative BPA-NI epoxy liner (Company Z). In an embodiment, filled cans may be stored at approximately 20° C. in an upright position and shielded from direct light to simulate ambient storage conditions.

In one exemplary configuration, sampling may occur at defined time intervals corresponding to four-month and eight-month post-packaging periods. For each experimental condition, three replicate cans may be prepared for every combination of wine type (n=5), compositional group (n=3), liner type (n=3), and storage duration (n=2), resulting in a total of 270 individual can samples. In some embodiments, at least a processor 108 may record metadata associated with each can sample, including pH, free $SO_2$, molecular $SO_2$, and liner composition, to facilitate subsequent correlation analysis between formulation parameters and observed $H_2S$ accumulation. At each designated time point, hydrogen sulfide concentration may be quantified in accordance with established gas detection or analytical protocols. In an embodiment, measured $H_2S$ levels may be stored in association with their respective sample identifiers, allowing the predictive compatibility model to map compositional and packaging variables to corresponding stability outcomes. In some embodiments, the results of such analyses may provide training or validation data for simulation models described elsewhere in this disclosure.

In some embodiments, accelerated aging trials may be conducted to simulate long-term beverage-liner interactions within a compressed experimental timeframe. In an exemplary embodiment, test coupons may be prepared from aluminum can bodies using a standardized protocol validated in prior studies. The top and bottom portions of the aluminum cans may be removed using a precision cutting instrument such as a Gryphon C-40 band saw (Gryphon Corporation), after which the cylindrical body section may be vertically cut open using stainless steel shears to yield a flat aluminum sheet. From this sheet, rectangular coupons measuring approximately 1 cm×4 cm may be sectioned from the mid-body region, while two smaller coupons (approximately 1 cm×2 cm each) may be prepared from the head-space region of the can body. These coupon sizes may be selected to maintain a constant liner surface-area-to-solution-volume ratio when introduced into a 27-mL test vial. In some embodiments, any exposed uncoated aluminum edges may be sealed with ethyl vinyl acetate (EVA) hot melt adhesive to prevent edge-related corrosion artifacts during testing.

In an embodiment, accelerated aging trials may be performed to model long-term storage effects by subjecting aluminum-liner interfaces to controlled temperature and oxygen conditions. In one implementation, bottled or kegged wine may be transferred into a sanitized 20-L plastic water cooler that has been pre-rinsed with 70% ethanol. Prior to filling, each wine formulation may be sparged with nitrogen gas until the dissolved oxygen concentration reaches less than approximately 0.1 mg/L, as verified using a trace-level optical oxygen meter (e.g., PreSens Fibox 3 LCD with DP-PSt6 dipping probe). During vial filling, the cooler may be continuously back-filled with nitrogen to minimize oxygen uptake. In some embodiments, each accelerated test sample may be prepared by introducing approximately 25 mL of deoxygenated wine into a 27-mL crimp-top glass vial. The vial may first be purged with two to three drops of liquid nitrogen ($LN_2$) to displace residual atmospheric oxygen. A coated and edge-sealed aluminum coupon may then be immediately immersed in the wine sample. A butyl rubber septum may be positioned atop the vial, allowing approximately 10-15 seconds for excess nitrogen to dissipate, after which the vial may be sealed with a 20-mm aluminum crimp cap. This configuration may replicate the sealed microenvironment of a packaged aluminum beverage container while maintaining experimental control over temperature, oxygen exposure, and liner contact surface. In an embodiment, the sealed vials may be incubated at an elevated temperature (e.g., approximately 50° C.) to accelerate chemical interactions between the beverage matrix and the aluminum liner coating. The aging process may proceed for defined durations such as three days and fourteen days, representing early-stage and extended storage intervals, respectively. Following incubation, each sample may be analyzed for hydrogen sulfide ($H_2S$) accumulation according to the measurement procedures described elsewhere in this disclosure. The accelerated aging configuration may yield total oxygen uptake below approximately 0.5 mg/L $O_2$, as determined by the PreSens optical oxygen meter. Control tests on model wine matrices may confirm negligible oxygen ingress over three-day and fourteen-day incubation periods, ensuring that observed $H_2S$ generation arises primarily from liner-beverage chemical interactions rather than oxygen-driven oxidation pathways.

In some embodiments, accelerated aging tests may be conducted to evaluate the effects of can source, liner chemistry, and within-can sampling location on hydrogen sulfide ($H_2S$) production under controlled conditions. In an exemplary embodiment, a total of ten distinct aluminum beverage can types may be sourced from five commercial suppliers, designated as V, W, X, Y, and Z. The cans may include three bisphenol A (BPA)-based epoxy liners, five bisphenol A-non-intent (BPA-NI) epoxy liners, and two acrylic-based liners. In some embodiments, each can type may be assigned a coded designation reflecting both manufacturer and liner class, such that the letter (V-Z) identifies the can supplier, while the numerical identifier denotes the liner category: “1” for BPA epoxy, “2” for BPA-NI epoxy, and “3” for acrylic. In one embodiment, multiple production batches from certain manufacturers may be included to evaluate batch-to-batch variability in liner formulation and application quality. For instance, identifiers such as X1 and X1-2 may represent two batches of BPA epoxy cans obtained from manufacturer X. Similarly, identifiers such as Y2, Y2-2, and Y2-3 may represent successive production runs of BPA-NI epoxy cans from manufacturer Y, with observable differences in liner uniformity. In one embodiment, visual inspection of the can interiors may reveal incomplete liner coverage for some production batches (e.g., Y2-2), while other batches (e.g., Y2-3) may contain thinner but continuous layers of the same liner material. These variations may serve as experimental factors influencing liner-beverage interactions and $H_2S$ generation potential.

In some embodiments, a single wine formulation may be used across all accelerated aging trials to ensure experimental consistency and control for beverage composition variables. In an exemplary implementation, a commercial 2020 German Riesling may be selected as the test matrix, characterized by a pH of approximately 3.1, a molecular $SO_2$ concentration of approximately 2.56 mg/L, a free $SO_2$ concentration of approximately 43 mg/L, and an alcohol by volume (ABV) of approximately 9.3%. This formulation may be representative of a high-molecular-$SO_2$ beverage composition and thus an ideal candidate for assessing corrosion-prone and reductive environments within aluminum containers. In an embodiment, accelerated aging trials may be conducted at elevated temperature conditions, such as approximately 50° C., for durations of three days and fourteen days. These timepoints may be selected based on prior validation demonstrating that the mean $H_2S$ concentration obtained from three-day and fourteen-day incubations strongly correlates with long-term stability outcomes under real storage conditions. For each experimental treatment, combinations of can type, within-can sampling location, and storage duration may be prepared in triplicate to ensure statistical robustness. In some embodiments, at least a processor 108 may record for each sample the can code, liner type, production batch, surface condition, and incubation parameters, such that $H_2S$ output values can be correlated with both manufacturing and compositional variables for subsequent model training or verification.

In some embodiments, a modified accelerated aging experiment may be employed to evaluate whether immersed and non-immersed regions of an aluminum substrate produce comparable hydrogen sulfide ($H_2S$) concentrations when exposed to a beverage composition under controlled conditions. In an exemplary embodiment, test coupons may be prepared from bisphenol A-non-intent (BPA-NI) epoxy-coated aluminum alloy sheets (e.g., alloy 3004) according to the coupon preparation protocol described previously. The modified experimental design may be configured to isolate the contribution of liquid-phase and vapor-phase exposure to liner degradation and $H_2S$ generation.

In one embodiment, each accelerated aging test may include aluminum coupons inserted into 27-mL glass vials containing a beverage formulation, with the coupons arranged in one of four defined orientations. The orientations may correspond to distinct surface exposure conditions, as follows: (1) a first configuration in which one rectangular coupon (approximately 4 cm×1 cm) is fully submerged within the liquid matrix, and a second, smaller coupon (approximately 1 cm×1 cm) is affixed to the underside of the vial septum using a thermally applied hot-melt adhesive such that the coupon is suspended entirely within the vial headspace; (2) a second configuration in which a single elongated coupon (approximately 5 cm×1 cm) is positioned vertically such that approximately 1 $cm^2$ of its surface area is exposed to the vapor phase, while the remaining portion is immersed in the liquid phase, thereby modeling the interfacial zone of a filled aluminum beverage container; (3) a third configuration in which both a larger coupon (approximately 4 cm×1 cm) and a smaller coupon (approximately 1 cm×1 cm) are positioned fully submerged within the liquid phase to evaluate the reproducibility of submerged surface interactions; and (4) a fourth configuration in which a single coupon (approximately 1 cm×1 cm) is affixed to the underside of the vial septum such that the coupon remains entirely in the vapor phase, with approximately 1 $cm^2$ of its coated surface area exposed to the headspace atmosphere above the liquid.

In some embodiments, these four orientation configurations may collectively permit the differentiation of $H_2S$ generation arising from liquid-contact corrosion mechanisms, interfacial diffusion phenomena, and vapor-phase liner degradation. The configuration in which coupons are partially or fully exposed to the vapor phase may simulate headspace contact surfaces commonly encountered in upright-stored cans, where temperature fluctuations or condensate cycling can accelerate localized reactions. In an embodiment, at least a processor 108 may record sample identifiers, coupon orientation, surface area ratios, and incubation parameters to correlate measured $H_2S$ concentrations with exposure geometry. The resulting dataset may provide structural and chemical insight into whether liner degradation pathways differ between immersed and non-immersed aluminum regions under equivalent accelerated aging conditions.

In some embodiments, hydrogen sulfide ($H_2S$) concentration in beverage samples may be quantified using a colorimetric gas detection system configured to operate in conjunction with a commercial aeration-oxidation (A-O) apparatus. In an exemplary embodiment, the analytical configuration may include a gas detection tube (GDT) assembly designed to selectively capture and indicate gaseous $H_2S$ evolved from a liquid wine sample during aeration. The system may include an A-O unit (e.g., GW Kent, Inc.) connected in series with one or more selective gas detection tubes and a vacuum or aspiration source configured to draw sample vapors through the detection assembly. For purposes of this disclosure, a “gas detection tube” is a sealed, chemically treated glass tube configured to produce a visually detectable color change proportional to the concentration of a specific analyte. In an embodiment, an $H_2S$-selective gas detection tube (e.g., Gastec models 4LT and 4LL, Gastec International) may be positioned between the receiver flask of the A-O apparatus and the vacuum inlet. When a liquid sample is aspirated through the apparatus, $H_2S$ present in the sample may be volatilized and transported through the GDT, where it reacts with a metal salt reagent immobilized on the inner surface of the tube. The resulting reaction produces a visible stain whose length or intensity is proportional to the $H_2S$ concentration in the sample.

In some embodiments, potential interferences from sulfur dioxide ($SO_2$) or other reactive sulfur species may be mitigated through sequential filtration. For example, an $SO_2$-selective gas detection tube (e.g., Gastec model 5L) may be positioned between the A-O outlet and the $H_2S$-selective GDT, thereby absorbing or neutralizing $SO_2$ prior to contact with the $H_2S$ detection medium. This configuration may ensure that only $H_2S$ contributes to the observable stain length, minimizing false-positive readings due to $SO_2$ crossover or reaction product interference. In an embodiment, the calibration of the gas detection tubes may be performed according to manufacturer specifications, correlating stain length (typically in millimeters) to concentration (e.g., μg/L). The A-O apparatus may be configured to maintain a consistent aspiration rate and sample volume to ensure reproducibility. The method may achieve a detection limit of approximately 1 μg/L $H_2S$, as previously established through validation studies. In some embodiments, at least a processor 108 may record the stain length, time of measurement, and calibration reference values, converting the visual indication to a digital concentration record stored in association with the corresponding sample metadata. In further embodiments, the quantified $H_2S$ data may be integrated into the predictive compatibility model as an empirical training parameter representing the degree of reductive sulfur accumulation under specified liner, pH, and $SO_2$ conditions. This may enable refinement of the model's sensitivity to corrosion-mediated sulfur release mechanisms and support enhanced prediction accuracy for real-world packaging stability outcomes.

Figure 2:
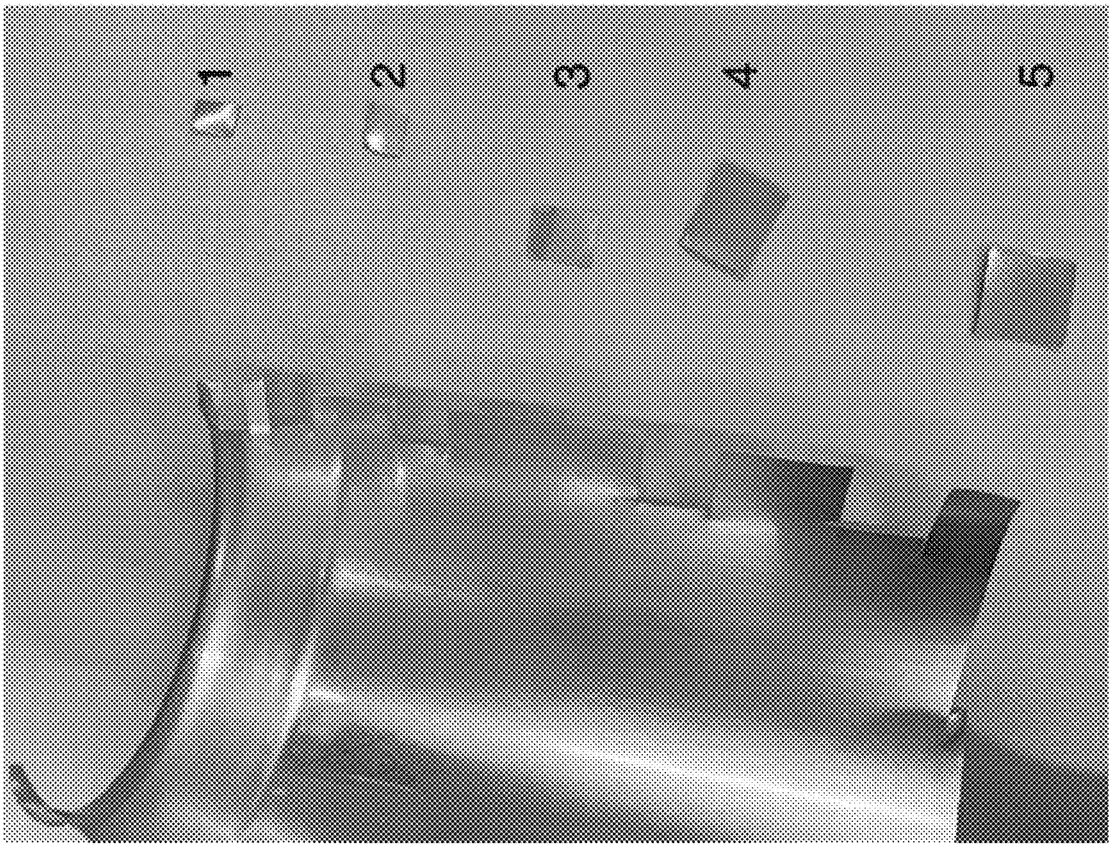
FIG. 2 illustrates a location within a can body sampled for liner and aluminum surface analysis.

Now referring to FIG. 2, illustrates the location within the can body sampled for liner and aluminum surface analysis. In an embodiment, the polymeric liner and aluminum interior surface of cans used in long-term storage trials (e.g., X1, Y2, and Z2) may be evaluated both prior to and following storage using a combination of optical, spectroscopic, and compositional analysis techniques. In some embodiments, unlined aluminum cans provided by manufacturers may also be analyzed to establish baseline elemental and morphological profiles for comparison. The analytical workflow may be configured to detect liner degradation, metal migration, and compositional or structural changes attributable to beverage contact, thereby providing empirical validation data for predictive compatibility modeling.

In an exemplary embodiment, can samples may be prepared for analysis by first sectioning the cylindrical body of each can using a precision cutting instrument such as a Gryphon C-40 band saw (Gryphon Corporation). Each sectioned can may then be vertically cut with stainless steel shears to open the body into a flat rectangular sheet, following the procedure previously described for coupon preparation. For post-storage analysis, the can lid may be removed using a mechanical seam teardown tool (e.g., Oktober Design) to prevent liner tearing and to maintain sample integrity. From each can, multiple test specimens may be obtained from five distinct vertical regions, ranging from the base to the upper headspace region, as illustrated in FIG. 2. In an embodiment, coupons for surface analysis may be approximately 0.25 cm×0.25 cm in size, except for coupons collected from headspace regions where spatial constraints may require smaller samples (approximately 0.25 cm×0.1 cm). These smaller coupons may enable accurate assessment of liner uniformity and corrosion signatures at the curved transition zone near the lid seam. Prior to analysis, sample surfaces may be gently cleaned with inert gas to remove loose particulate matter, ensuring that no additional abrasion or polishing alters the native liner morphology.

In some embodiments, elemental composition of both unused bare aluminum and pre- and post-storage lined can samples may be determined using x-ray fluorescence (XRF) spectroscopy. For purposes of this disclosure, "x-ray fluorescence (XRF)" refers to a non-destructive analytical method in which incident x-rays excite core electrons within a sample, causing emission of characteristic secondary radiation that can be used to quantify elemental composition. In an exemplary implementation, samples approximately 1 cm×1 cm (obtained from FIG. 2, Location 4) may be analyzed using a portable XRF spectrometer (e.g., Bruker Tracer III-SD). Each measurement may be conducted in triplicate, with the excitation voltage set to approximately 40 kV, the tube current set to approximately 40 μA, and a dwell time of approximately 60 seconds per scan.

In one embodiment, the portable XRF unit may be operated in an upward-facing tabletop geometry, allowing samples to be positioned directly on the measurement window with the inner surface of the can facing the detector aperture. Spectral data may be collected under ambient laboratory conditions and analyzed using spectral-fitting software such as PyMCA to quantify element-specific peak areas. In some embodiments, the resulting spectra may be used to determine the presence and concentration of key alloy components (e.g., aluminum, magnesium, manganese, and iron) as well as trace elements indicative of liner degradation or beverage-induced corrosion (e.g., tin, copper, zinc, or sulfur residues). In further embodiments, XRF compositional profiles obtained before and after storage may be compared to identify changes in elemental abundance correlated with beverage exposure. Such comparative analysis may reveal evidence of liner delamination, diffusion of metallic ions through the coating, or loss of protective barrier components. In some embodiments, at least a processor may correlate detected elemental shifts with $H_2S$ accumulation data or corrosion risk scores generated by the predictive compatibility model, thereby enabling quantitative linkage between empirical material characterization and simulated packaging stability outcomes.

With continued reference to FIG. 2, in some embodiments, the composition and physical characteristics of the can liner and underlying aluminum substrate may be characterized using a combination of spectroscopic, optical, and electrochemical measurement techniques. These methods may be applied both to pre-storage and post-storage samples to assess liner degradation, compositional changes, adhesion integrity, and metal exposure. In an exemplary implementation, analysis may be performed on lined aluminum beverage cans of types X1, Y2, and Z2, as well as unlined aluminum control samples provided by the manufacturer.

In some embodiments, Fourier transform infrared-attenuated total reflectance (FTIR-ATR) spectroscopy may be employed to characterize the chemical composition of polymeric liner materials. For purposes of this disclosure, "FTIR-ATR" refers to a spectroscopic technique in which infrared radiation is directed through an optically transparent crystal at a shallow angle to induce total internal reflection, allowing the evanescent field to interact with the liner surface and yield absorbance spectra representative of molecular functional groups. In one embodiment, spectra may be collected using a Bruker Vertex V80V Vacuum FTIR system operated under a nitrogen atmosphere (Cornell Center for Materials Research, Ithaca, NY). Coupons approximately 0.5 cm×0.5 cm in size may be prepared in triplicate from the mid-body region of each can (corresponding to FIG. 2, Location 4). Spectral data may be collected across a wavelength range of approximately 4000 to 700 $cm^{-1}$. In some embodiments, the acquired FTIR-ATR spectra may be analyzed to identify characteristic absorbance bands corresponding to epoxy, polyester, or acrylic resin constituents, thereby confirming liner composition and detecting chemical shifts associated with beverage exposure or oxidation.

In some embodiments, liner thickness and aluminum surface uniformity may be profiled using laser-scanning profilometry. For purposes of this disclosure, "laser-scanning profilometry" refers to a non-contact optical method that reconstructs a three-dimensional surface topography by measuring the reflected intensity of a focused laser beam scanned across a defined area. In an exemplary embodiment, measurements may be conducted using a Keyence VK-X260 laser-scanning profilometer at a laser wavelength of approximately 408 nm. Each sample may be analyzed using the "surface profile" mode to evaluate substrate smoothness and the "thin film" mode to determine liner coating thickness and uniformity. A refractive index of approximately 1.7 may be applied for BPA and BPA-NI epoxy liners, extrapolated from the known polycarbonate refractive index in the 435-1052 nm range. The measured field of view may be approximately 285 μm×210 μm, allowing micro-scale visualization of coating uniformity and potential micro-defects.

In some embodiments, liner thickness in both the body and dome regions of cans may additionally be determined using optical interferometry. For purposes of this disclosure, "optical interferometry" refers to a precision technique that measures film thickness by analyzing interference patterns produced by the reflection of broadband light from layered surfaces. In an exemplary embodiment, an interferometric film-thickness analyzer (e.g., SpecMetrix ACS-10, Sensory Analytics LLC) may be used across a spectral range of approximately 700-1400 nm, with a refractive index of approximately 1.55 applied for computational modeling. Three cans of each liner type may be sampled, and data may be used to quantify mean liner thickness, inter-sample variation, and coating distribution between structural regions of the can. In further embodiments, electrochemical impedance spectroscopy (EIS) may be employed to evaluate liner integrity, including the presence of pores, coating continuity, and barrier performance. For purposes of this disclosure, "EIS" refers to an electrochemical measurement technique in which a sinusoidal voltage perturbation is applied to a sample immersed in an electrolyte, and the resulting current response is analyzed to determine impedance characteristics over a range of frequencies. In an exemplary configuration, EIS measurements may be conducted in triplicate using a PalmSens3 potentiostat with PSTrace 5.9 software. Intact, unused lined cans may be analyzed directly (rather than isolated coupons) following established protocols. The experimental setup, shown in FIG. 16, may include a working electrode in contact with the exterior can bottom, a counter electrode consisting of a flat steel cell, and a silver/silver chloride (Ag/AgCl) reference electrode immersed in a 35 g/L sodium chloride (NaCl) electrolyte solution. The system may be housed within a Faraday cage to prevent electromagnetic interference. The open circuit potential (OCP) may be stabilized prior to measurement (drift <0.01 mV/sec). The applied potential, frequency sweep parameters, and equivalent circuit modeling conditions may be defined according to FIGS. 11 and 12.

In some embodiments, metal exposure measurements may be performed using an enamel rater (e.g., WACO Enamel Rater III). For purposes of this disclosure, an "enamel rater" is an industry-standard instrument configured to measure coating porosity by quantifying current flow through exposed metal regions under an applied voltage. In an exemplary test, cans may be filled with a 10 g/L NaCl electrolyte solution to a standardized level, and a stainless-steel probe electrode may be immersed within the can. A potential of approximately 6.3 V may be applied for four seconds, after which the resulting current may be recorded. The measured current may provide a quantitative indication of liner coverage, with higher current values corresponding to greater exposed metal area. Three cans of each type from the long-term storage study may be analyzed to compare coating integrity across liner chemistries. In some embodiments, liner adhesion quality may be evaluated using standardized mechanical testing. For example, adhesion testing may be performed in accordance with ASTM D3359-17, Test Method B. For purposes of this disclosure, "liner adhesion quality" refers to the mechanical robustness of the liner-to-substrate bond under applied shear or peel stress. In an exemplary test, six parallel horizontal and six parallel vertical incisions may be made on the interior can surface using a precision cutting tool to form a crosshatch pattern. A pressure-sensitive adhesive tape (e.g., Scotch Bi-Directional Filament Tape 8959, 180° peel strength of approximately 11 N/cm) may then be applied to the incised area. After 90 seconds of dwell time, the tape may be peeled off and the percentage of removed coating area may be quantified, providing a measure of liner adhesion strength. In additional embodiments, the presence of uncoated or exposed metal regions may be evaluated qualitatively using the ASBC Can Method 8. For purposes of this disclosure, "uncoated region detection" refers to the identification of areas where the liner coating is absent or discontinuous, exposing the aluminum substrate. In an exemplary test, an aqueous solution containing hydrochloric acid (0.027 N) and copper sulfate pentahydrate (100 g/L) may be added to cans (n=3 replicates) and maintained at room temperature for approximately 45 minutes. Uncoated regions may be visually identified by the formation of copper deposits on exposed aluminum areas, indicating liner discontinuity or manufacturing defects.

In some embodiments, analytical outputs obtained from FTIR-ATR, profilometry, interferometry, EIS, and enamel rating measurements may be stored within a unified characterization dataset. At least a processor may be configured to correlate this dataset with corresponding $H_2S$ production data or liner compatibility scores, enabling the system to refine its predictive modeling parameters based on empirical liner performance metrics. This integration may further improve the accuracy of liner-formulation compatibility simulations by linking measurable physical degradation indicators to computational risk outputs.

In some embodiments, statistical analysis of experimental data may be performed using commercial statistical software packages, such as JMP Pro 16 or JMP Pro 17 (SAS Institute, Inc.). For purposes of this disclosure, "statistical analysis" refers to the application of quantitative and inferential statistical methods to evaluate the significance of observed effects across experimental variables, including liner composition, storage duration, and beverage formulation parameters. In an exemplary embodiment, analysis of variance (ANOVA) may be employed to determine whether mean hydrogen sulfide ($H_2S$) concentrations differ significantly among treatment groups. The analysis may be configured with a significance level (a) of approximately 0.05, such that p-values less than 0.05 are interpreted as statistically significant. In some embodiments, ANOVA results may be complemented by post hoc comparison tests or least significant difference (LSD) analyses to further resolve differences between specific liner types, storage intervals, or wine compositions. In certain implementations, at least a processor may be configured to ingest raw data values corresponding to $H_2S$ concentration, liner characterization metrics, and formulation variables, and to perform automated statistical modeling within a data analysis module. The processor may compute confidence intervals, variance components, and p-values, and may generate visual or tabular outputs summarizing statistical trends. The results of the analysis may then be stored as structured statistical data objects and integrated into the system's predictive modeling framework to iteratively refine model weighting factors or validation criteria based on empirical evidence.

Figure 3:
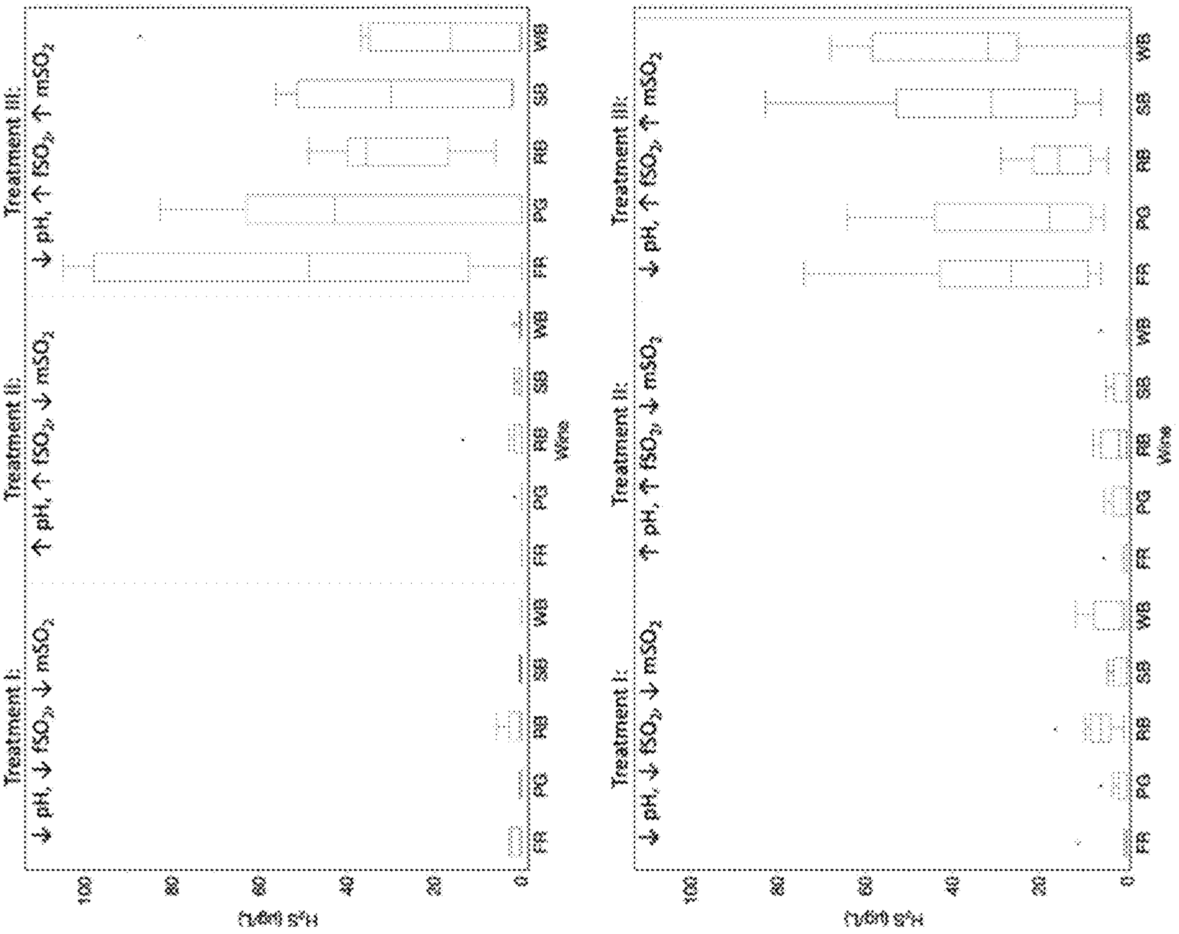
FIG. 3 is a graphical representation of hydrogen sulfide ($H_2S$) production by treatment group and wine after four months (top) and eight months (bottom)

With reference now to FIG. 3, a graphical representation of hydrogen sulfide ($H_2S$) production by treatment group and wine after four months (top) and eight months (bottom) is illustrated. In some embodiments, empirical results from long-term storage trials demonstrate that hydrogen sulfide ($H_2S$) accumulation in canned wines varies as a function of liner composition, wine chemistry, and molecular sulfur dioxide ($SO_2$) concentration. Earlier investigations involving isolated aluminum coupons and single wine formulations suggested that $H_2S$ formation was elevated in acrylic-lined cans relative to epoxy-lined cans, and that molecular $SO_2$ was a stronger predictor of $H_2S$ generation than either free $SO_2$ or pH alone. However, those prior studies were limited to short-term accelerated conditions and single-source liners. The present disclosure extends those findings by evaluating multiple commercial wine types and multiple liner sources under extended storage conditions, thereby confirming and refining the relationship between wine chemistry and gas evolution in sealed aluminum containers.

In an exemplary embodiment, five commercial wines, Pinot Grigio, Sauvignon Blanc, French Rosé, Sparkling Rosé, and Sparkling White, were each adjusted to yield three distinct treatment groups characterized by varying combinations of pH, free $SO_2$, and molecular $SO_2$ levels. Specifically, Treatment I represented low-pH, low-free-$SO_2$, and low-molecular-$SO_2$ conditions; Treatment II represented high-pH, high-free-$SO_2$, and low-molecular-$SO_2$ conditions; and Treatment III represented low-pH, high-free-$SO_2$, and high-molecular-$SO_2$ conditions. Additional theoretical combinations could not be produced due to the dependent relationship between molecular $SO_2$ and hydrogen ion concentration, as molecular $SO_2$ is a function of both free $SO_2$ and $[H^+]$. The "high" molecular $SO_2$ range tested (approximately 1.6-2.6 mg/L) may correspond to approximately 0.8-2.0 mg/L when expressed under conventional water-based dissociation constants, given ethanol-adjusted pKa correction factors. In some embodiments, wines corresponding to each treatment may be sealed in cans from three commercial suppliers, designated $X_1$ (BPA-epoxy), $Y_2$ (BPA-NI epoxy), and $Z_2$ (BPA-NI epoxy), and stored under controlled conditions at approximately 20° C. for extended durations. Hydrogen sulfide levels may then be quantified at predetermined intervals (e.g., four and eight months) as depicted in FIG. 3.

In one embodiment, the unadjusted Treatment I wines exhibited non-detectable or trace $H_2S$ concentrations ($<3$ μg/L) immediately following canning, with mean values below the sensory threshold ($<10$ μg/L) at both the four- and eight-month timepoints. In contrast, adjusted wines in Treatment III (high molecular $SO_2$) produced significantly higher $H_2S$ concentrations than Treatment I or II wines (analysis of variance, $p<0.05$). After four months of storage, the average $H_2S$ concentration in Treatment III samples was approximately 28.7 μg/L, with some samples exceeding 100 μg/L. By comparison, Treatments I and II averaged approximately 2.2 μg/L over the same interval. After eight months, similar trends were observed, as illustrated in FIG. 3 (bottom), wherein Treatment III wines maintained the highest $H_2S$ accumulation, indicating that elevated molecular $SO_2$, rather than free $SO_2$ concentration alone, remains a principal driver of $H_2S$ formation under long-term storage conditions. The measured $H_2S$ concentrations in these treatments, particularly for Treatment III, substantially exceeded levels previously observed in bottled wines (≤6 μg/L) and surpassed typical sensory detection thresholds (~1 μg/L).

Without being bound by theory, it is believed that the neutral molecular $SO_2$ fraction may permeate the non-polar liner interface and undergo chemical reduction upon contact with the aluminum substrate, leading to $H_2S$ formation and potential liner degradation. Because molecular $SO_2$ represents a component of total free $SO_2$ and its relative abundance increases at lower pH, the observed effect likely reflects an interactive relationship between $SO_2$ speciation and acidity rather than an independent molecular $SO_2$ mechanism. No statistically significant correlations were observed between $H_2S$ accumulation and other compositional parameters, including alcohol content, titratable acidity, dissolved aluminum, or residual sugar, as summarized in FIG. 10 ($p>0.05$, one-way ANOVA for all factors). These findings collectively confirm that (i) molecular $SO_2$ exerts the dominant influence on $H_2S$ generation during long-term aluminum can storage, (ii) liner chemistry modulates the rate and extent of gas evolution, and (iii) compositional parameters not associated with $SO_2$ speciation contribute minimally under the tested conditions.

In some embodiments, the experimental data represented in FIG. 3 may be stored in a compatibility modeling dataset accessible to at least a processor for validation of liner-beverage predictive models. The processor may compute correlation coefficients, regression weights, or feature-importance values linking liner composition and beverage parameters with observed $H_2S$ concentrations. The resulting model may thereby enable automated prediction of liner-formulation compatibility and long-term storage stability across diverse wine matrices.

Figure 4:
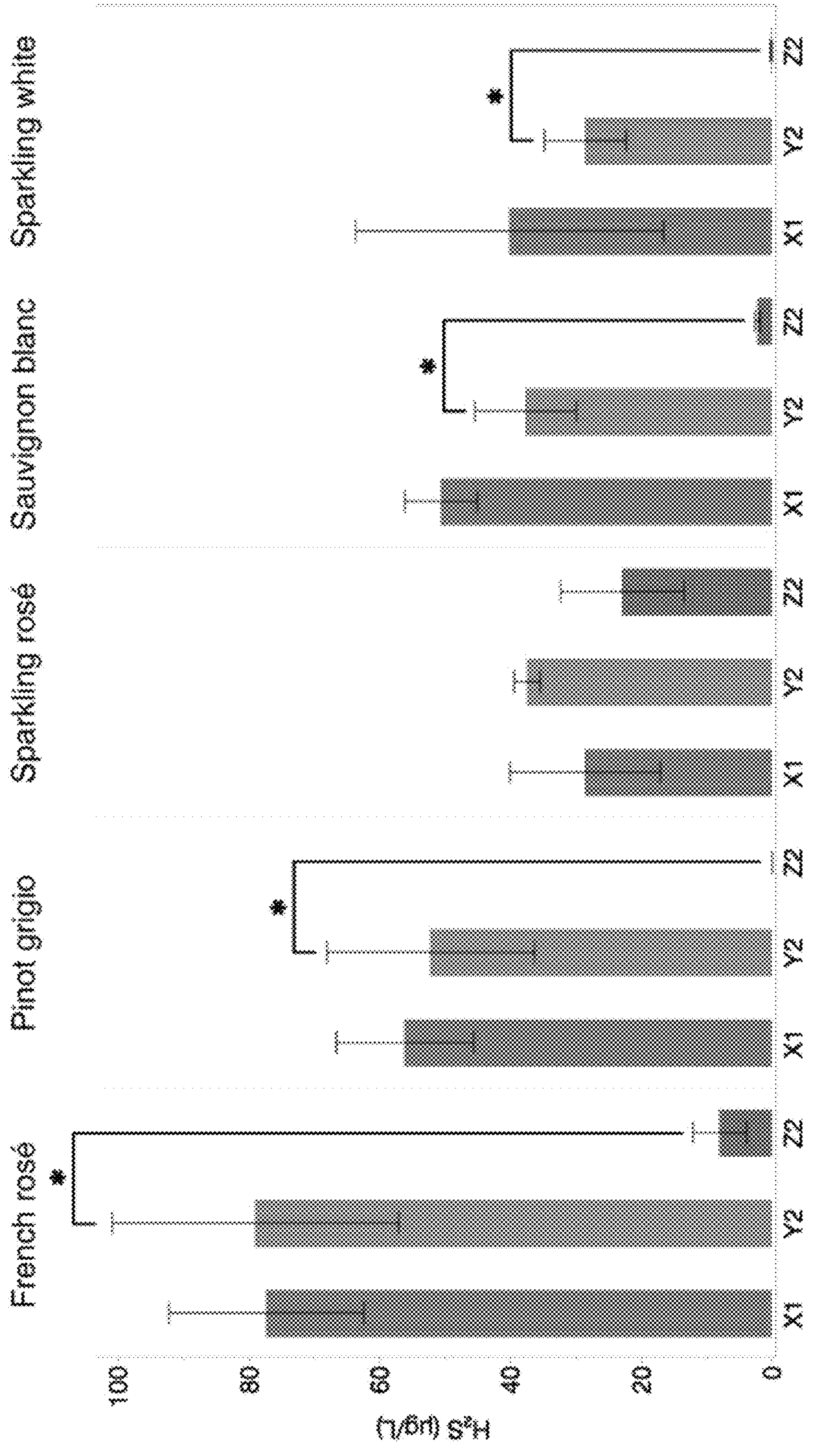
FIG. 4 is a graphical representation of hydrogen sulfide ($H_2S$) production by liner (X1, Y2, and Z2) for each of five Treatment III wines after four months of storage.

With reference now to FIG. 4, a graphical representation of hydrogen sulfide ($H_2S$) production by liner (X1, Y2, and Z2) for each of the five Treatment III (high molecular $SO_2$) wines after four months of storage is illustrated. In some embodiments, the long-term storage data may further be analyzed to evaluate liner-specific effects on hydrogen sulfide ($H_2S$) production across different wine compositions. The results for wines corresponding to Treatment III (high molecular $SO_2$ conditions) stored in three different liner types are illustrated in FIG. 4. In one embodiment, cans designated $Z_2$ (BPA-NI epoxy) exhibited markedly lower mean $H_2S$ concentrations (approximately 5.9 μg/L±2.1) compared to cans designated $X_1$ (BPA epoxy) and $Y_2$ (BPA-NI epoxy) (mean=36.6 μg/L±3.2; two-way ANOVA, $p<0.05$). These data indicate that, even within similar chemical liner classes, manufacturer-specific implementation variables may contribute substantially to corrosion-driven sulfur gas evolution.

In some embodiments, the observed differences between $Y_2$ and $Z_2$ cans may be attributed to manufacturing variability, despite the reported use of an identical liner formulation (e.g., Valspar V70 BPA-NI epoxy). Such variability may include differences in polymer cross-linking, cure kinetics, or application thickness, all of which may influence the permeability of the liner to reactive sulfur species and the local electrochemical environment at the metal-liner interface. Notably, $Z_2$ cans also produced less $H_2S$ than $X_1$ cans, even though $X_1$ utilized a conventional BPA-epoxy liner traditionally considered the industry "gold standard." Statistical variance analysis (Levene's test, $p<0.05$) demonstrated that $Z_2$ cans not only yielded lower mean $H_2S$ concentrations but also exhibited significantly lower inter-replicate variance compared to either $X_1$ or $Y_2$ cans. Reduced variance may indicate greater liner application consistency or enhanced uniformity of the coating thickness across can surfaces, suggesting that manufacturing process control exerts a measurable influence on the reproducibility of chemical stability outcomes.

In prior literature, variation in $H_2S$ production among canned wines has often been high (relative standard deviation exceeding 50%), even when cans were sourced from a single manufacturer. The present findings suggest that can-to-can variability, potentially arising from fluctuations in liner deposition thickness, adhesion, or cure temperature, may represent a significant unaccounted factor influencing gas formation rates. Such variability has been similarly implicated in beverage-can corrosion studies. In some embodiments, at least a processor may be configured to receive and normalize $H_2S$ concentration data and liner-specific parameters (e.g., liner thickness, curing conditions, or surface microdefects) into a structured compatibility dataset. The processor may then compute correlation coefficients or perform regression modeling to quantify the relative contribution of manufacturing variation to observed gas formation outcomes. The resulting correlation outputs may be stored as liner manufacturing performance indicators, thereby enabling subsequent predictive modules to assign confidence intervals or risk scores to candidate liner sources.

In certain implementations, the time-dependent trend observed in the low-$SO_2$ control wines (Treatment I) may further corroborate liner influence. Specifically, cans designated $X_1$ produced the highest $H_2S$ concentrations in Treatment I control samples (ANOVA, $p=0.029$;

data not shown), with incremental increases in $H_2S$ from four to eight months of storage. This pattern suggests that even under low-reactivity conditions, liner chemistry and manufacturing quality may contribute to baseline $H_2S$ accumulation rates. Accordingly, the data depicted in FIG. 4 collectively demonstrate that liner-to-liner and manufacturer-to-manufacturer variations have a statistically significant effect on $H_2S$ formation kinetics. These results may be used to refine compatibility thresholds within the predictive model described herein, enabling the system to recommend optimal liner sources or production batches for specific beverage formulations.

Figure 5:
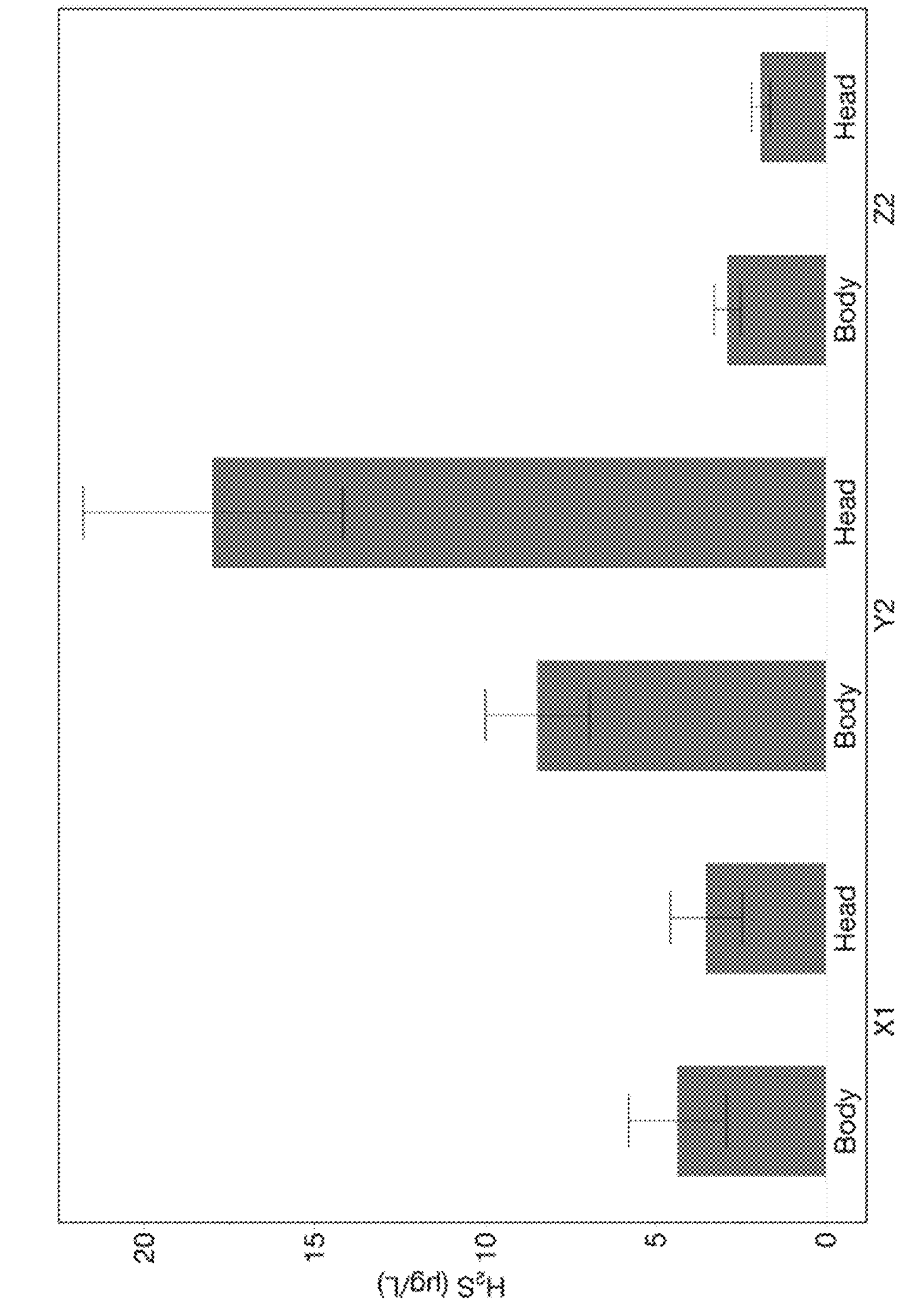
FIG. 5 is a graphical representation of hydrogen sulfide ($H_2S$) production from can body and headspace coupons from three different batches of cans (X1, Y2, Z2), using an accelerated aging assay in triplicate, measuring at three and 14 days of storage.

With reference now to FIG. 5, a graphical representation of hydrogen sulfide ($H_2S$) production from can body (see FIG. 2, Location 4) and headspace (see FIG. 2, Locations 1 and 2) coupons from three different batches of cans (X1, Y2, Z2), using the accelerated aging assay in triplicate (technical replicates), measuring at three and 14 days of storage is illustrated. in some embodiments, accelerated corrosion and hydrogen sulfide ($H_2S$) formation may vary between distinct structural regions of an aluminum beverage can. Prior studies have indicated that cans exhibiting higher $H_2S$ accumulation during long-term storage also display greater visible corrosion, suggesting a correlation between gas evolution and liner degradation. Although visible corrosion was not quantitatively scored in the present investigation, qualitative observations revealed region-specific variation among can sources. For example, cans designated $X_1$ exhibited visible corrosion predominantly along the body wall, whereas cans designated $Y_2$ exhibited corrosion concentrated near the upper neck and headspace region (see FIG. 17).

To evaluate whether such spatial differences reflect variable susceptibility to corrosion, coupons were prepared from the headspace neck region (corresponding to FIG. 2, Locations 1 and 2) and from the body sidewalls (corresponding to FIG. 2, Location 4). The coupons were incubated in a commercial Riesling wine under accelerated aging conditions (approximately three days at 50° C.). As illustrated in FIG. 5, $H_2S$ formation was greatest for the headspace-region coupons of the $Y_2$ can type, producing approximately three-fold higher $H_2S$ concentrations than coupons sourced from the can body. This observation is consistent with the visually evident corrosion near the upper neck region of the $Y_2$ cans.

Without being bound by theory, it is believed that regional differences in liner adhesion, coating thickness, or local curing temperature during manufacture may contribute to the observed heterogeneity in corrosion resistance. However, given that the total surface area of the can body is an order of magnitude greater than that of the neck region, localized corrosion alone is unlikely to account for global differences in $H_2S$ accumulation across liner types or manufacturers. Accordingly, liner uniformity and chemical barrier quality remain more predictive factors for system-wide compatibility assessment.

Figure 6:
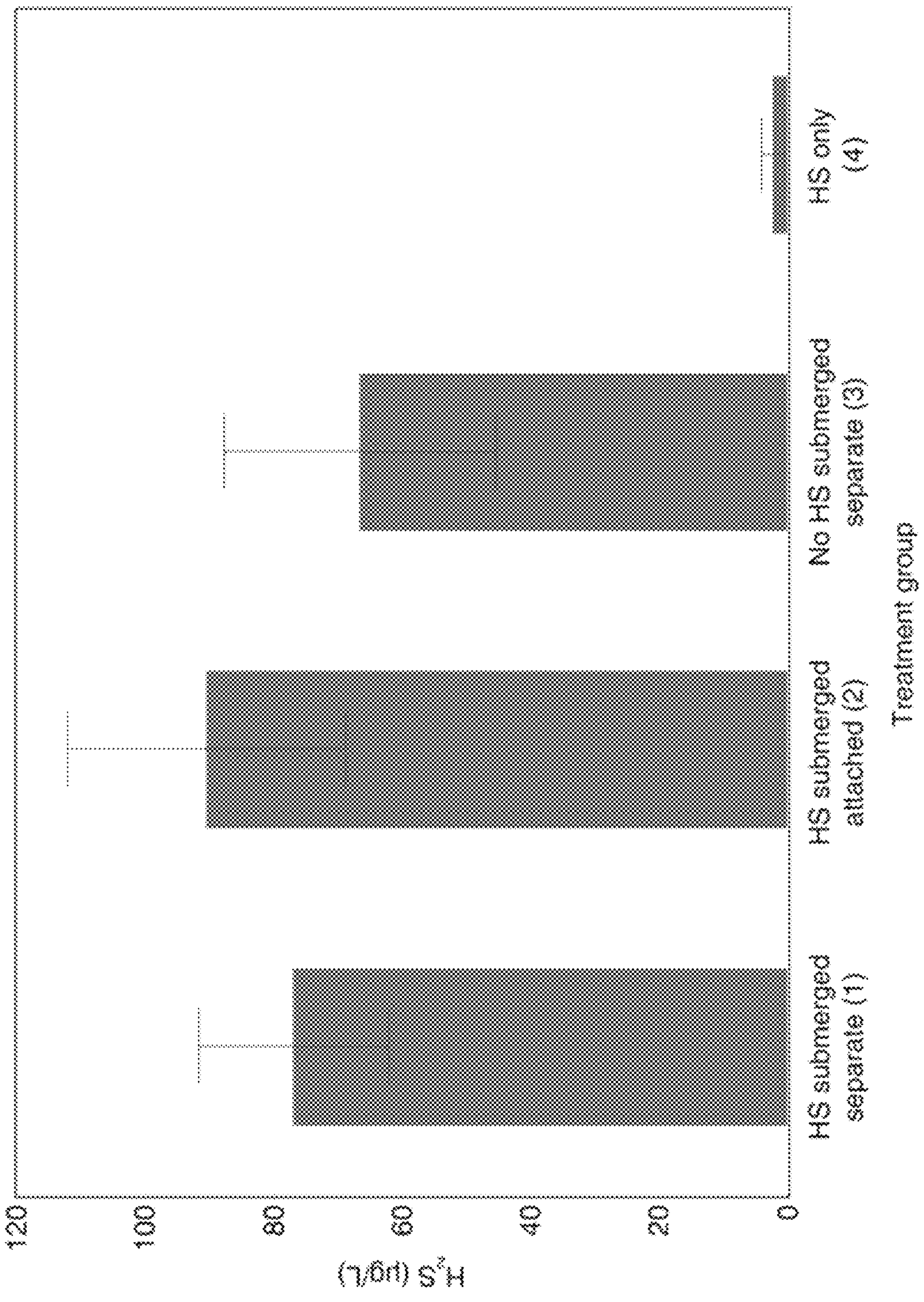
FIG. 6 is a graphical representation of dependence of hydrogen sulfide ($H_2S$) formation on location of coated aluminum coupon.

Referring now to FIG. 6, a graphical representation of dependence of hydrogen sulfide ($H_2S$) formation on location of coated aluminum coupon (headspace [HS] versus immersed) is illustrated. Treatment 1, two coupons, one in headspace and one immersed; Treatment 2, one intact coupon, partially in headspace and partially immersed; Treatment 3, two coupons, both immersed; and Treatment 4, coupon in HS only is illustrated. To further examine whether corrosion and $H_2S$ production differ between immersed and non-immersed aluminum regions, an additional accelerated aging protocol was conducted wherein the spatial orientation of aluminum coupons was systematically varied. As shown in FIG. 6, negligible $H_2S$ formation occurred when aluminum was present exclusively in the headspace (non-immersed), indicating that generation of $H_2S$ through the reduction of $SO_2$ requires direct liquid contact. Similarly, no statistically significant increase in $H_2S$ concentration or visible corrosion was detected when comparing fully immersed coupons (Treatment III) to partially immersed coupons (Treatments I and II), demonstrating that immersion depth alone does not materially affect reaction kinetics under these conditions. Accordingly, the higher corrosion observed in the neck region of certain liners (e.g., Y2) is attributed to reduced coating integrity or localized barrier defects rather than to increased chemical reactivity in vapor-phase regions. In some embodiments, these findings may be used to update the predictive compatibility model, wherein at least a processor may incorporate spatial corrosion weighting factors or liner-uniformity coefficients into the compatibility scoring routine. This enables the system to simulate region-specific degradation behavior and to predict cumulative $H_2S$ formation based on liner composition, coating thickness mapping, and surface area normalization.

Figure 7:
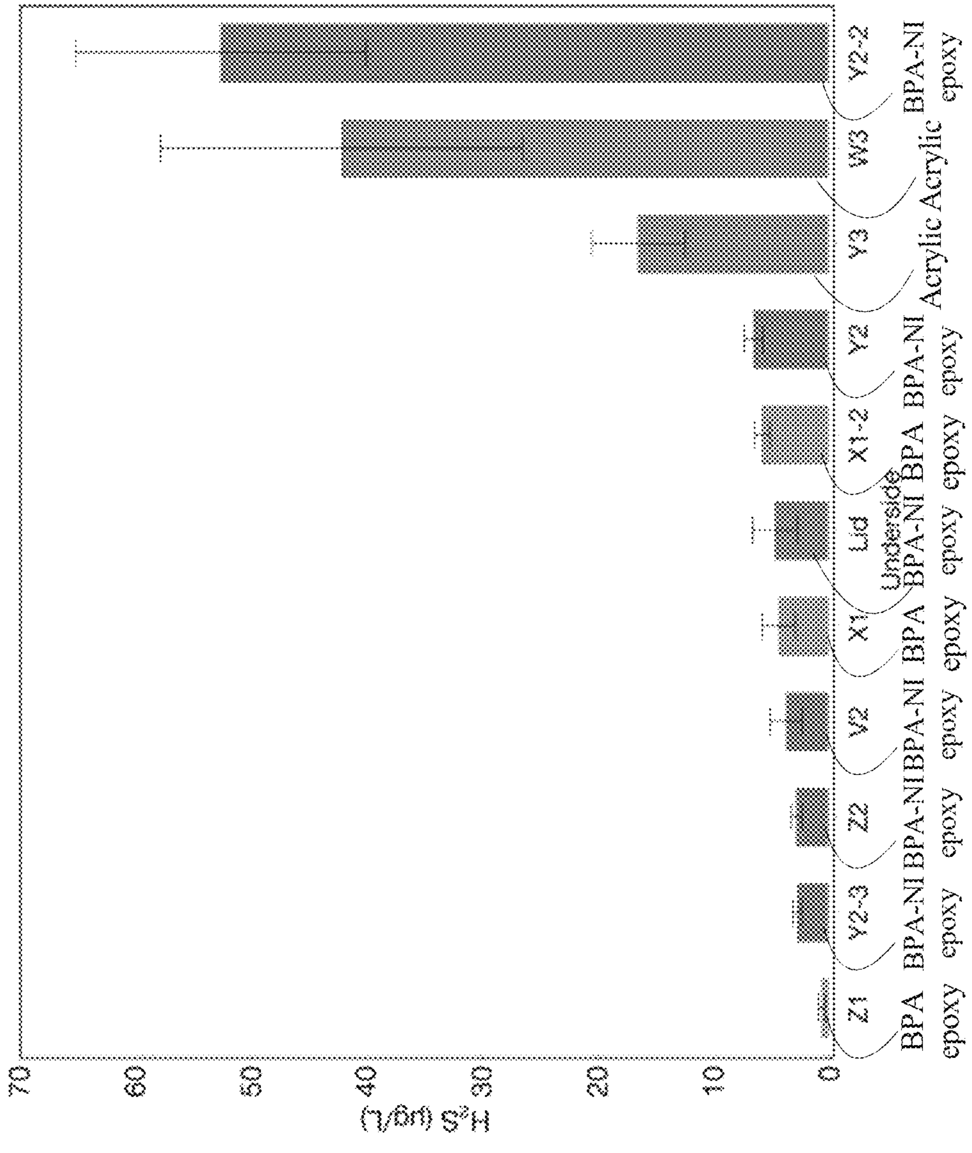
FIG. 7 is a graphical representation of hydrogen sulfide ($H_2S$) production for 10 different can types, as well as an underside of the can lid, after three days in accelerated aging conditions with a commercial German Riesling.

With reference now to FIG. 7, a graphical representation of hydrogen sulfide ($H_2S$) production for 10 different can types, as well as the underside of the can lid, after three days in accelerated aging conditions with a commercial German Riesling is illustrated. In some embodiments, accelerated aging trials may be conducted to further evaluate hydrogen sulfide ($H_2S$) formation across a plurality of liner types and can manufacturers. The accelerated aging protocol may allow controlled evaluation of corrosion-driven gas evolution independent of long-term storage variables such as temperature cycling, light exposure, or headspace gas exchange. In one embodiment, coupons were prepared from cans used in the long-term study described above, designated X1, Y2, and Z2, together with coupons from seven additional liner treatments, yielding a total of ten test configurations. Each coupon was incubated in a single commercially available German Riesling characterized by a high molecular $SO_2$ concentration, thereby standardizing the beverage chemistry across all test groups.

As illustrated in FIG. 7, in some embodiments, $H_2S$ formation under accelerated conditions may vary significantly among liner compositions and manufacturing sources. Consistent with previous findings, acrylic-coated coupons generated substantially higher $H_2S$ concentrations, up to approximately 100 μg/L, than other liner types, with the exception of the $Y_2$-2 batch (Tukey test, $p<0.05$). By comparison, epoxy and BPA-NI epoxy liners generally exhibited lower $H_2S$ generation, reinforcing the observed correlation between polymer chemistry and corrosion protection performance.

In certain embodiments, variation in $H_2S$ formation may also be detected among different manufacturers producing liners nominally classified under the same polymer category. For example, coupons corresponding to Z2 generated significantly lower $H_2S$ concentrations than all three Y2 batches (ANOVA, $p<0.05$), and coupons corresponding to Z1 generated lower concentrations than X1 (ANOVA, $p<0.05$). These findings demonstrate that liner formulation alone is not predictive of stability outcomes, and that manufacturing variables such as curing conditions, cross-linking density, and surface uniformity can produce measurable chemical divergence even when nominal liner chemistries are identical. Similar inter-manufacturer variability was observed among acrylic coatings sourced from different producers (e.g., Y3 and W3), which exhibited statistically distinct mean $H_2S$ values and elevated within-group variance (Levene's test, $p<0.05$). This result suggests that polymer homogeneity and process consistency during liner deposition materially affect barrier integrity and gas evolution behavior. In some embodiments, such process-linked data may be captured by at least a processor as part of a structured liner-performance dataset, enabling machine-learning-based association between manufacturer-specific process metrics and observed chemical stability outcomes. Batch-to-batch variation was also observed among cans designated Y2, wherein the defective lot Y2-2 produced approximately ten-fold higher $H_2S$ than either the original batch (Y2) or thinner-coated variant (Y2-3). The visually defective Y2-2 cans displayed surface irregularities and incomplete coating in the moat region (see FIG. 18), which likely contributed to elevated reactivity and reduced corrosion resistance. These results confirm that localized liner defects, particularly in high-stress forming regions of the can, can amplify reductive gas generation independent of overall polymer chemistry.

In one or more embodiments, the system may employ the results shown in FIG. 7 to derive manufacturing consistency scores or defect-risk parameters. At least a processor may compute weighted stability indices for each liner source based on accelerated aging data, variance magnitude, and observed defect frequency. These indices may be integrated into the predictive compatibility model as confidence factors for downstream liner-selection algorithms. By aggregating defect-linked chemical outcomes from multiple production lots, the disclosed system provides a scalable framework for correlating manufacturing variability with beverage stability and for recommending liner suppliers based on verified performance consistency.

Figure 8:
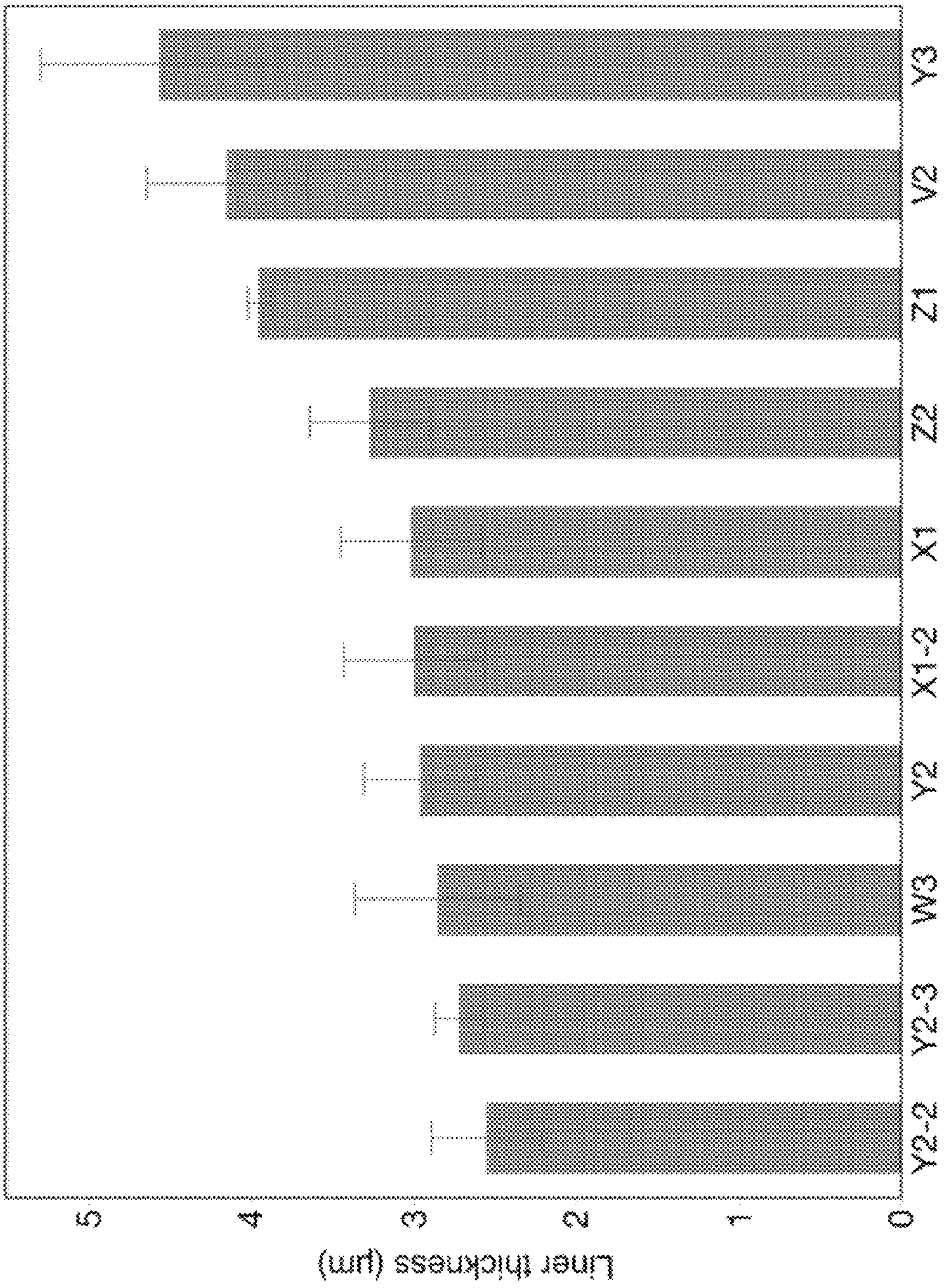
FIG. 8 is a graphical representation of can body liner thickness from 10 different can types, as measured by laser-scanning profilometer.

With reference now to FIG. 8, a graphical representation of can body liner thickness from 10 different can types, as measured by laser-scanning profilometer (n=3 cans per liner type) is illustrated. In some embodiments, the system may utilize characterization data associated with the polymeric liner and underlying aluminum substrate to identify structural or compositional features that contribute to variation in hydrogen sulfide ($H_2S$) formation. Prior experimental work demonstrated that liner chemistry is a principal determinant of gas formation, with acrylic liners yielding more than ten-fold higher $H_2S$ concentrations than epoxy-based liners. However, both long-term and accelerated-aging results of the present study revealed comparable variation among cans employing nominally identical liner chemistries but sourced from different manufacturers. Accordingly, variation in performance (including average $H_2S$ formation and can-to-can variance) was hypothesized to originate from one or more of the following: aluminum alloy composition, polymeric liner formulation, degree of polymer cross-linking or cure, and liner thickness and uniformity.

Figure 19:
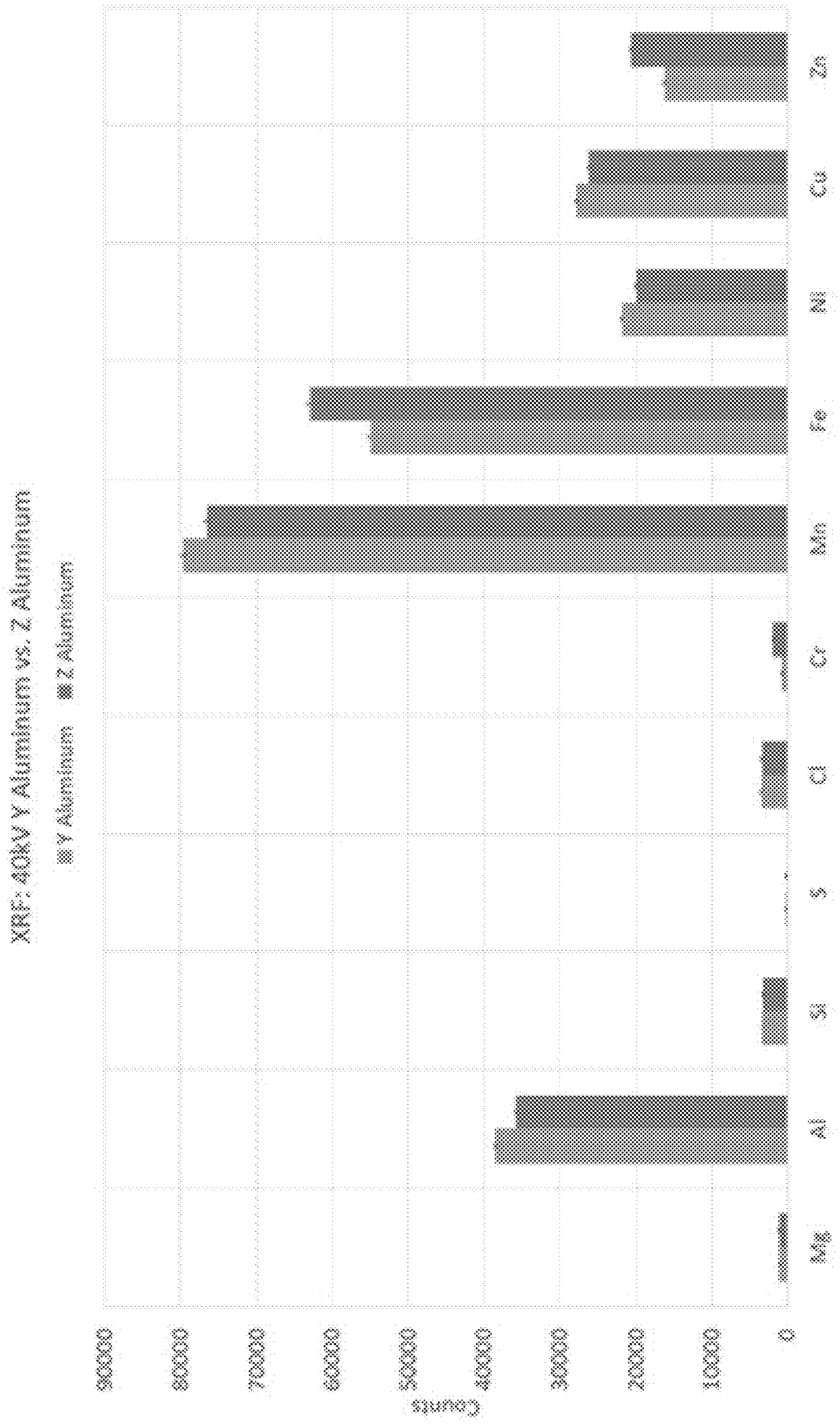
FIG. 19 illustrates an elemental analysis by x-ray fluorescence (XRF) for Y2 and Z2 cans.

In one embodiment, the aluminum alloy compositions of the BPA-NI epoxy can bodies produced by manufacturers Y and Z were analyzed via X-ray fluorescence (XRF) spectroscopy, as shown in FIG. 19. These sources were selected because they employed the same nominal liner chemistry, thereby isolating alloy composition as a variable. Results were semi-quantitative, as calibration standards were not included. Among detected elements, only chromium (Cr) exhibited variation exceeding 20%, with the Z series containing approximately three-fold higher Cr than Y. Given that Cr is typically present in the Al 3004 alloy at concentrations below 0.05%, this difference was unlikely to materially influence $H_2S$ evolution. Other trace elements such as copper (Cu), which in its soluble Cu(II) state can complex with or sequester sulfide species, showed differences below 20%, further suggesting that bulk alloy composition alone does not explain the observed variability in $H_2S$ accumulation.

Figure 20:
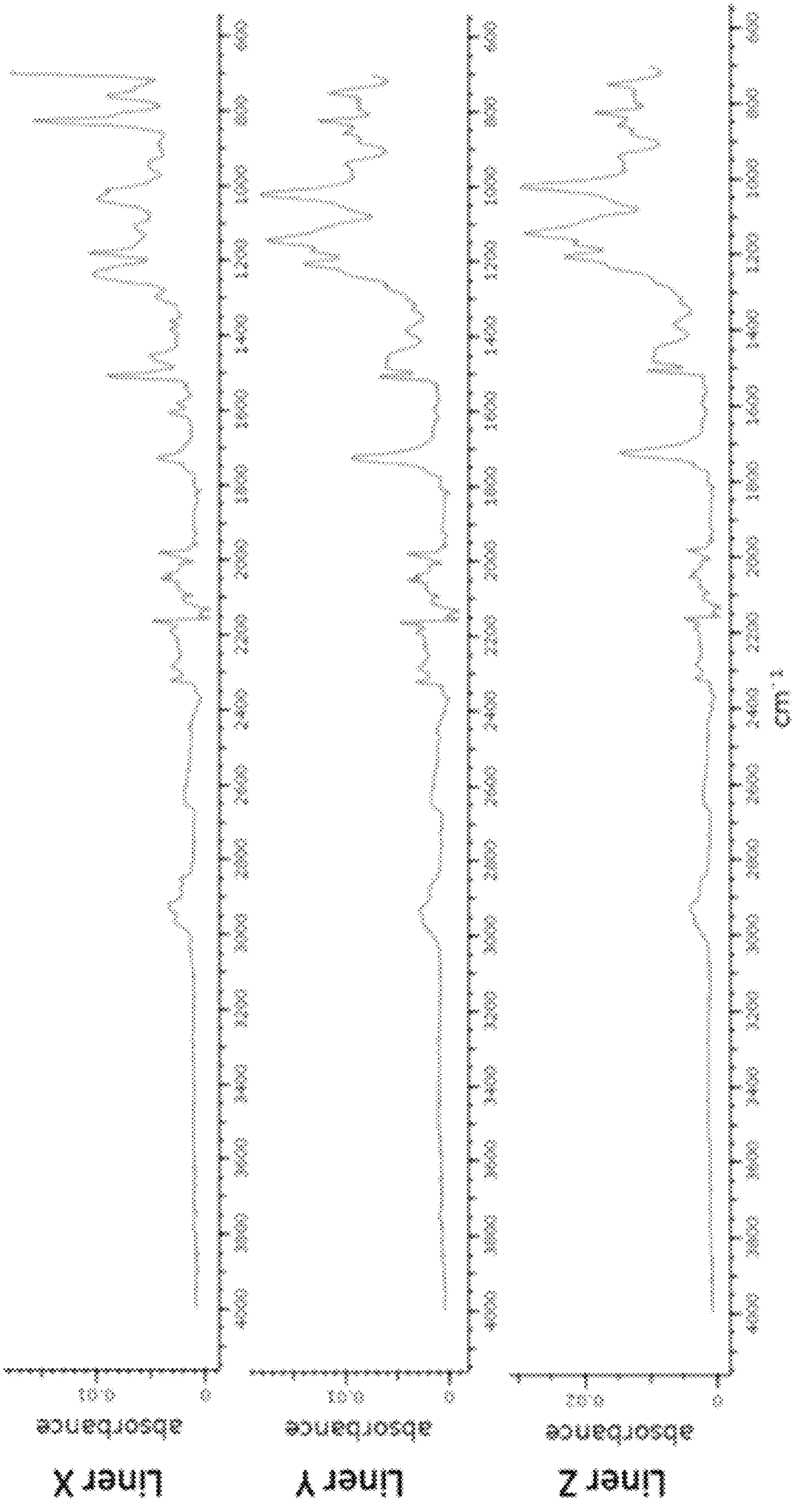
FIG. 20 illustrates an FTIR-ATR spectra of three liners (on aluminum substrate) used in a long-term storage experiment.

In an embodiment, polymeric liner composition may be characterized using Fourier-transform infrared spectroscopy with attenuated total reflectance (FTIR-ATR). Representative spectra for liners extracted from cans $X_1$, $Y_2$, and $Z_2$ are shown in FIG. 20. The BPA epoxy liner ($X_1$) exhibited minor spectral differences from the two BPA-NI epoxy liners ($Y_2$ and $Z_2$), but the latter two appeared identical—consistent with manufacturer documentation identifying both as Valspar V70 (tetramethyl bisphenol F) coatings. Major peaks were observed at approximately 1725, 1510, 1210, 1140, and 1030 $cm^{-1}$, corresponding to characteristic carbonyl stretching, aromatic ring vibration, and C—O—C epoxy linkages. In some embodiments, FTIR-based compositional data may be incorporated into the predictive compatibility model as feature vectors representing resin class, curing agent, and relative cross-link density for correlation with observed stability outcomes.

In some embodiments, liner integrity may be evaluated using electrochemical and optical methods, including enamel-rating (DC current) testing, electrochemical impedance spectroscopy (EIS), acid-copper displacement assays, and adhesion testing. Metal-exposure analysis (enamel rating) applies a direct-current potential (typically 6.3 V) across the can wall, with the measured current proportional to the exposed metal surface area. Industrial quality-control thresholds vary with beverage corrosivity; for example, a 75 mA cutoff is common for beer, whereas a ≤5 mA threshold is recommended for acidic beverages such as wine (Fetters et al., 2004). In the present study, enamel-rating currents for all three long-term test cans were below 4 mA, indicating minimal direct exposure of aluminum. Testing of the visibly defective $Y_2$-2 cans produced only two failures among fifteen samples, likely because an insulating $Al_2O_3$ layer had passivated exposed regions before analysis. These findings suggest that enamel-rating may be less sensitive when evaluating aged or pre-oxidized cans and may be more applicable for in-process manufacturing control than for end-user quality validation.

EIS analysis, employing an alternating-current potential, provides a complementary measure of liner barrier performance by modeling the can-liner system as a resistor-capacitor (RC) circuit. In the current study, impedance was measured at 0.05 Hz, an accepted proxy for corrosion resistance, yielding average values near 10 MΩ, exceeding the minimum recommended threshold for corrosion prevention. No statistically significant differences were detected among the three can sources, which was unexpected given prior literature suggesting that lower impedance correlates with poorer long-term performance. Without being bound by theory, it is possible that the highly reactive components of wine, especially $SO_2$, progressively degrade epoxy-based liners during extended storage, a phenomenon not observable in the short-term EIS tests conducted within one hour of filling. Future embodiments may incorporate time-series EIS measurements into predictive maintenance or liner-degradation models to capture dynamic changes in impedance over storage periods exceeding 14 days. Acidified copper-sulfate testing of unused cans did not reveal visible copper deposition or aluminum-sulfate precipitation, suggesting the absence of macroscopic voids (≥0.05 mm). Likewise, ASTM D3359-17 adhesion testing showed no measurable liner delamination, confirming acceptable adhesion strength for all liners evaluated. However, it is noted that oxide-layer formation between manufacturing and testing may have reduced the sensitivity of both assessments.

Liner-thickness measurements were obtained by laser-scanning profilometry on uniformly coated regions. The $Z_2$ cans exhibited an average liner thickness of 3.27 μm±0.37 μm, significantly greater than $Y_2$ (2.96 μm±0.35 μm), while the $X_1$ cans were intermediate (3.01 μm±0.43 μm). Although this ≈10% increase in mean thickness could contribute to the improved stability of the $Z_2$ cans, profilometry also revealed a higher proportion of thin-coating areas (<0.5 μm) and localized aluminum exposure in $Z_2$ relative to the other groups. Accordingly, overall liner thickness alone is not sufficient to explain reduced $H_2S$ generation; rather, uniformity and coating continuity across the interior surface appear more critical.

In some embodiments, liner-thickness maps, adhesion test results, and impedance data may be digitized and supplied to at least a processor as part of a liner-quality feature set. The processor may apply statistical regression, clustering, or feature-importance ranking to determine which liner characteristics most strongly correlate with observed packaging-stability outcomes. The resulting trained compatibility model may then predict performance of new liner formulations or flag batches exhibiting risk of premature degradation. Accordingly, the structural and electrochemical characterization data described in connection with FIG. 8 demonstrate that both chemical composition and manufacturing uniformity influence liner performance. These empirical results provide foundational input features for the predictive compatibility model disclosed herein, which leverages such multidimensional data to refine liner-selection algorithms, optimize canning parameters, and minimize the likelihood of post-packaging chemical instability events.

With continued reference to FIG. 8, in some embodiments, cans sourced from manufacturer Z and manufacturer V exhibited distinct performance advantages under accelerated aging conditions. Specifically, manufacturer Z's BPA epoxy and manufacturer V's BPA-NI epoxy slim-format cans produced minimal hydrogen sulfide ($H_2S$) accumulation in the accelerated-aging protocol (corresponding to FIG. 7) and were characterized by significantly greater average liner thicknesses (as shown in FIG. 8) relative to the remaining liner types analyzed (Student's t-tests, $p<0.05$). Notably, these cans maintained lower $H_2S$ formation despite a comparatively larger internal surface area, suggesting that liner thickness and uniformity may outweigh surface-area-driven effects in governing gas evolution and corrosion resistance. In some embodiments, these findings indicate that at least a processor may assign elevated compatibility weights or quality-confidence parameters to liner formulations exhibiting increased mean coating thickness coupled with minimal $H_2S$ generation, even where the geometric exposure area would predict higher reactivity. This relationship reinforces that liner microstructure and polymer continuity are dominant factors within the predictive compatibility model's stability-scoring framework, rather than overall can geometry alone.

Figure 9:
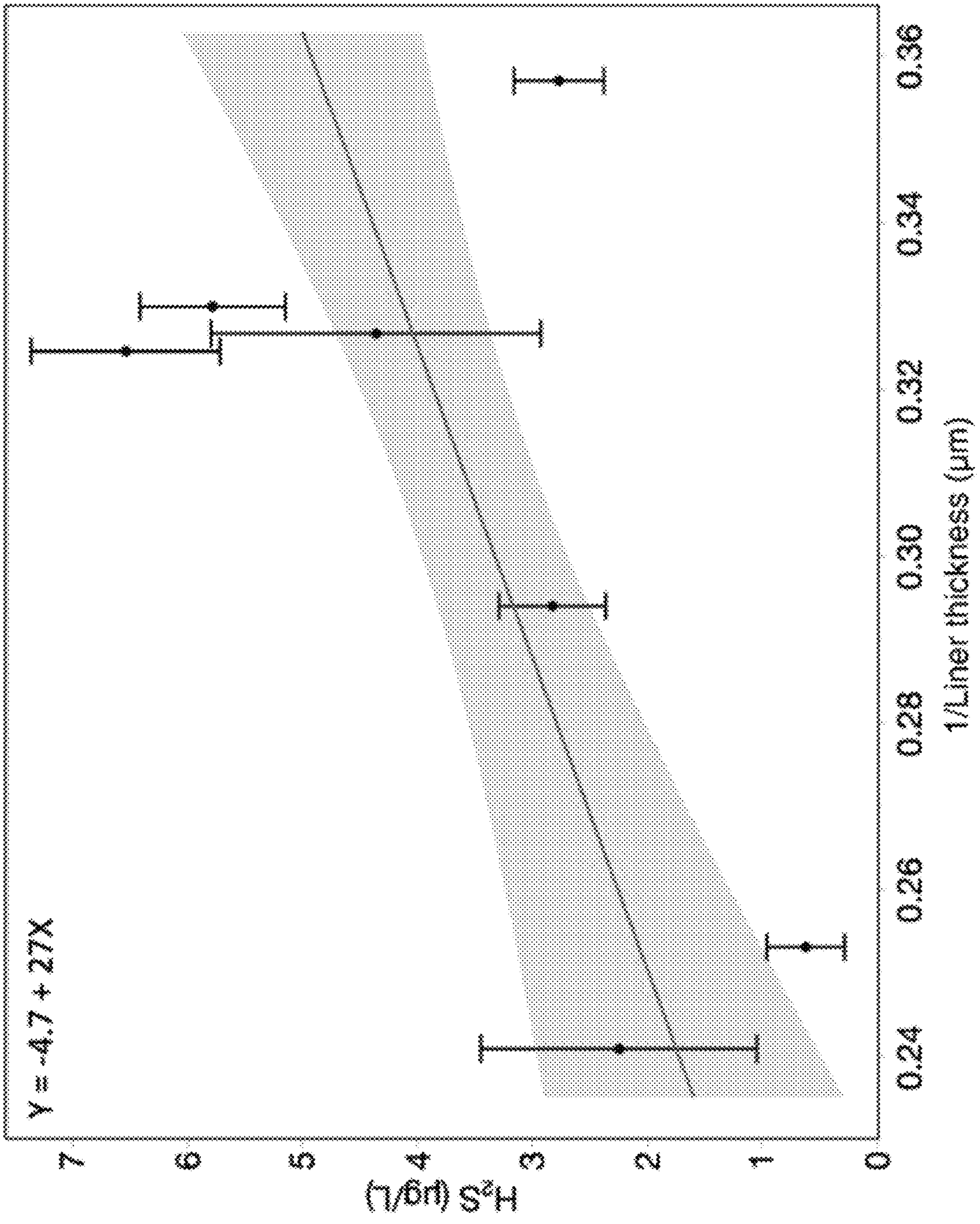
FIG. 9 is a graphical representation of hydrogen sulfide ($H_2S$) formation after three days at 50° C. versus inverse liner thickness for epoxy lined cans.

With reference now to FIG. 9, a graphical representation of hydrogen sulfide ($H_2S$) formation after three days at 50° C. versus inverse liner thickness for epoxy lined cans (BPA and BPA-NI) is illustrated. Each point represents the average $H_2S$ for a different liner (n=8 technical replicates per liner). Error bars represent one standard error. In some embodiments, at least a processor may perform a regression analysis of the inverse liner-thickness values against the measured hydrogen sulfide ($H_2S$) concentrations generated under accelerated-aging conditions. Acrylic liners and the visibly defective Y2-2 cans were excluded from this regression due to their known coating irregularities. For purposes of this disclosure, the "inverse liner thickness" refers to the reciprocal of the measured coating thickness and serves as a proportional estimator for coating permeability and, therefore, the expected rate of sulfur dioxide ($SO_2$) diffusion through the liner. A statistically significant correlation was observed between the inverse of liner thickness and the amount of $H_2S$ produced, indicating that thinner or more permeable coatings permit enhanced $SO_2$ transport and subsequent reductive sulfur formation.

In some embodiments, the system may further identify that liner-thickness uniformity, represented by the standard deviation of the thickness measurements, plays a critical role in determining overall compatibility. The two liner groups that produced the least $H_2S$, namely Y2-3 and Z1 (see FIG. 7), also exhibited the lowest standard deviations in liner thickness (see FIG. 8), suggesting that consistency of coating application, rather than absolute mean thickness alone, governs diffusion stability. Without being bound by theory, it is postulated that micro-thin or under-cured regions may act as preferential diffusion channels, accelerating localized $SO_2$ permeation and thus $H_2S$ generation. Interestingly, the cans with the thinnest average liner, designated Y2-3, produced intermediate amounts of $H_2S$, despite their reduced thickness. These cans were identified as "soda-weight" or "beer-weight" designs intended for lower-acidity products and thus received a thinner coating and lower cure temperature than "hard-to-hold" beverage cans (e.g., those used for wine, sour beer, or kombucha). All other cans in the study were designed for these more reactive beverage classes and therefore featured thicker liners and more stringent quality-control validation (e.g., enamel-rater and cure-integrity testing). This distinction supports the inference that manufacturing classification and thermal cure parameters may be integrated as categorical variables in the predictive compatibility model to account for performance variation across intended product categories.

Although the acrylic liner group (Y3) displayed the highest average liner thickness among all evaluated samples (see FIG. 8), it nonetheless exhibited substantial $H_2S$ accumulation. This observation is consistent with prior findings demonstrating that $SO_2$ and other wine constituents can chemically degrade acrylic resins, compromising liner integrity and exposing the underlying aluminum substrate. Accordingly, the system may assign a lower compatibility weighting to acrylic-based formulations, regardless of nominal coating thickness, due to their known chemical instability under acidic, $SO_2$-rich conditions. In further embodiments, liner-thickness data may also be acquired by optical interferometry to validate profilometric results across broader surface regions. Interferometric analysis yields averaged thickness values across 1-2 $mm^2$ sampling windows, providing macro-level thickness mapping but without micron-scale precision. For the three can sources evaluated in long-term storage studies. The order of average and minimum thickness (Z>X>Y) measured by interferometry matched that observed using laser-scanning profilometry, confirming consistency across measurement techniques. In some embodiments, such redundant measurement data may be supplied to at least a processor for cross-validation, outlier detection, or error-propagation modeling within the liner-quality assessment module of the system. Accordingly, the empirical correlation between inverse liner thickness and $H_2S$ formation depicted in FIG. 9 demonstrates that the permeability and uniformity of the polymeric barrier are primary determinants of chemical stability. These findings substantiate the predictive compatibility model's underlying logic, wherein liner-thickness metrics and their statistical dispersion are incorporated as input features for estimating diffusion-limited reaction probabilities, guiding both liner selection and recommended coating specifications for future canning operations.

Figure 10:
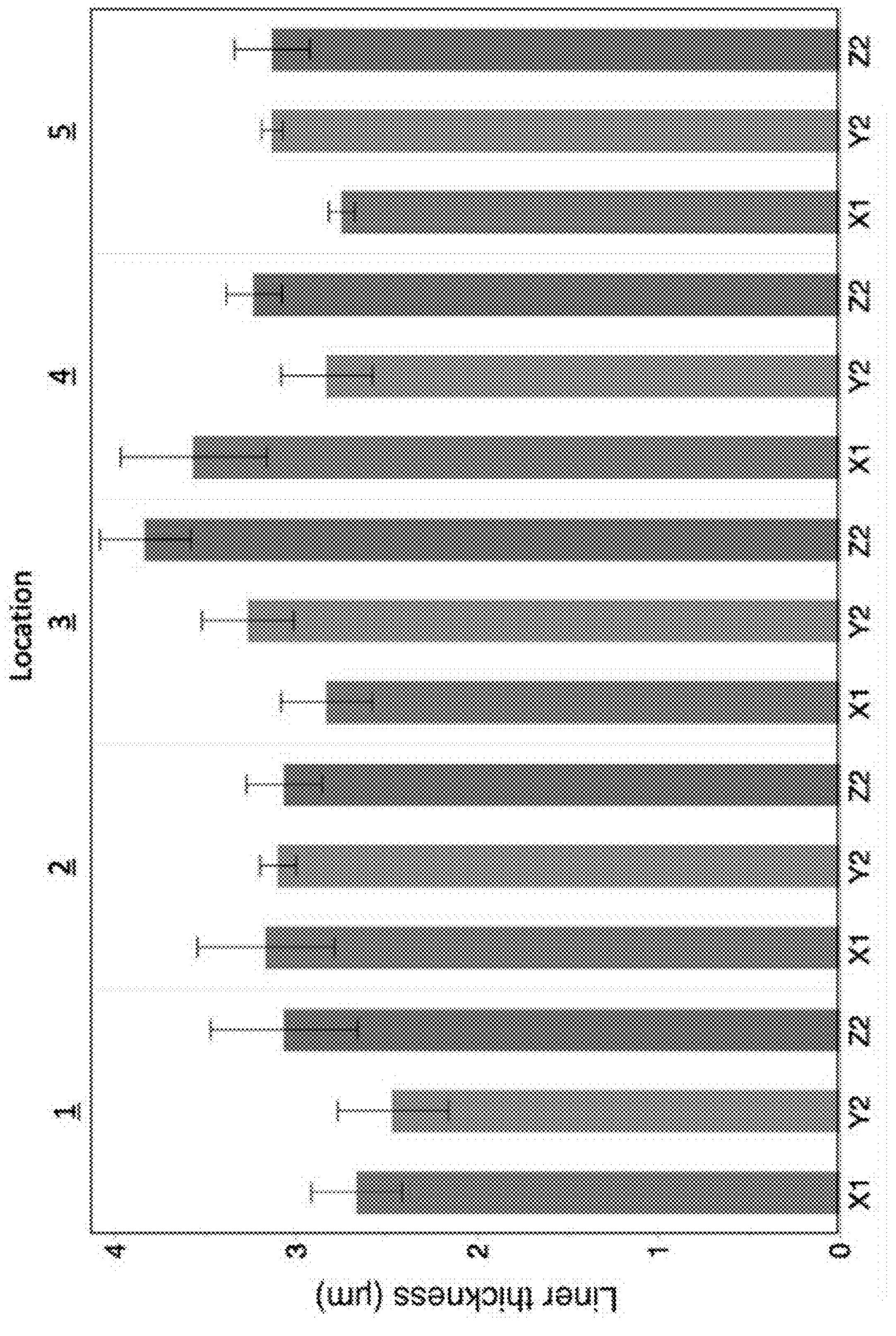
FIG. 10 is a graphical representation of liner thickness measurements by laser-scanning profilometry, measured across the cans (X1, Y2, and Z2)

With continued reference to FIG. 10, a graphical representation of liner thickness measurements by laser-scanning profilometry, measured across the cans (X1, Y2, and Z2). Three technical replicates were analyzed. Error bars represent one standard deviation. X1, Y2, Z2: X, Y, and Z signify the can manufacturer; 1 and 2 signify the liner type (BPA epoxy and BPA-NI epoxy, respectively). For example, Y2 indicates a BPA-NI epoxy can from manufacturer Y. In some embodiments, liner-thickness measurements were also obtained for the underside of can ends, which are regions that rarely exhibit visible corrosion during long-term storage. Measurements were taken on flat portions of the can end to ensure optical uniformity, and the average liner thickness was determined to exceed approximately 8 μm, roughly threefold greater than the corresponding thicknesses observed in the can body. Without being bound by theory, this increased thickness is believed to contribute to the enhanced corrosion resistance commonly observed in these regions, as the augmented polymer barrier limits both oxygen ingress and sulfur dioxide ($SO_2$) permeation into the underlying aluminum substrate. In some embodiments, liner-thickness mapping was performed across multiple internal locations within the can body and headspace for the three can sources evaluated in long-term aging trials. Measurements were conducted by laser-scanning profilometry, as schematically represented in FIG. 2 and graphically summarized in FIG. 10, encompassing five distinct sampling sites along the can interior. The thinnest liner coverage (~2.5 μm) was consistently observed in the upper headspace region (Location 1) of the Y2 cans, correlating with elevated hydrogen sulfide ($H_2S$) formation previously measured in that same region.

In some embodiments, this spatial correlation between liner thickness and $H_2S$ generation supports the inference that regions exhibiting thinner or non-uniform coatings demonstrate shorter onset times for measurable gas accumulation, assuming equivalent beverage composition and environmental conditions. Accordingly, the system may be configured such that at least a processor integrates localized liner-thickness data into the predictive compatibility model as a spatial weighting factor, enabling simulation of corrosion initiation thresholds and time-to-failure predictions across distinct can zones. Such spatially resolved modeling may further inform targeted coating-process optimization or liner-reinforcement recommendations for high-risk areas, particularly in the upper headspace region where coating stress and thermal variability during curing are greatest.

In some embodiments, experimental validation confirmed that the molecular sulfur dioxide ($SO_2$) fraction of total sulfites represents the most reliable predictor of hydrogen sulfide ($H_2S$) formation during long-term storage of canned wine compositions across a range of beverage formulations and liner chemistries. Significant variability in both $H_2S$ accumulation and visible corrosion was observed not only among cans incorporating different polymeric liner materials, but also among cans utilizing nominally identical liner chemistries sourced from different manufacturers. Furthermore, can-to-can variation within a single manufacturer's production batch was found to be non-negligible, indicating that micro-scale differences in coating application, curing, or substrate treatment may materially influence stability performance.

In some embodiments, physical, optical, and mechanical integrity assessments of unused cans, such as enamel rating, adhesion, and impedance spectroscopy, did not consistently predict long-term corrosion or gas-evolution behavior. However, statistical correlation analysis demonstrated that performance variation among can groups was modestly associated with differences in liner thickness and uniformity, supporting the inference that coating geometry plays a partial, but not exclusive, role in mediating chemical stability. Without being bound by theory, it is postulated that liner degradation through chemical reaction with dissolved sulfites, rather than purely mechanical failure, represents a primary initiation pathway for corrosion and $H_2S$ formation.

These findings collectively suggest that the combination of initial liner thickness and intrinsic chemical resistance of the coating material to sulfur-containing species governs overall packaging stability. In some embodiments, the system disclosed herein may incorporate these empirical relationships into a predictive compatibility model that weights liner chemical composition and geometric parameters to forecast long-term stability outcomes. Such correlations may further extend beyond wine to other acidified or sulfur-containing products, including functional beverages, kombucha, and fruit-based formulations, where analogous beverage-liner interactions are expected. Accordingly, it is recommended that packaging validation workflows include controlled storage or coupon testing prior to large-scale use of a liner formulation, thereby verifying integrity under representative chemical conditions.

With reference now to FIG. 11, a table illustrating initial composition of wines used in the long-term canning study is shown. In some embodiments, the initial composition of the beverage formulations used in the long-term canning study is provided as exemplary input data for the system's predictive compatibility model. For purposes of this disclosure, FIG. 10 illustrates representative analytical parameters obtained from five commercial wine samples, including but not limited to pH, titratable acidity (TA), alcohol by volume (ABV), free sulfur dioxide ($SO_2$), molecular $SO_2$, and dissolved oxygen ($dO_2$). Each parameter corresponds to a defined "chemical parameter" of the beverage composition profile as previously described.

In an embodiment, the dataset represented in FIG. 11 may be used to populate the initial beverage composition profiles received by at least a processor prior to defining composition adjustment thresholds. These parameter values may serve as baseline conditions from which permissible deviations are determined and from which liner-compatibility simulations are initiated. The table further illustrates variability among different beverage types, such as Pinot Grigio, Sauvignon Blanc, French Rosé, sparkling Rosé, and sparkling White, demonstrating the system's applicability across diverse formulations. Accordingly, FIG. 11 provides an illustrative example of the chemical input space upon which the predictive compatibility model operates. It is understood that the particular values shown are non-limiting and may vary according to beverage category, analytical method, and intended packaging configuration. In some embodiments, the system may dynamically normalize or standardize these values prior to model inference to ensure consistency across datasets collected from different analytical sources or production environments.

With reference now to FIG. 12A, a table of parameters for open circuit potential testing is shown. In some embodiments, parameters for open circuit potential (OCP) testing are presented to illustrate the electrochemical validation conditions used to assess liner integrity and aluminum corrosion susceptibility. For purposes of this disclosure, the OCP test measures the equilibrium potential between the can substrate and a reference electrode in the absence of externally applied current, providing a non-destructive indication of the coating's barrier performance. In an embodiment, FIG. 12A presents representative experimental parameters including electrolyte composition, electrode configuration, stabilization criteria, potential drift thresholds, and measurement duration. Each parameter defines an operational boundary condition that the system may replicate when simulating corrosion-onset scenarios or calibrating predictive liner degradation models. For example, in a hardware-integrated embodiment, at least a processor may access stored OCP parameter sets to control an automated testing apparatus and record voltage drift data for use in liner performance scoring.

It will be understood that the parameters listed in FIG. 12A are exemplary and non-limiting. Variations in electrolyte concentration, reference electrode type, or stabilization criteria may be implemented without departing from the scope of the disclosed embodiments. The dataset represented in FIG. 11 thus serves as an example of how electrochemical measurement conditions can be formalized for system calibration, model training, or quality-assurance workflows.

With reference now to FIG. 12B, a table of parameters for electrochemical impedance spectroscopy testing is shown. In some embodiments, parameters for electrochemical impedance spectroscopy (EIS) testing are provided to illustrate representative electrochemical conditions for evaluating the barrier performance and degradation behavior of polymeric liners. For purposes of this disclosure, EIS testing involves the application of an alternating current (AC) signal across the liner-electrolyte interface while measuring impedance as a function of frequency, thereby characterizing both resistive and capacitive components of liner integrity. In an embodiment, FIG. 12B depicts exemplary testing parameters including frequency range, AC amplitude, applied DC bias, open-circuit potential (OCP) stabilization period, electrolyte composition, and data-acquisition intervals. Each of these parameters establishes the baseline conditions under which impedance spectra are collected and subsequently analyzed using equivalent-circuit models to infer coating porosity, adhesion, and corrosion susceptibility. In some embodiments, at least a processor may be configured to access the parameter schema of FIG. 12B to standardize laboratory or in-situ EIS testing routines, ensuring repeatable data capture across production facilities.

It will be appreciated that the specific parameters shown in FIG. 12B are exemplary and may be varied according to the electrolyte system, liner chemistry, or measurement instrumentation without departing from the scope of the disclosed embodiments. In an embodiment, EIS parameters such as those shown in FIG. 12B may be stored as metadata linked to individual liner performance records, enabling correlation between electrochemical response and predicted long-term packaging stability.

Figure 13:
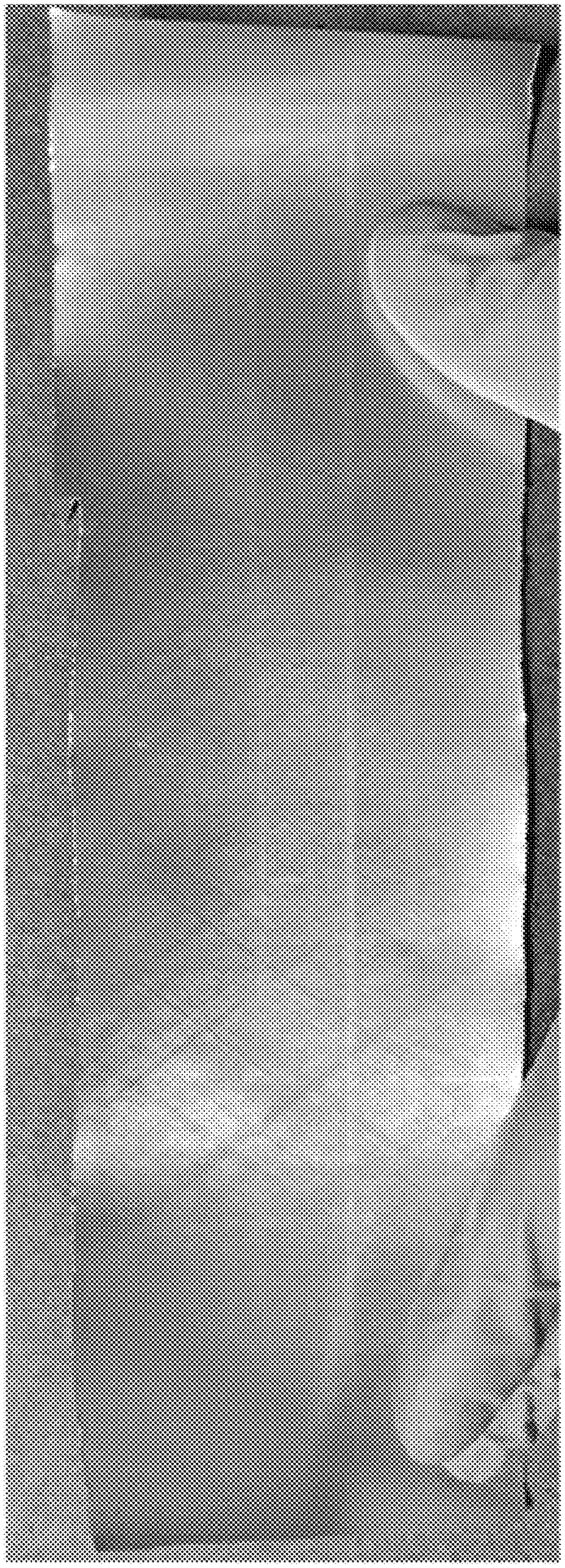
FIG. 13 is an illustration of a can body with the top and bottom removed.

With reference now to FIG. 13, an illustration of a can body with the top and bottom removed is shown. In some embodiments, a schematic representation of a prepared aluminum can body is shown, with the top and bottom sections removed to facilitate liner evaluation and coupon preparation. For purposes of this disclosure, removal of the top and bottom portions of the can allows access to the internal surface of the cylindrical body for subsequent sectioning, cleaning, and analytical characterization. In an embodiment, the can body depicted in FIG. 13 may correspond to the configuration used for preparing aluminum coupons for accelerated aging trials or for optical and electrochemical liner assessments. In some embodiments, at least a processor may receive digital or imaging data corresponding to a can body configuration such as that shown in FIG. 13 to index the sampling regions and associate analytical measurements (e.g., liner thickness, corrosion scoring, impedance spectra) with specific spatial coordinates. This enables traceable correlation between experimental data and geometric position within the container, which may later inform feature mapping or model refinement in the predictive compatibility framework.

Figure 14:
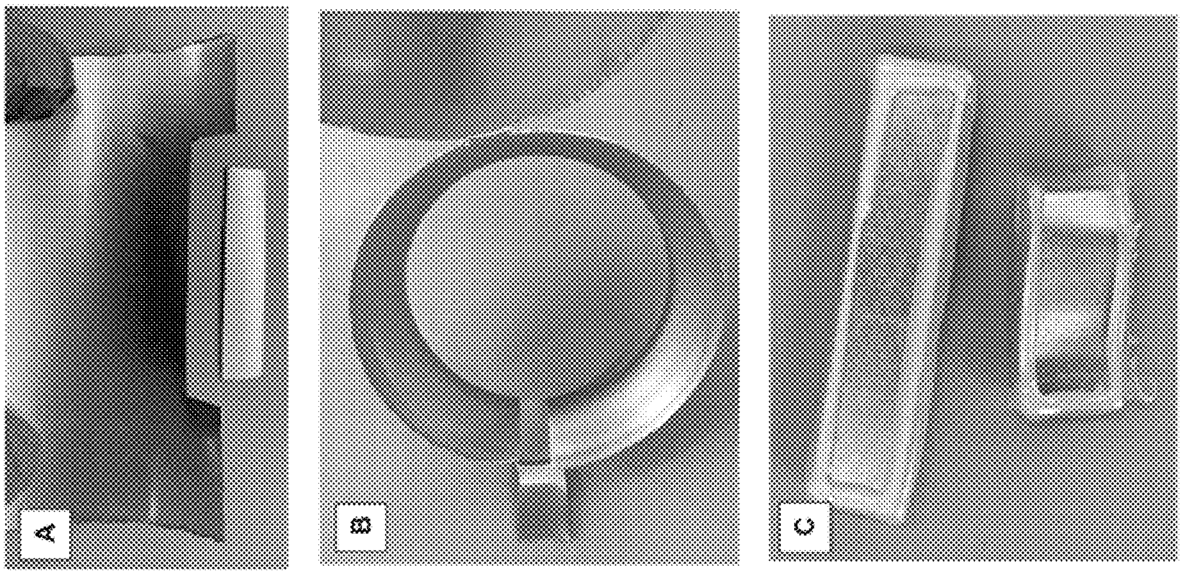
FIG. 14 illustrates exemplary locations and configurations of aluminum coupons used for accelerated aging texting, including (A) body-region coupons, (B) headspace-region coupons, and (C) sealed-edge coupons prepared with hot-melt adhesive to prevent bare aluminum exposure during testing.

With reference now to FIG. 14, illustrated is exemplary locations and configurations of aluminum coupons used for accelerated aging texting, including (A) body-region coupons, (B) headspace-region coupons, and (C) sealed-edge coupons prepared with hot-melt adhesive to prevent bare aluminum exposure during testing. in some embodiments, representative sampling locations and coupon configurations used for accelerated aging testing are shown. (A) body illustrates exemplary coupon sections obtained from the body region of an aluminum can, while (B) headspace illustrates coupons sectioned from the headspace region of the can. Each coupon represents a defined area of liner-coated substrate selected for evaluation under controlled chemical and thermal conditions. For purposes of this disclosure, such coupons are used to replicate the localized liner-beverage interactions occurring in distinct geometric regions of the full container.

As shown at location C, the exposed aluminum along the cut edges of each coupon may be sealed using a hot-melt adhesive material (e.g., ethylene-vinyl acetate), thereby isolating the coated surface and preventing direct exposure of bare aluminum during immersion testing. In an embodiment, sealing the edges with a non-reactive polymer ensures that observed chemical or electrochemical responses arise exclusively from liner-beverage interactions rather than edge corrosion or galvanic interference. In some embodiments, at least a processor may receive image data, coordinate mappings, or metadata corresponding to coupon geometry and sampling location, such as those depicted in FIG. 14, to contextualize analytical results (e.g., $H_2S$ formation, impedance spectra, or color shift metrics) by physical region. This allows the predictive compatibility model to associate liner performance with spatial variables, such as curvature, headspace proximity, or localized coating thickness, enhancing spatially resolved corrosion prediction accuracy.

Figure 15:
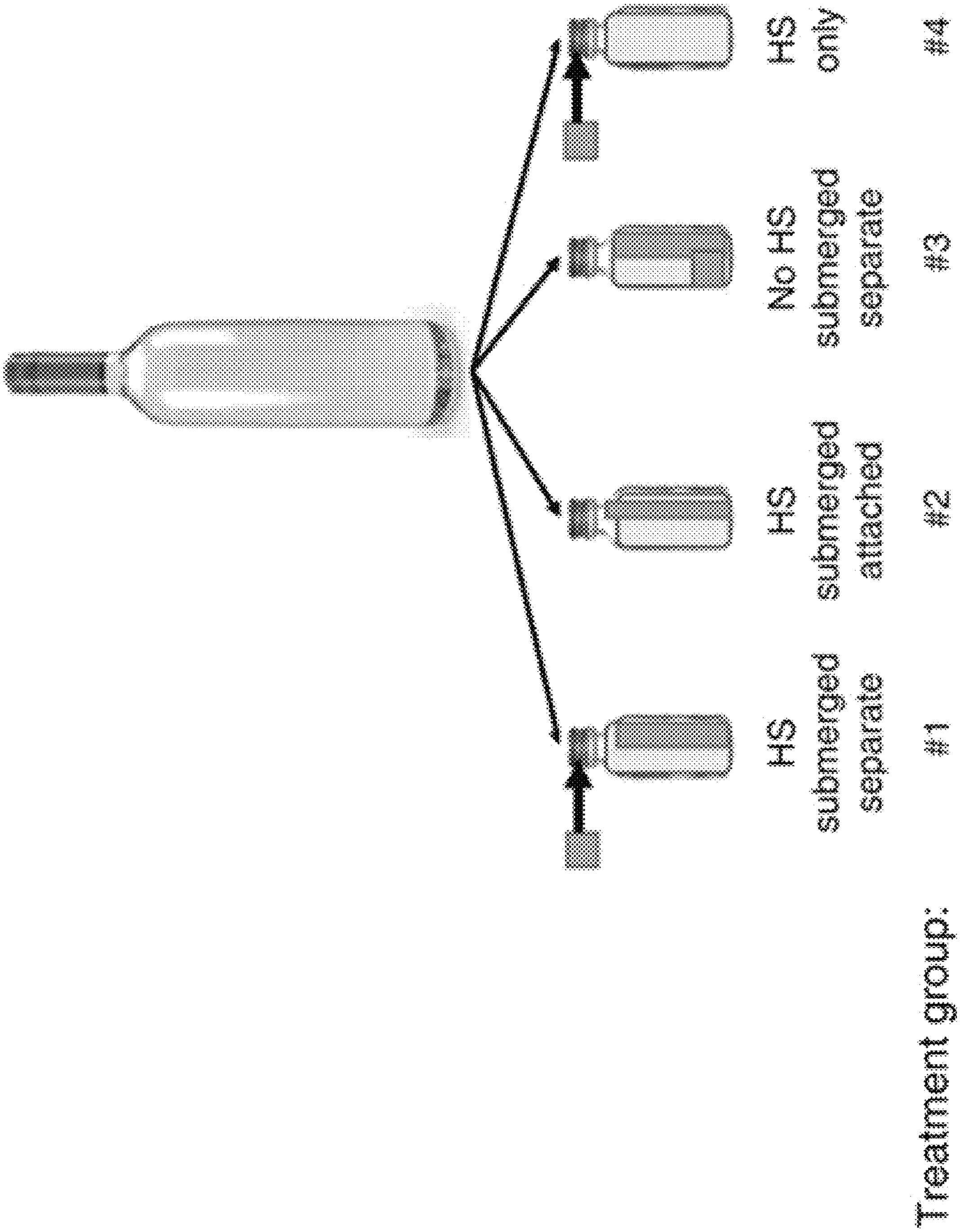
FIG. 15 illustrates an exemplary experimental design for comparing immersed and non-immersed aluminum surfaces during accelerated aging, showing coupon orientations corresponding to headspace (HS) and submerged exposure regions.

With reference now to FIG. 15, illustrated is an exemplary experimental design for comparing immersed and non-immersed aluminum surfaces during accelerated aging, showing coupon orientations corresponding to headspace (HS) and submerged exposure regions. Four technical replicates were performed for each treatment configuration. FIG. 15 illustrates an experimental configuration for evaluating the relative effects of immersed and non-immersed aluminum surfaces on hydrogen sulfide ($H_2S$) formation during accelerated aging. For purposes of this disclosure, the arrangement shown in FIG. 15 demonstrates the orientation of coated aluminum coupons within sealed vials, allowing comparative analysis of headspace-exposed (HS) and liquid-immersed regions under identical thermal and chemical conditions.

In an embodiment, FIG. 15 depicts four representative coupon orientations, each corresponding to a unique combination of immersion depth and exposure environment. These configurations include fully submerged coupons, partially submerged coupons with defined vapor exposure area, and headspace-mounted coupons affixed to vial septa. Each configuration was tested in quadruplicate (four technical replicates per treatment), enabling statistical evaluation of $H_2S$ generation as a function of surface exposure. In some embodiments, at least a processor may associate experimental configuration metadata, such as coupon orientation, immersion depth, and exposure time, with observed $H_2S$ concentrations to parameterize a corrosion-reaction model within the predictive compatibility framework. This allows the system to distinguish between liquid-phase and vapor-phase reaction dynamics and to quantify how liner exposure geometry affects gas-phase sulfur accumulation.

Figure 16:
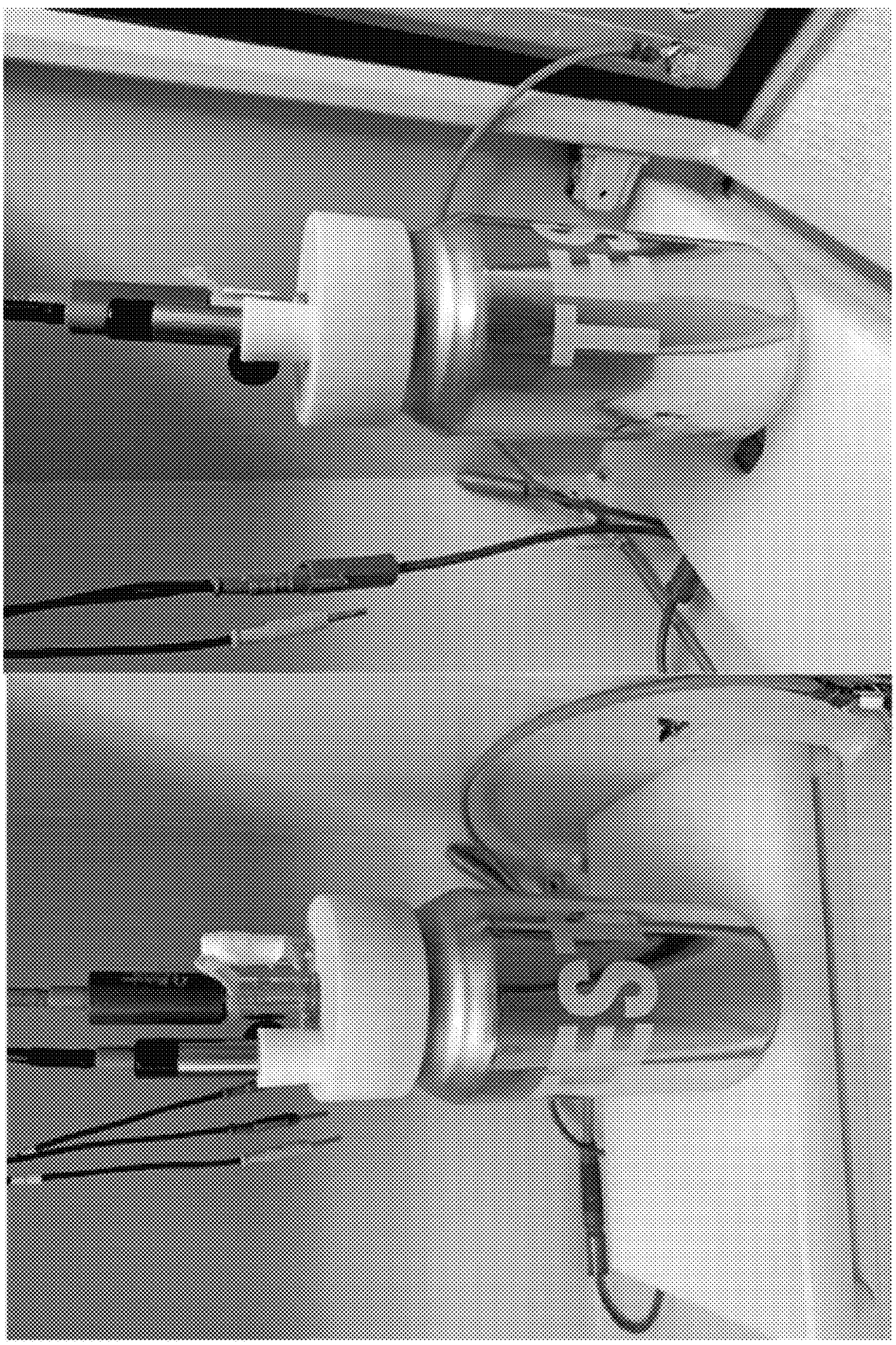
FIG. 16 illustrates an exemplary electrochemical impedance spectroscopy setup, showing the counter electrode (left), reference electrode (center), and working electrode (bottom of can)

With reference now to FIG. 16, illustrated is an exemplary electrochemical impedance spectroscopy setup, showing the counter electrode (left), reference electrode (center), and working electrode (bottom of can). The electrochemical cell is positioned inside a grounded Faraday cage to eliminate electromagnetic interference during measurement. In some embodiments, an electrochemical impedance spectroscopy (EIS) testing arrangement is illustrated for characterizing the electrical and barrier properties of can liners. As depicted, the system includes a counter electrode positioned on the left, a reference electrode centrally located, and a working electrode in electrical contact with the bottom of the can under evaluation. The can is filled with an electrolyte solution and functions as the electrochemical cell during testing. In an embodiment, the electrochemical cell is housed within a grounded Faraday cage, as shown in FIG. 16, to minimize external electromagnetic interference during measurement. This configuration ensures signal integrity and reproducibility when determining open-circuit potential and frequency-dependent impedance characteristics.

In some embodiments, the EIS system may be configured to generate frequency sweeps over a defined range (e.g., 105 Hz to 10-2 Hz) while applying alternating-current (AC) excitation. The resulting data can be modeled as an equivalent circuit (e.g., resistor-capacitor pair) to estimate coating resistance, charge-transfer resistance, and double-layer capacitance associated with the polymeric liner. The collected measurements may be processed by at least a processor to determine liner integrity, degree of porosity, or onset of electrochemical degradation.

Figure 17:
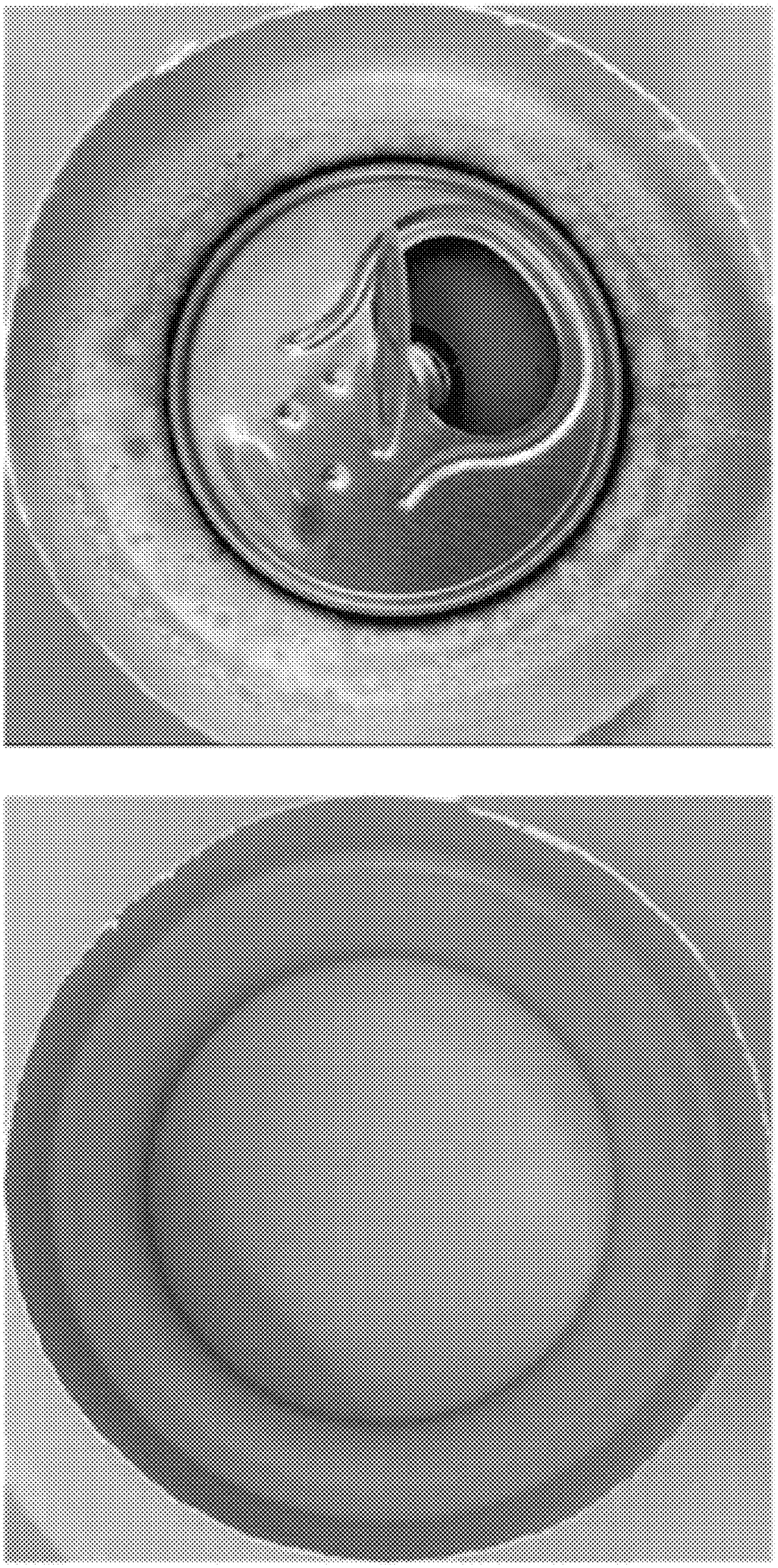
FIG. 17 illustrates a visual comparison between an unused can with no corrosion (left) and a used can exhibiting corrosion localized to the neck region (right)

With reference now to FIG. 17, illustrated is a visual comparison between an unused can with no corrosion (left) and a used can exhibiting corrosion localized to the neck region (right). In some embodiments, comparative visual evidence of corrosion patterns in aluminum beverage cans following long-term storage is shown. FIG. 17 (left) illustrates an unused can interior exhibiting an intact, uniformly coated liner surface with no visible corrosion. FIG. 17 (right) depicts a corresponding can after product storage, showing localized corrosion primarily concentrated in the upper neck region of the container. In an embodiment, the observed corrosion is indicative of liner degradation or reduced coating performance in high-curvature regions, which may experience greater mechanical stress or thinner applied coatings during manufacturing. The neck region often presents a more challenging geometry for achieving uniform liner coverage, making it a potential site for accelerated degradation when exposed to acidic or sulfur-containing beverages.

In some embodiments, the corrosion mapping represented in FIG. 17 can be used to train a predictive liner-failure model, wherein image-based corrosion signatures are correlated with process metadata (e.g., liner thickness, cure temperature, can geometry). The system may thereby automatically identify regions of elevated corrosion susceptibility and adjust liner deposition or quality control parameters accordingly.

Figure 18:
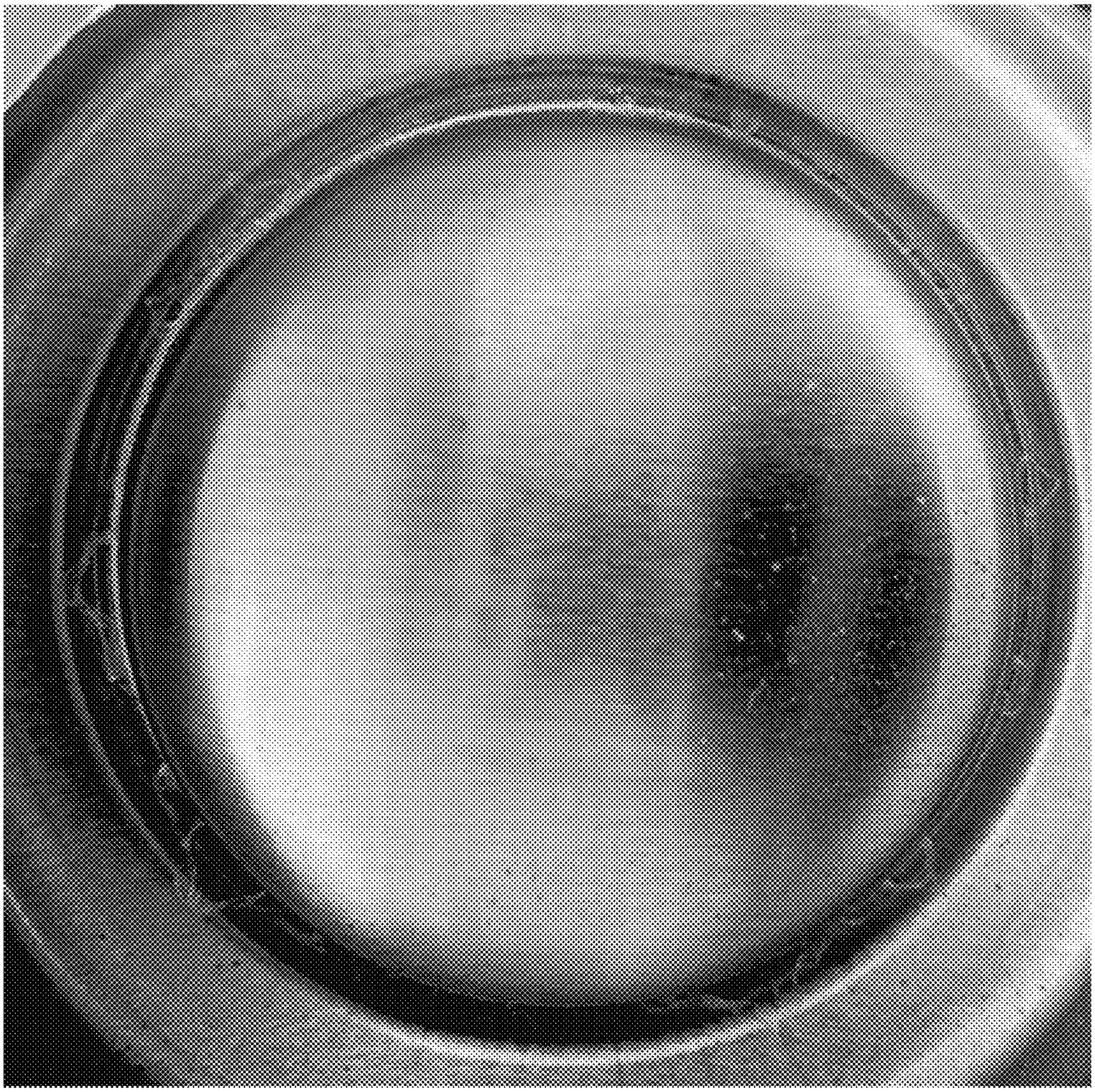
FIG. 18 illustrates visual defects in the polymeric lining of the moat region of Y2-2 cans prior to storage.

With reference now to FIG. 18, illustrated is visual defects in the polymeric lining of the moat region of Y2-2 cans prior to storage. The Y2-2 code designates the second batch of BPA-NI epoxy-lined cans from manufacturer Y, tested to evaluate batch-to-batch variation. In some embodiments, representative visual defects are illustrated in the polymeric liner of the "moat" region of certain aluminum beverage cans. The depicted example corresponds to the Y2-2 batch, wherein "Y" denotes the manufacturer and "2" denotes the liner type (BPA-NI epoxy). Multiple production batches from the same manufacturer were evaluated (e.g., Y2, Y2-2, Y2-3) to assess batch-to-batch variability in liner uniformity and integrity.

In some embodiments, as depicted in FIG. 18, the polymeric liner exhibits incomplete coverage and localized thinning along the recessed curvature of the moat region. These areas represent critical weak points where liquid ingress or liner delamination may initiate during product storage, leading to elevated hydrogen sulfide formation or visible corrosion. In an embodiment, batch-to-batch variation in liner application parameters, such as spray angle, viscosity, and cure temperature, may account for the irregularities observed in FIG. 18. Consistent with experimental findings, this batch (Y2-2) produced approximately ten-fold higher $H_2S$ concentrations than other batches of the same liner chemistry, confirming that mechanical or geometric nonuniformities in liner deposition can significantly influence long-term can performance.

With reference now to FIG. 19, illustrated is an elemental analysis by x-ray fluorescence (XRF) for Y2 and Z2 cans.

Each sample represents a BPA-NI epoxy-lined can, with three technical replicates analyzed per manufacturer. Y2 and Z2 indicate cans from manufacturers Y and Z, respectively. In some embodiments, comparative results of elemental analysis conducted by x-ray fluorescence (XRF) spectroscopy for cans Y2 and Z2 are shown. Each sample corresponds to a BPA-NI epoxy-lined can, wherein the letter (Y or Z) denotes the manufacturer and the number "2" denotes the liner type. Three technical replicates were analyzed per manufacturer.

As depicted in FIG. 19, both Y2 and Z2 cans exhibited comparable base compositions consistent with Al 3004 alloy specifications, including characteristic peaks for aluminum, manganese, magnesium, and trace transition metals. However, detectable variation in minor alloying elements such as chromium (Cr) and copper (Cu) was observed between the two sources. In particular, manufacturer Z exhibited approximately three-fold higher Cr intensity relative to manufacturer Y, while all other element peak intensities varied by less than 20%. In some embodiments, the relative abundance of alloying elements revealed by XRF spectroscopy may serve as an indicator of metallurgical consistency or manufacturing variability. Although such differences were not found to correlate strongly with hydrogen sulfide ($H_2S$) formation under accelerated or long-term storage conditions, the analysis demonstrates that subtle deviations in alloy composition can be systematically quantified as part of a broader diagnostic workflow for predicting can performance.

With reference now to FIG. 20, illustrated is an FTIR-ATR spectra of three liners (on aluminum substrate) used in the long-term storage experiment. X1, Y2, and Z2 denote can manufacturers X, Y, and Z, respectively; liner types 1 and 2 correspond to BPA epoxy and BPA-NI epoxy formulations. In some embodiments, Fourier transform infrared-attenuated total reflectance (FTIR-ATR) spectra obtained from the polymeric liners of three representative can types (X1, Y2, and Z2) are shown. Each liner was applied on an aluminum substrate and corresponds to a liner formulation used in the long-term storage study. Specifically, the X1 can includes a BPA epoxy liner, while Y2 and Z2 cans include BPA-NI epoxy liners. The letters X, Y, and Z signify the respective can manufacturers, and the numerals "1" and "2" designate the liner types.

As depicted in FIG. 20, the FTIR-ATR spectra exhibit strong absorbance bands near 1725 $cm^{-1}$, 1510 $cm^{-1}$, 1210 $cm^{-1}$, 1140 $cm^{-1}$, and 1030 $cm^{-1}$, corresponding to C═O stretching, aromatic C═C vibrations, and ether or hydroxyl-related stretching modes characteristic of epoxy-based coatings. Only minor spectral differences were observed between the BPA epoxy (X1) and BPA-NI epoxy (Y2, Z2) liners, consistent with their similar resin backbones. In an embodiment, the overlapping absorbance profiles of Y2 and Z2 liners indicate that both coatings are likely derived from similar formulations (e.g., tetramethyl bisphenol F epoxy resins such as Valspar V70). However, slight differences in relative peak intensity and baseline shape may reflect variations in cure temperature, film crosslinking, or pigment loading introduced during manufacturer-specific coating processes. Such differences could contribute to the distinct hydrogen sulfide ($H_2S$) generation trends observed in the long-term storage study.

Figure 21:
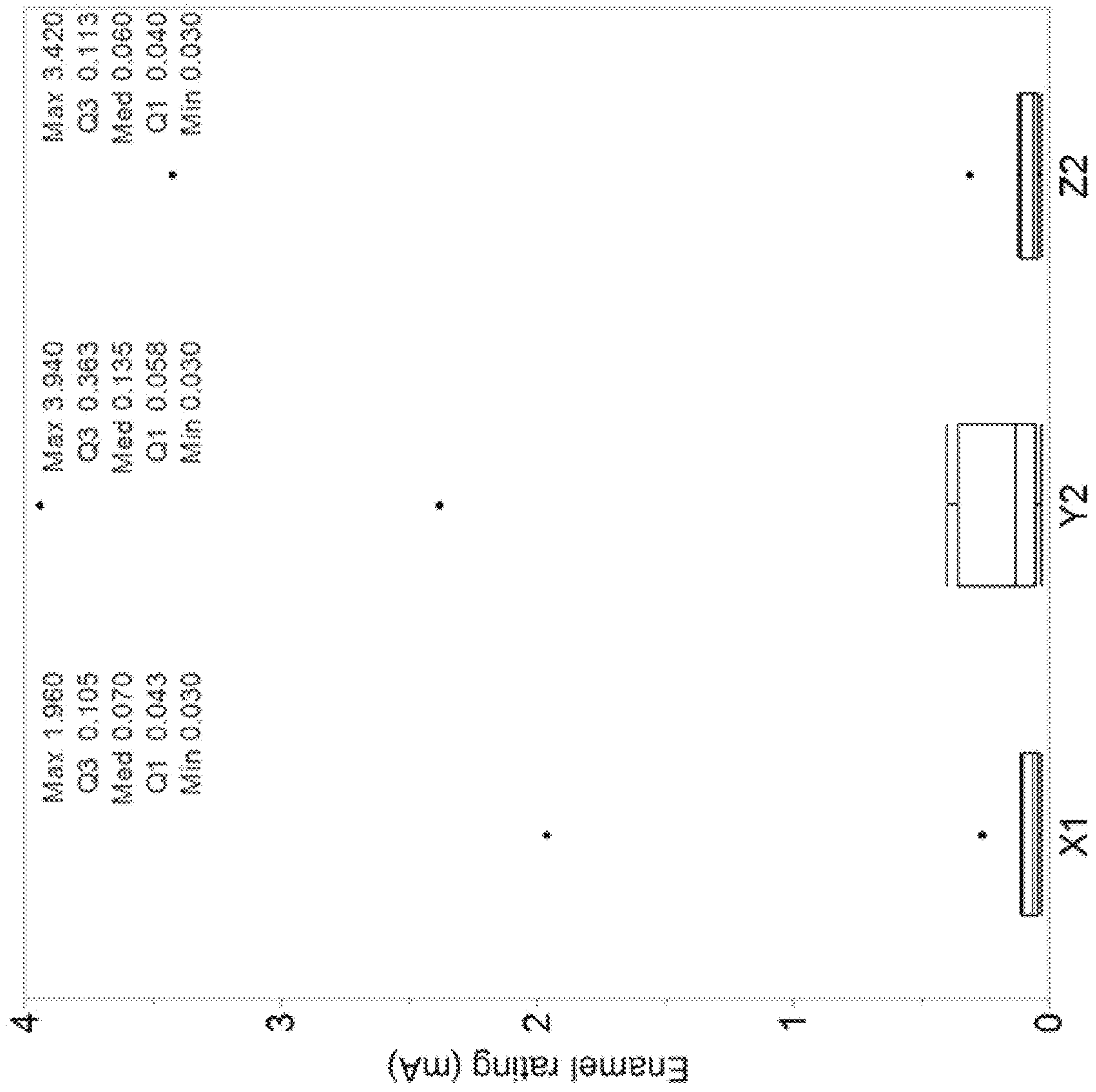
FIG. 21 illustrates metal exposure (enamel) ratings for three can types, X1 (BPA epoxy), Y2 (BPA-NI epoxy), and Z2 (BPA-NI epoxy), used in a long-term aging study (n=48)

With reference now to FIG. 21, illustrated is metal exposure (enamel) ratings for three can types, X1 (BPA epoxy), Y2 (BPA-NI epoxy), and Z2 (BPA-NI epoxy), used in the long-term aging study (n=48). Lower current values correspond to more complete liner coverage and lower metal exposure. In some embodiments, metal exposure ratings, also referred to as enamel ratings, for the three can types evaluated in the long-term storage study are shown. The enamel rating quantifies the extent of exposed aluminum substrate by measuring electrical current flow through an electrolyte in contact with the internal can surface under an applied potential. The three can types include X1 (BPA epoxy), Y2 (BPA-NI epoxy), and Z2 (BPA-NI epoxy). As before, the letters X, Y, and Z designate can manufacturers, and the numerals "1" and "2" designate the liner type.

As illustrated in FIG. 21, enamel rating currents were below 4 mA for all 48 tested samples (n=48), indicating minimal exposed aluminum and adequate liner coverage. No statistically significant differences were detected among the three can groups, suggesting that the liner application met industry specifications for barrier performance at the time of manufacture. The results were well below the threshold of 5 mA generally recommended for highly corrosive beverages such as wine and far below the 75 mA limit typically used for less corrosive beverages such as beer. In an embodiment, these enamel-rating results demonstrate that all three liner types initially exhibited satisfactory electrical insulation properties. However, because long-term $H_2S$ formation and corrosion were later observed to differ among the same can groups, the enamel-rating test alone may not fully predict chemical resistance or performance over time. This finding supports the conclusion that liner-wine chemical compatibility, rather than initial electrical barrier integrity, is the dominant factor influencing can stability during extended storage.

Figure 22:
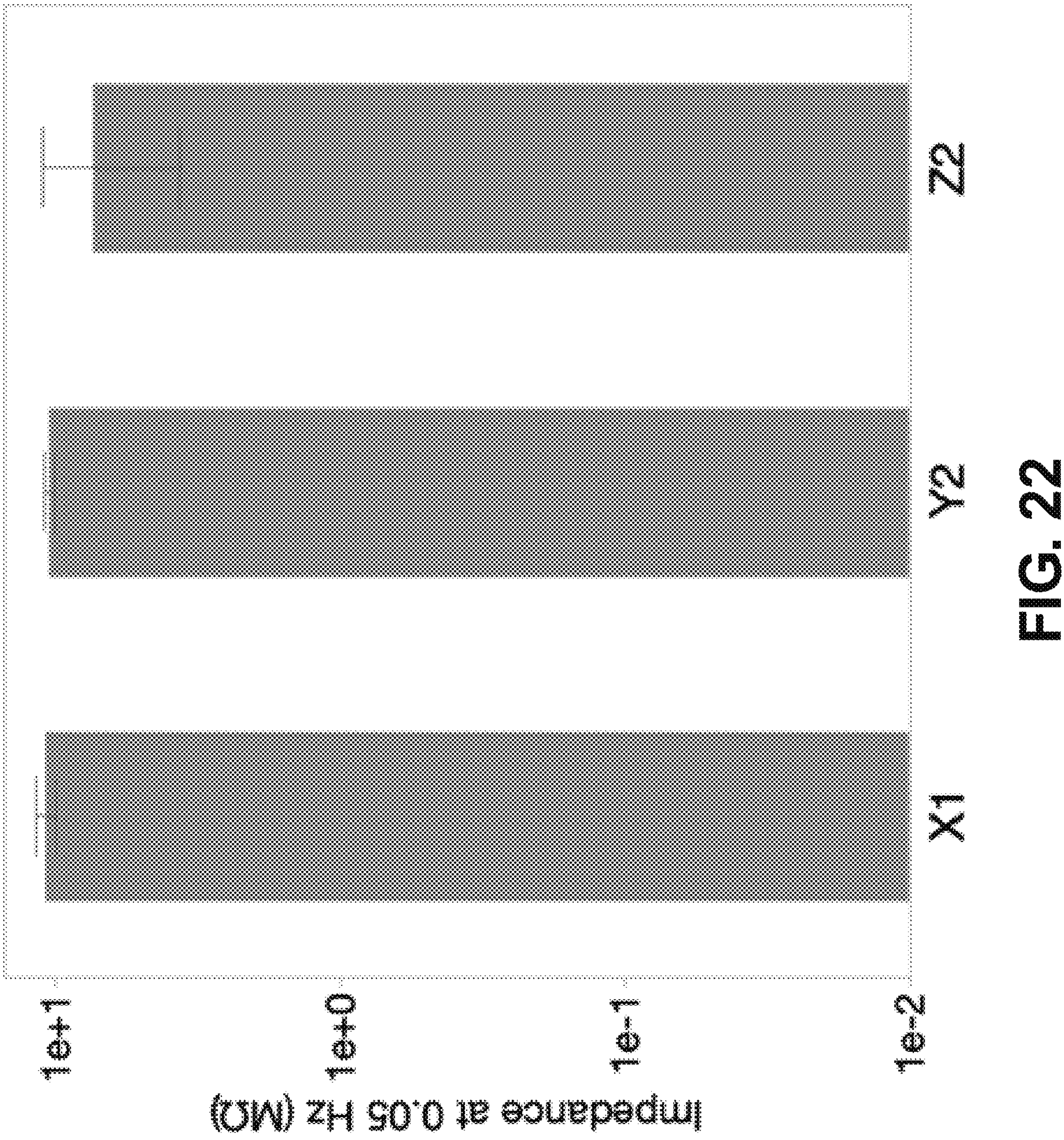
FIG. 22 illustrates impedance values at low frequency (0.05 Hz) for three can types, X1 (BPA epoxy), Y2 (BPA-NI epoxy), and Z2 (BPA-NI epoxy), used in a long-term aging study.

With reference now to FIG. 22, illustrated is impedance values at low frequency (0.05 Hz) for three can types, X1 (BPA epoxy), Y2 (BPA-NI epoxy), and Z2 (BPA-NI epoxy), used in the long-term aging study. Three technical replicates were tested for each can type (n=9). Error bars represent one standard error of the mean. In some embodiments, impedance values measured at a low-frequency operating point (0.05 Hz) for the three can types used in the long-term aging study are shown. The impedance values were obtained by electrochemical impedance spectroscopy (EIS) performed on intact, unused cans filled with a sodium chloride electrolyte. The evaluated can types included X1 (BPA epoxy), Y2 (BPA-NI epoxy), and Z2 (BPA-NI epoxy). As used herein, the letters X, Y, and Z designate can manufacturers, and the numerals "1" and "2" designate the liner type.

As depicted in FIG. 22, all three can types exhibited impedance magnitudes on the order of 10 MΩ at 0.05 Hz, a value consistent with a fully intact and continuous polymeric liner. Each can type was tested in triplicate (n=9 total), and error bars represent one standard error of the mean. No statistically significant differences in impedance were observed among the three liner groups, suggesting comparable initial electrochemical barrier performance across all tested cans. In some embodiments, the absence of significant variation in EIS-derived impedance among the liners indicates that, at time of manufacture, all coatings provided sufficient electrical insulation to limit ion transport through the film. However, long-term differences in hydrogen sulfide ($H_2S$) generation and corrosion behavior, as described elsewhere, imply that impedance measured immediately after filling may not capture liner degradation kinetics that manifest over time. The data therefore underscore that EIS can complement chemical compatibility testing when evaluating can performance for sulfur-containing beverages.

Figure 23:
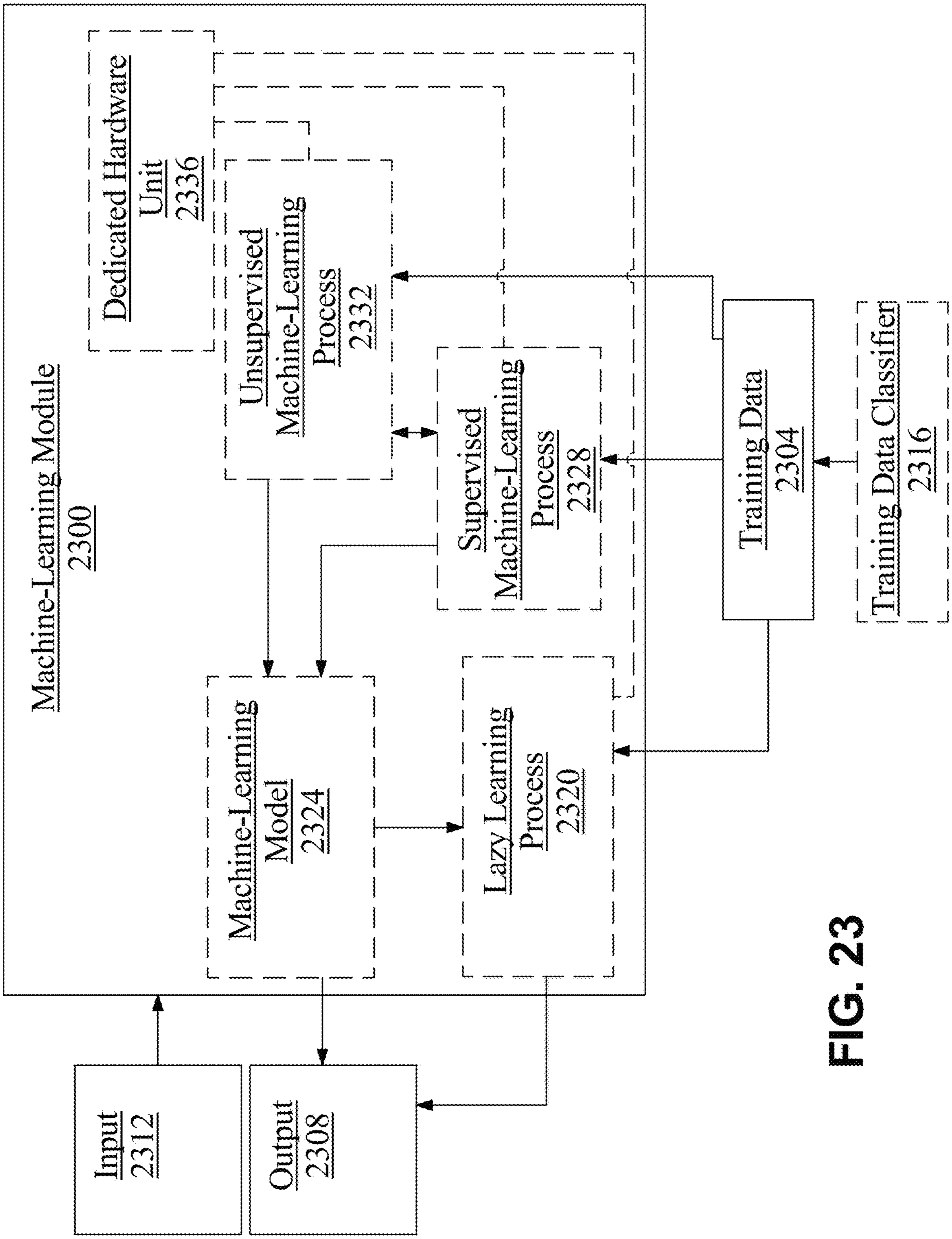
FIG. 23 is a diagram of an exemplary embodiment of a machine-learning module.

Referring now to FIG. 23, an exemplary embodiment of a machine-learning module 2300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 2304 to generate an algorithm instantiated in hardware or software logic, data structures, and/or functions that will be performed by a computing device/module to produce outputs 2308 given data provided as inputs 2312; this is in contrast to a non-machine learning software program where the commands to be executed are determined in advance by a user and written in a programming language.

Still referring to FIG. 23, "training data," as used herein, is data containing correlations that a machine-learning process may use to model relationships between two or more categories of data elements. For instance, and without limitation, training data 2304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 2304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 2304 according to various correlations; correlations may indicate causative and/or predictive links between categories of data elements, which may be modeled as relationships such as mathematical relationships by machine-learning processes as described in further detail below. Training data 2304 may be formatted and/or organized by categories of data elements, for instance by associating data elements with one or more descriptors corresponding to categories of data elements. As a non-limiting example, training data 2304 may include data entered in standardized forms by persons or processes, such that entry of a given data element in a given field in a form may be mapped to one or more descriptors of categories. Elements in training data 2304 may be linked to descriptors of categories by tags, tokens, or other data elements; for instance, and without limitation, training data 2304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 23, training data 2304 may include one or more elements that are not categorized; that is, training data 2304 may not be formatted or contain descriptors for some elements of data. Machine-learning algorithms and/or other processes may sort training data 2304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 2304 to be made applicable for two or more distinct machine-learning algorithms as described in further detail below. Training data 2304 used by machine-learning module 2300 may correlate any input data as described in this disclosure to any output data as described in this disclosure. As a non-limiting illustrative example, input data may include liner composition spectra, beverage chemistry parameters (e.g., pH, $SO_2$, ethanol concentration), and optical liner integrity readings, and output data may include a predicted liner compatibility score, an expected hydrogen sulfide formation rate, and a recommended formulation or packaging adjustment.

Further referring to FIG. 23, training data may be filtered, sorted, and/or selected using one or more supervised and/or unsupervised machine-learning processes and/or models as described in further detail below; such models may include without limitation a training data classifier 2316. Training data classifier 2316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 2300 may generate a classifier using a classification algorithm, defined as a processes whereby a computing device and/or any module and/or component operating thereon derives a classifier from training data 2304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 2316 may classify elements of training data to sub-populations of liner-beverage interaction profiles, such as cohorts of candidate liner compositions exhibiting similar hydrogen sulfide generation behavior, corrosion onset rates, or spectral similarity features derived from coating or compositional data, thereby enabling targeted retraining or parameter optimization for those subgroups.

Still referring to FIG. 23, a computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 23, a computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 23, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $\alpha_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 23, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 23, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 23, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 23, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 23, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 23, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 23, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 23, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}:X_{new}=\frac{X-X_{min}}{X_{max}-X_{min}}.$$

Feature scaling may include mean normalization, which involves use of a mean value of a set and/or subset of values, $X_{mean}$ with maximum and minimum values:

$$X_{new}=\frac{X-X_{mean}}{X_{max}-X_{min}}.$$

Feature scaling may include standardization, where a difference between X and $X_{mean}$ in is divided by a standard deviation $\sigma$ of a set or subset of values:

$$X_{new}=\frac{X-X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new}=\frac{X-X_{median}}{IQR}.$$

Persons skilled in the art, upon reviewing the entirety of this disclosure, will IQR be aware of various alternative or additional approaches that may be used for feature scaling.

Further referring to FIG. 23, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 23, machine-learning module 2300 may be configured to perform a lazy-learning process 2320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 2304. Heuristic may include selecting some number of highest-ranking associations and/or training data 2304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 23, machine-learning processes as described in this disclosure may be used to generate machine-learning models 2324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 2324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 2324 may be generated by creating an artificial neural network, such as a convolutional neural network comprising an input layer of nodes, one or more intermediate layers, and an output layer of nodes. Connections between nodes may be created via the process of "training" the network, in which elements from a training data 2304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 23, machine-learning algorithms may include at least a supervised machine-learning process 2328. At least a supervised machine-learning process 2328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 2304. Persons skilled in the art, upon reviewing the entirety of this disclosure, will be aware of various possible variations of at least a supervised machine-learning process 2328 that may be used to determine relation between inputs and outputs. Supervised machine-learning processes may include classification algorithms as defined above.

With further reference to FIG. 23, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Continuing to refer to FIG. 23, evaluation of error function and/or other comparison results may include comparison of each of error function and/or other comparison results to a maximum single error threshold; in other words, a criterion of evaluation may include performing iterative retraining if any single comparison and/or error function output exceeds maximum single error threshold or if a count of single comparison and/or error function outputs exceeding single error threshold exceeds a threshold number and/or proportion of overall error function and/or other comparison results. Alternatively or additionally, evaluation of error function and/or other comparison results may include comparison of an aggregated plurality of error function and/or other comparison results to an aggregate error threshold; in other words, a criterion of evaluation may include performing iterative retraining if a result of averaging or otherwise aggregating a plurality such as some or all evaluated function and/or other comparison results exceeds aggregate error threshold. Aggregation may be performed in any manner of aggregation described in this disclosure and/or any combination thereof. Criteria for evaluations may be evaluated separately such that failing any one criterion causes iterative retraining; alternatively or additionally evaluation results may be combined according to one or more logical or other rules.

As a non-limiting, illustrative example, and still referring to FIG. 23, where outputs to be compared by error function are numerical values, error function may include subtraction of one from the other to derive an absolute value and/or mean squared error. Where outputs and/or training examples are represented as a binary classification, an error function may include a hinge loss function, sigmoid cross entropy loss function, weighted cross entropy loss function, or the like. Where output and/or exemplary output in a training set is a classification to three or more values, error function may include a softmax cross entropy loss function, a sparse cross entropy loss function, a Kullback-Leibler divergence loss function, or the like. Where both retaining and training with include supervised training, retraining may use a different error function, different weight update functions and/or parameters, or the like than in the training stage. For instance, and without limitation, when a previous iterative retraining process included training using examples from until a first convergence threshold and/or epsilon value and/or neighborhood is met, a subsequent iterative retraining process may include a lower convergence threshold, a smaller value of epsilon, or the like. Iterative retraining may include using one or more examples that were not used in any previous training and/or retraining process; for instance, where convergence was initially and/or previously achieved using a first subset of examples a subsequent retraining process may use examples from a second subset of examples, which may be wholly disjoint from first subset and/or have one or more elements that are not found in first subset.

Still referring to FIG. 23, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 23, machine learning processes may include at least an unsupervised machine-learning processes 2332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 2332 may not require a response variable; unsupervised processes 2332 may be used to find interesting patterns and/or inferences between variables, to determine a degree of correlation between two or more variables, or the like.

Still referring to FIG. 23, machine-learning module 2300 may be designed and configured to create a machine-learning model 2324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 23, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including, without limitation, support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 23, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 23, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 23, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 23, one or more processes or algorithms described above may be performed by at least a dedicated hardware unit 2336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 2336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 2336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 2336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 24:
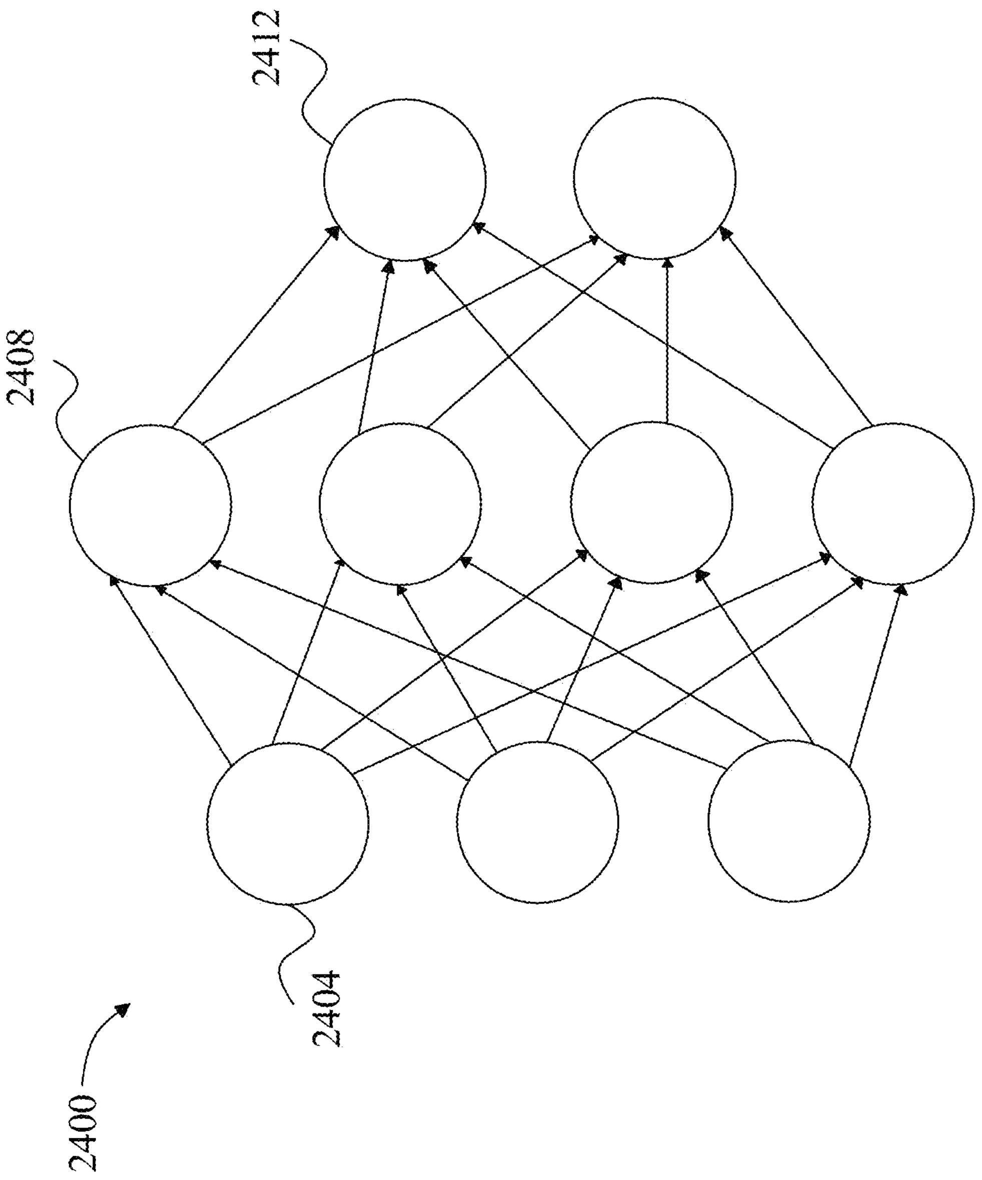
FIG. 24 is a diagram of an exemplary embodiment of a neural network.

Referring now to FIG. 24, an exemplary embodiment of neural network 2400 is illustrated. A neural network 2400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 2404, one or more intermediate layers 2408, and an output layer of nodes 2412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 25:
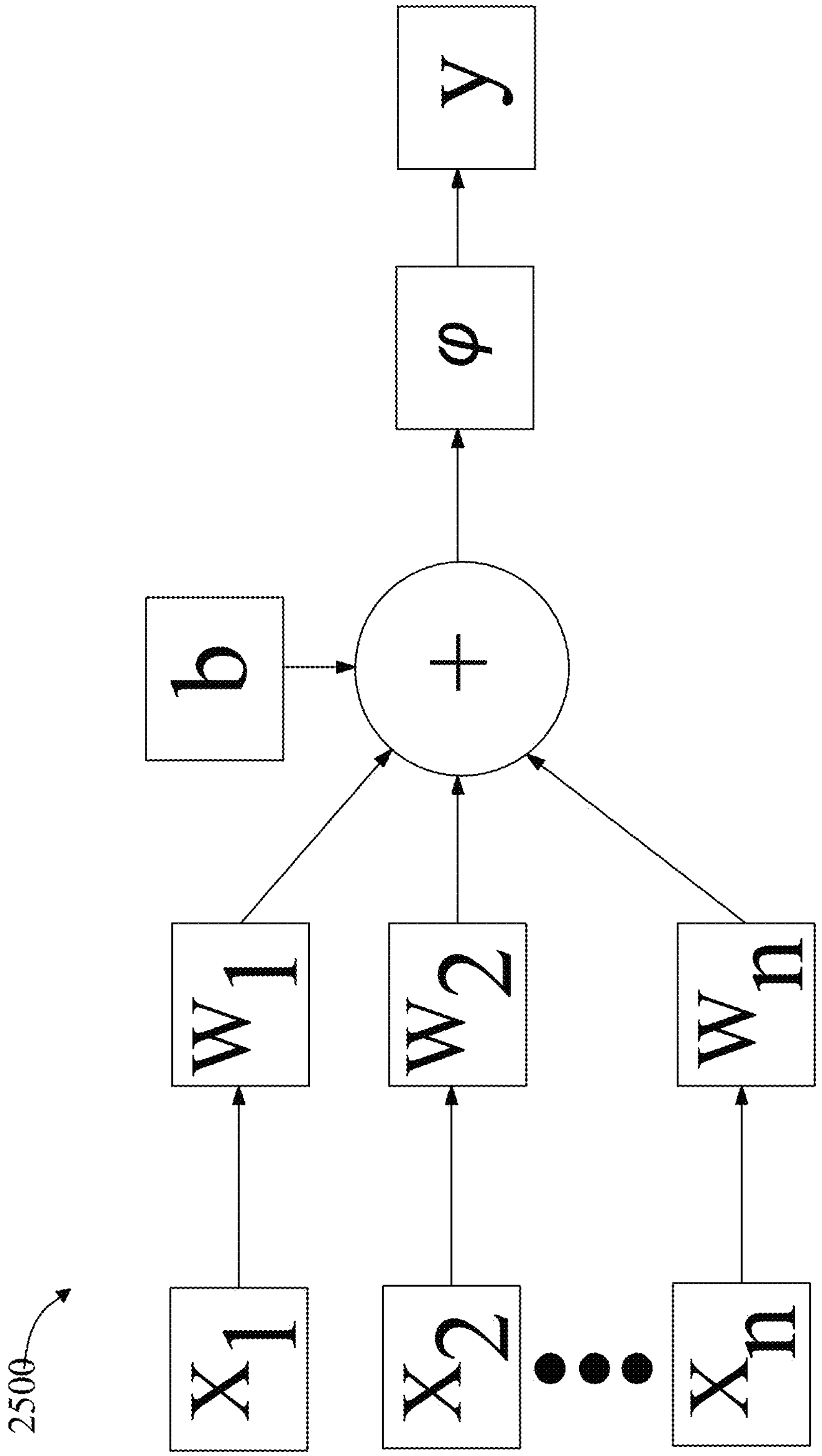
FIG. 25 is a diagram of an exemplary embodiment of a node of a neural network.

Referring now to FIG. 25, an exemplary embodiment of a node 2500 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x - e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as f(x)=x*sigmoid(x), a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$, or of other coefficients and/or parameters of an activation function, may be determined by training a neural network using training data, which may be performed using any suitable process as described above. Each weight in a neural network may, without limitation, be updated and/or tuned, based on an error function J, using a backpropagation updating method, such as:

$$w_{new} = w_{old} - \alpha \frac{dJ}{dw}$$

where $w_{new}$ is the updated weight value, $w_{old}$ is the previous weight value, α is a parameter to set the learning rate, and $$\frac{dJ}{dw}$$

is the partial derivative of with respect to weight w.

Figure 26:
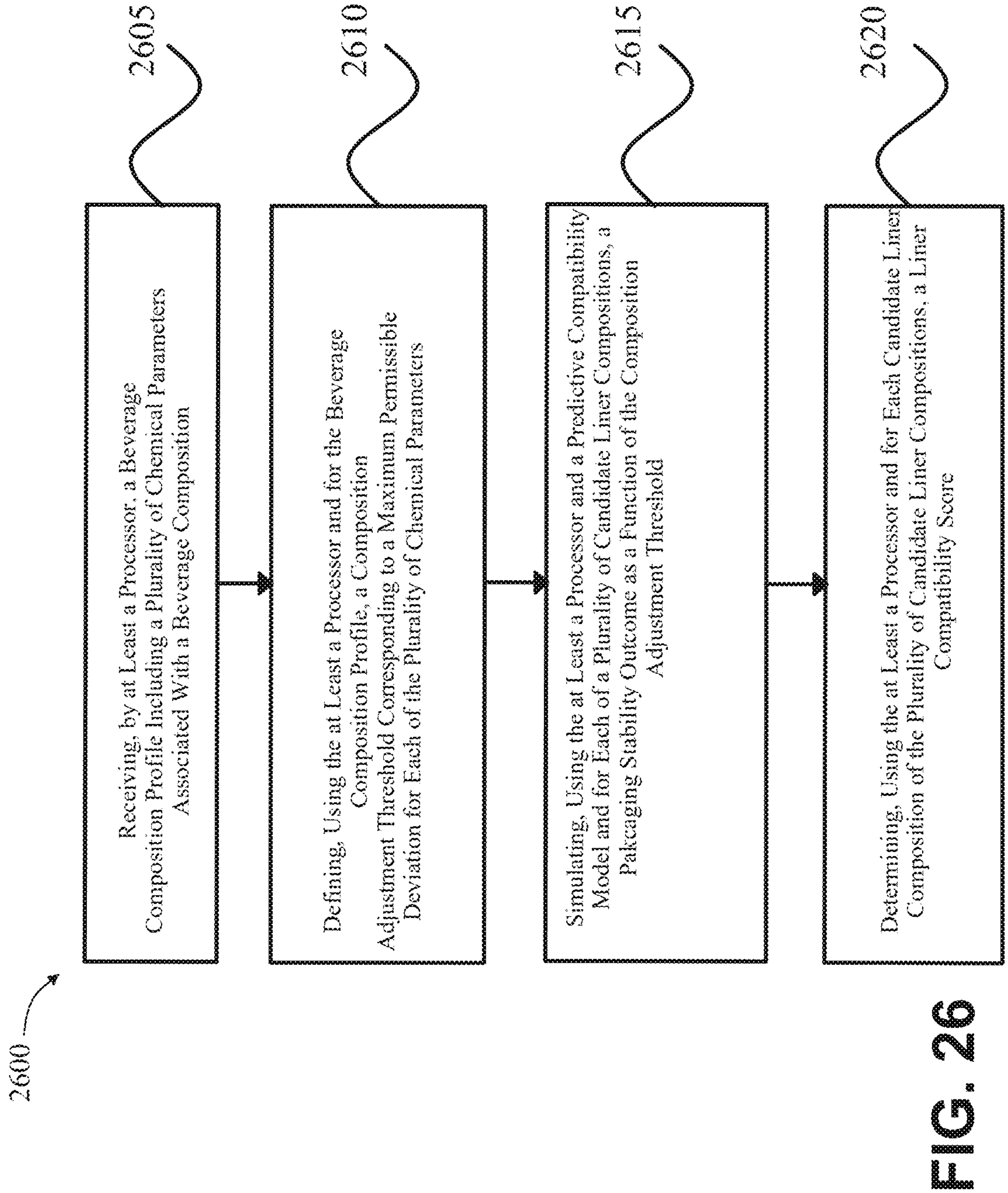
FIG. 26 is a flow diagram of an exemplary method of determining beverage compositions for aluminum can packaging.

Referring now to FIG. 26, a block diagram of an exemplary method 2600 of determining beverage compositions for aluminum can packaging is illustrated. Method 2600 may include a step 2605 of receiving, by at least a processor, a beverage composition profile including a plurality of chemical parameters associated with a beverage composition. In an embodiment, the beverage composition profile may be received from a data file uploaded from one or more of an external information system and a quality-control database. This may be implemented, without limitation, as referenced in FIGS. 1-25.

In continued reference to FIG. 26, method 2600 may include a step 2610 of defining, using the at least a processor and for the beverage composition profile, a composition adjustment threshold corresponding to a maximum permissible deviation for each of the plurality of chemical parameters. In an embodiment, defining the composition adjustment threshold may include accessing a composition adjustment matrix specifying, for each chemical parameter of the plurality of chemical parameters, an upper and lower deviation limit defining the composition adjustment threshold and applying the composition adjustment matrix to the beverage composition profile to constrain simulated parameter changes within the defined upper and lower deviation limits. In an embodiment, defining the composition adjustment threshold may include receiving, from a user, the maximum permissible deviations for each of the plurality of chemical parameters and appending the maximum permissible deviation for each of the plurality of chemical parameters to the beverage composition profile. In an embodiment, defining the composition adjustment threshold may include identifying, for each chemical parameter of the plurality of chemical parameters, a baseline value as a function of a measured condition of the beverage composition, determining, for the baseline value, an allowable range of variation as a function of the maximum permissible deviation, and mapping, for each chemical parameter of the plurality of chemical parameters, the allowable range of variation to a corresponding chemical parameter to define the composition adjustment threshold. This may be implemented, without limitation, as referenced in FIGS. 1-25.

With further reference to FIG. 26, method 2600 may include a step 2615 of simulating, using a predictive compatibility model and for each of a plurality of candidate liner compositions, a packaging stability outcome as a function of the composition adjustment threshold. In an embodiment, the predictive compatibility model may include a machine-learning model that has been trained on a compatibility dataset comprising historical beverage chemistry data, liner composition variables, and corresponding packaging stability outcomes. This may be implemented, without limitation, as referenced in FIGS. 1-25.

Still referring to FIG. 26, method 2600 may include a step 2620 of determining, using the at least a processor and for each candidate liner composition of the plurality of candidate liner compositions, a liner compatibility score. In an embodiment, determining the liner compatibility score may include computing, for each candidate liner composition, a numerical stability index representing a confidence value that the beverage composition will remain chemically and sensorially stable within the composition adjustment threshold. In an embodiment, the liner compatibility score may be transmitted to an external processing framework. This may be implemented, without limitation, as referenced in FIGS. 1-25.

With continued reference to FIG. 26, method 2600 may include generating a liner compatibility profile, including, for each candidate liner composition, one or more of one or more limiting chemical parameters and at least one packaging configuration parameter. In an embodiment, method 2600 may further include generating the at least one packaging configuration parameter, wherein generating the at least one packaging configuration parameter includes: identifying, for each candidate liner composition, one or more limiting chemical parameters as a function of the liner compatibility score, selecting a candidate liner composition as a function of the liner compatibility score and a predetermined compatibility threshold, and outputting, as a function of the candidate liner composition, the at least one packaging configuration parameter. This may be implemented, without limitation, as referenced in FIGS. 1-25.

In further reference to FIG. 26, method 2600 may include outputting the liner compatibility profile as a data object. This may be implemented, without limitation, as referenced in FIGS. 1-25.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 27:
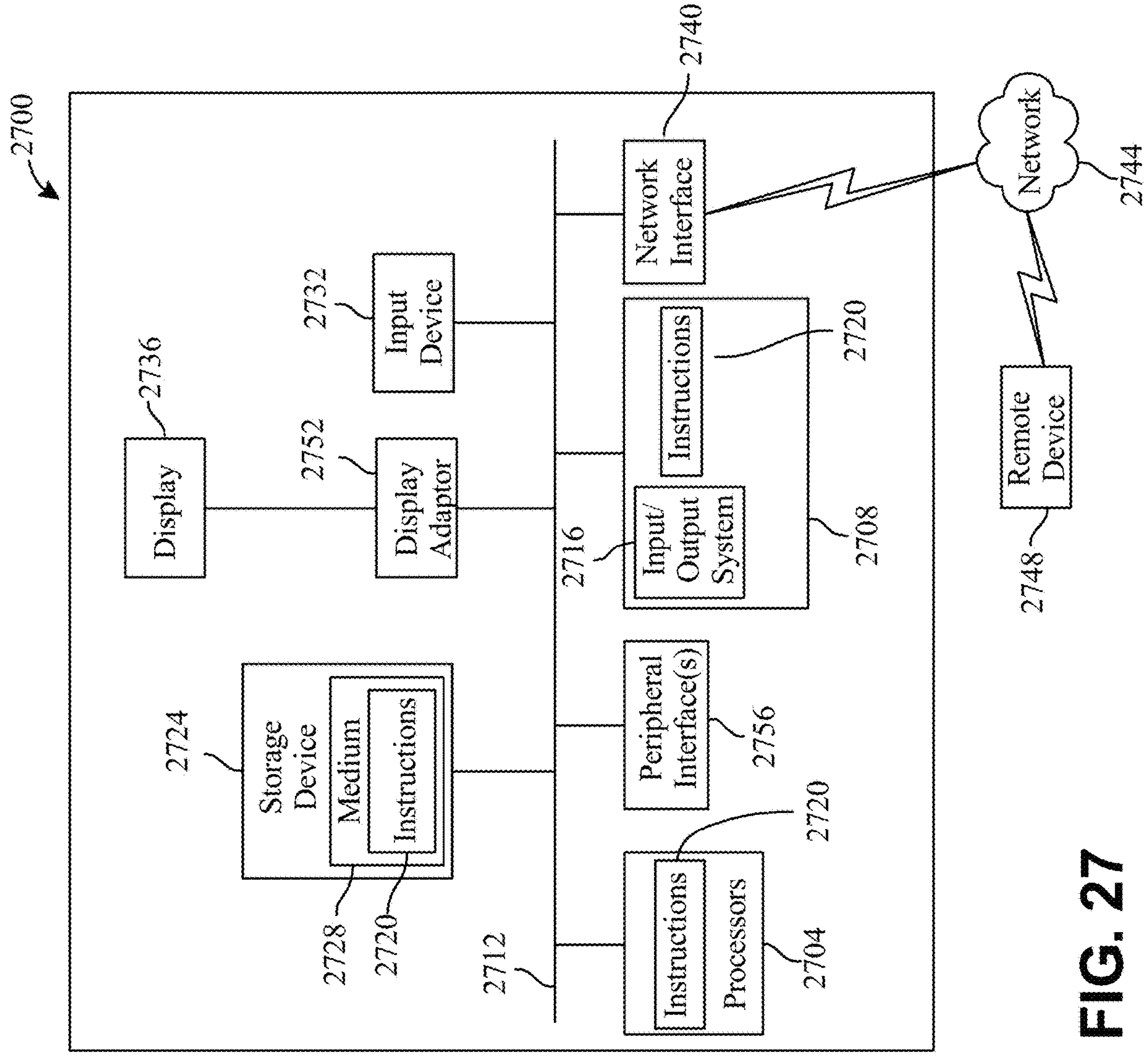
FIG. 27 is a block diagram of a computing system that can be used to implement any one or more of the methodologies disclosed herein and any one or more portions thereof.

FIG. 27 shows a diagrammatic representation of one embodiment of a computing device in the exemplary form of a computer system 2700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2700 includes a processor 2704 and a memory 2708 that communicate with each other, and with other components, via a bus 2712. Bus 2712 may include any of several types of bus structures including, but not limited to, a memory bus, a memory controller, a peripheral bus, a local bus, and any combinations thereof, using any of a variety of bus architectures.

Processor 2704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 2704 may be organized according to Von Neumann and/or Harvard architecture as a non-limiting example. Processor 2704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC). Each processor and/or processor core may perform a state transition, instruction, and/or instruction step during a period of a "clock," or a regular oscillator that generates periodic output waveform, such as a square wave, having a regular period; different processors and/or cores may have distinct clocks. A processor may operate as and/or include a processing unit that performs instruction inputs, arithmetic operations, logical operations, memory retrieval operations, memory allocation operations, and/or input and output operations; a control circuit or module within a processor may determine which of the above-described functions a processor and/or unit within a processor will perform on a given clock cycle. A processor may include a plurality of processing units or "cores," each of which performs the above-described actions; multiple cores may work on disparate instruction sets and/or may work in parallel. A single core may also include multiple arithmetic, logic, or other units that can work in parallel with each other. Parallel computing between and/or within processors and/or cores may include multithreading processes and/or protocols such as without limitation Tomasulo's algorithm. As used in this disclosure, "a processor," and/or "configuring a processor,"

is equivalent for the purposes of this disclosure to at least a processor, a plurality of processors, and/or a plurality of processor cores, and/or programming at least a processor, a plurality of processors, and/or a plurality of processor cores, which may be configured to operate on instructions in parallel and/or sequentially according to multithreading algorithms, parallel computing, load and/or task balancing, and/or virtualization, for instance and without limitation as described below.

Memory 2708 may include various components (e.g., machine-readable media) including, but not limited to, a random-access memory component, a read only component, and any combinations thereof. In one example, a basic input/output system 2716 (BIOS), including basic routines that help to transfer information between elements within computer system 2700, such as during start-up, may be stored in memory 2708. Memory 2708 may also include (e.g., stored on one or more machine-readable media) instructions (e.g., software) 2720 embodying any one or more of the aspects and/or methodologies of the present disclosure. In another example, memory 2708 may further include any number of program modules including, but not limited to, an operating system, one or more application programs, other program modules, program data, and any combinations thereof. Memory 2708 may include a primary memory and a secondary memory. "Primary memory," which may be implemented, without limitation as "random access memory" (RAM), is memory used for temporarily storing data for active use by a processor. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power.

Computer system 2700 may also include a storage device 2724. Examples of a storage device (e.g., storage device 2724) include, but are not limited to, a hard disk drive, a magnetic disk drive, an optical disc drive in combination with an optical medium, a solid-state memory device, and any combinations thereof. Storage device 2724 may be connected to bus 2712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2724 (or one or more components thereof) may be removably interfaced with computer system 2700 (e.g., via an external port connector (not shown)). Particularly, storage device 2724 and an associated machine-readable medium 2728 may provide nonvolatile and/or volatile storage of machine-readable instructions, data structures, program modules, and/or other data for computer system 2700. In some embodiments, storage device 2724 and/or devices "Secondary memory" also known as "storage," "hard disk drive" and the like for the purposes of this disclosure is a long-term storage device in which an operating system and other information is stored; operating system and/or main program instructions may alternatively or additionally be stored in hard-coded memory ROM, or the like. In one or remote embodiments, information may be retrieved from secondary memory and copied to primary memory during use. In one or more embodiments, secondary memory may be referred to as non-volatile memory wherein information is preserved even during a loss of power. In some embodiments, data from secondary memory is transferred to primary memory before being accessed by a processor. In one or more embodiments, data is transferred from secondary to primary memory wherein circuitry may access the information from primary memory. In one example, software 2720 may reside, completely or partially, within machine-readable medium 2728. In another example, software 2720 may reside, completely or partially, within processor 2704.

Computer system 2700 may also include an input device 2732. In one example, a user of computer system 2700 may enter commands and/or other information into computer system 2700 via input device 2732. Examples of an input device 2732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2732 may be interfaced to bus 2712 via any of a variety of interfaces (not shown) including, but not limited to, a serial interface, a parallel interface, a game port, a USB interface, a FIREWIRE interface, a direct interface to bus 2712, and any combinations thereof. Input device 2732 may include a touch screen interface that may be a part of or separate from display 2736, discussed further below. Input device 2732 may be utilized as a user selection device for selecting one or more graphical representations in a graphical interface as described above.

A user may also input commands and/or other information to computer system 2700 via storage device 2724 (e.g., a removable disk drive, a flash drive, etc.) and/or network interface device 2740. A network interface device, such as network interface device 2740, may be utilized for connecting computer system 2700 to one or more of a variety of networks, such as network 2744, and one or more remote devices 2748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2744, may employ a wired and/or a wireless mode of communication. In general, any network topology may be used. Information (e.g., data, software 2720, etc.) may be communicated to and/or from computer system 2700 via network interface device 2740.

Computer system 2700 may further include a video display adapter 2752 for communicating a displayable image to a display device, such as display 2736. Examples of a display device include, but are not limited to, a liquid crystal display (LCD), a cathode ray tube (CRT), a plasma display, a light emitting diode (LED) display, and any combinations thereof. Display adapter 2752 and display 2736 may be utilized in combination with processor 2704 to provide graphical representations of aspects of the present disclosure. In addition to a display device, computer system 2700 may include one or more other peripheral output devices including, but not limited to, an audio speaker, a printer, and any combinations thereof. Such peripheral output devices may be connected to bus 2712 via a peripheral interface 2756. Examples of a peripheral interface include, but are not limited to, a serial port, a USB connection, a FIREWIRE connection, a parallel connection, and any combinations thereof.

Further referring to FIG. 27, a computing device may include any computing device as described in this disclosure, including without limitation a microcontroller, microprocessor, digital signal processor (DSP) and/or system on a chip (SoC) as described in this disclosure. A computing device may include, be included in, and/or communicate with a mobile device such as a mobile telephone or smartphone. A computing device may include a single device having components as described above operating independently, or may include two or more such devices and/or components thereof operating in concert, in parallel, sequentially or the like; two or more devices, processors, memory elements, and the like may be included together in a single computing device or in two or more computing devices. A computing device may interface or communicate with one or more additional devices as described below in further detail via a network interface device.

In some embodiments, and still referring to FIG. 27, a computing device may be a component of a combination of at least a computing device; at least a computing device may include, as a non-limiting example, a first computing device or cluster of computing devices in a first location and a second computing device or cluster of computing devices in a second location. At least a computing device may include one or more computing devices dedicated to data storage, security, distribution of traffic for load balancing, and the like. At least a computing device may distribute one or more computing tasks as described below across a plurality of computing devices of computing device, which may operate in parallel, in series, redundantly, or in any other manner used for distribution of tasks or memory between computing devices. At least a computing device may be implemented, as a non-limiting example, using a "shared nothing" architecture.

With continued reference to FIG. 27, one or more programs or software instructions may include a principal program and/or operating system; principal program and/or operating system may be a program that runs automatically upon startup of a computing device and manages computer hardware and software resources. Principal program and/or operating system may include "startup," "loop," and/or "main" programs on a microcontroller; such programs may initialize hardware resources and subsequently iterate through a series of instructions to make function calls, read in data at input ports, output data at output ports, and process interrupts caused by asynchronous data inputs or the like. Principal program and/or operating system may include, without limitation, an operating system, which may schedule program tasks to be implemented by one or more processors, act as an intermediary between one or more programs and inputs, outputs, hardware and/or memory. Examples of operating systems include without limitation Unix, Linux, Microsoft Windows, Android, Disc Operating System (DOS) and the like. Operating systems may include, without limitation, multi-computer operating systems that run across multiple computing devices, real-time operating systems, and hypervisors. A "hypervisor," as used in this disclosure, is an operating system that runs a virtual machine and/or container, where virtual machines and/or containers create virtual interfaces for programs that mimic the behavior of hardware elements such as processors and/or memory; interactions with such virtual interfaces appear, to programs executed on virtual machines, to function as interactions with physical hardware, while in reality the hypervisor and/or programs such as containers (1) receive inputs from programs to the virtual resources and allocate such inputs to physical hardware that is not directly accessible to the programs, and (2) receive outputs from physical hardware and transmit such outputs to the programs in the form of apparent outputs from the virtual hardware. In some cases, one or more of computing system 2700, processor 2704, and memory 2708 may be virtualized; that is, a virtual machine and/or container may interact directly with such computing system 2700, processor 2704, and/or memory 2708, while managing communications therefrom and thereto via a virtual interface with programs. Computer virtualization may include dividing, or augmenting computing resources into a virtual machine, operating system, processor, and/or container. Virtualization of computer resources may be implemented through use of (1) multiple components, or portions thereof, working in concert, as if they were one unified (virtual) component; and/or (2) a portion of one or more components working as though it were a complete (virtual) component. For instance, where processor 2704 comprises a plurality of processors and/or processor cores, virtualization may, in some cases, simulate or emulate a single (virtual) processor whose functions are allocated to one or more of the plurality of processors and/or processor cores. In this case, while processor 2704 may be said to be virtualized, the processor 2704, nevertheless, comprises actual hardware processor(s) or portion(s) thereof. Accordingly, in this disclosure, where a processor is said to perform instructions, such processor may comprise a virtualized processor, comprising a plurality or portion of hardware processors. Likewise, in this disclosure, where a memory is said to contain (i.e., store) instructions, such memory may comprise a virtualized memory, comprising a plurality or portion of memories. Technologies that enable such virtualization include (1) QEMU, www.qemu.org; (2) VMware by Broadcom Inc of Palo Alto, California; (3) VirtualBox by Oracle Corporation headquartered in Austin, Texas; and (4) kernel-based virtual machine (KVM) www.linux-kvm.org.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining beverage compositions for aluminum can packaging, the system comprising:

at least a processor; and a memory communicatively connected to the at least a processor, wherein the memory contains instructions configuring the at least a processor to:

receive a beverage composition profile comprising a plurality of chemical parameters associated with a beverage composition;

define, for the beverage composition profile, a composition adjustment threshold corresponding to a maximum permissible deviation for each of the plurality of chemical parameters, wherein defining the composition adjustment threshold comprises:

accessing a composition adjustment matrix specifying, for each chemical parameter of the plurality of chemical parameters, an upper and lower deviation limit defining the composition adjustment threshold; and applying the composition adjustment matrix to the beverage composition profile to constrain simulated parameter changes within the defined upper and lower deviation limits;

simulate, using a predictive compatibility model and for each of a plurality of candidate liner compositions, a chemical interaction between the beverage composition and each candidate liner composition to generate a predicted packaging stability outcome indicative of material degradation, corrosion potential, or compositional instability as a function of the composition adjustment threshold; and determine, for each candidate liner composition of the plurality of candidate liner compositions, a liner compatibility score based on the predicted packaging stability outcome, wherein the liner compatibility score is useable to select a liner composition for physical aluminum can packaging of the beverage composition over a simulated storage duration.

2. The system of claim 1, wherein the beverage composition profile is received from a data file uploaded from one or more of:

an external information system; and a quality-control database.

3. The system of claim 1, wherein defining the composition adjustment threshold comprises:

receiving, from a user, the maximum permissible deviations for each of the plurality of chemical parameters; and appending the maximum permissible deviation for each of the plurality of chemical parameters to the beverage composition profile.

4. The system of claim 1, wherein defining the composition adjustment threshold comprises:

identifying, for each chemical parameter of the plurality of chemical parameters, a baseline value as a function of a measured condition of the beverage composition;

determining, for the baseline value, an allowable range of variation as a function of the maximum permissible deviation; and mapping, for each chemical parameter of the plurality of chemical parameters, the allowable range of variation to a corresponding chemical parameter to define the composition adjustment threshold.

5. The system of claim 1, wherein the predictive compatibility model comprises a machine-learning model that has been trained on a compatibility dataset comprising historical beverage chemistry data, liner composition variables, and corresponding packaging stability outcomes.

6. The system of claim 1, wherein determining the liner compatibility score comprises computing, for each candidate liner composition, a numerical stability index representing a confidence value that the beverage composition will remain chemically and sensorially stable within the composition adjustment threshold.

7. The system of claim 1, wherein the liner compatibility score is transmitted to an external processing framework.

8. The system of claim 1, wherein the at least a processor is further configured to generate a liner compatibility profile, comprising, for each candidate liner composition, one or more of:

the liner compatibility score;

one or more limiting chemical parameters; and at least one packaging configuration parameter.

9. The system of claim 8, wherein the at least a processor is further configured to generate the at least one packaging configuration parameter, wherein generating the at least one packaging configuration parameter comprises:

identifying, for each candidate liner composition, one or more limiting chemical parameters as a function of the liner compatibility score;

selecting a candidate liner composition as a function of the liner compatibility score and a predetermined compatibility threshold; and outputting, as a function of the candidate liner composition, the at least one packaging configuration parameter.

10. The system of claim 8, wherein the at least a processor is further configured to output the liner compatibility profile as a data object.

11. A method of determining beverage compositions for aluminum can packaging, the method comprising:

receiving, by at least a processor, a beverage composition profile comprising a plurality of chemical parameters associated with a beverage composition;

defining, using the at least a processor and for the beverage composition profile, a composition adjustment threshold corresponding to a maximum permissible deviation for each of the plurality of chemical parameters, wherein defining the composition adjustment threshold comprises:

accessing a composition adjustment matrix specifying, for each chemical parameter of the plurality of chemical parameters, an upper and lower deviation limit defining the composition adjustment threshold; and applying the composition adjustment matrix to the beverage composition profile to constrain simulated parameter changes within the defined upper and lower deviation limits;

simulating, using the at least a processor and a predictive compatibility model and for each of a plurality of candidate liner compositions, a chemical interaction between the beverage composition and each candidate liner composition to generate a predicted packaging stability outcome indicative of material degradation, corrosion potential, or compositional instability as a function of the composition adjustment threshold; and determining, using the at least a processor and for each candidate liner composition of the plurality of candidate liner compositions, a liner compatibility score based on the predicted packaging stability outcome, wherein the liner compatibility score is useable to select a liner composition for physical aluminum can packaging of the beverage composition over a simulated storage duration.

12. The method of claim 11, wherein the beverage composition profile is received from a data file uploaded from one or more of:

an external information system; and a quality-control database.

13. The method of claim 11, wherein defining the composition adjustment threshold comprises:

receiving, from a user, the maximum permissible deviations for each of the plurality of chemical parameters; and appending the maximum permissible deviation for each of the plurality of chemical parameters to the beverage composition profile.

14. The method of claim 11, wherein defining the composition adjustment threshold comprises:

identifying, for each chemical parameter of the plurality of chemical parameters, a baseline value as a function of a measured condition of the beverage composition;

determining, for the baseline value, an allowable range of variation as a function of the maximum permissible deviation; and mapping, for each chemical parameter of the plurality of chemical parameters, the allowable range of variation to a corresponding chemical parameter to define the composition adjustment threshold.

15. The method of claim 11, wherein the predictive compatibility model comprises a machine-learning model that has been trained on a compatibility dataset comprising historical beverage chemistry data, liner composition variables, and corresponding packaging stability outcomes.

16. The method of claim 11, wherein determining the liner compatibility score comprises computing, for each candidate liner composition, a numerical stability index representing a confidence value that the beverage composition will remain chemically and sensorially stable within the composition adjustment threshold.

17. The method of claim 11, wherein the liner compatibility score is transmitted to an external processing framework.

18. The method of claim 11, further comprising generating a liner compatibility profile, comprising, for each candidate liner composition, one or more of:

the liner compatibility score;

one or more limiting chemical parameters; and at least one packaging configuration parameter.

19. The method of claim 18, further comprising generating the at least one packaging configuration parameter, wherein generating the at least one packaging configuration parameter comprises:

identifying, for each candidate liner composition, one or more limiting chemical parameters as a function of the liner compatibility score;

selecting a candidate liner composition as a function of the liner compatibility score and a predetermined compatibility threshold; and outputting, as a function of the candidate liner composition, the at least one packaging configuration parameter.

20. The method of claim 18, further comprising outputting the liner compatibility profile as a data object.

* * * * *